United States Patent
Zhou et al.

(10) Patent No.: US 10,233,255 B2
(45) Date of Patent: Mar. 19, 2019

(54) ANTIBODY THERAPEUTICS THAT BIND STAT3

(71) Applicant: Sorrento Therapeutics, Inc., San Diego, CA (US)

(72) Inventors: Heyue Zhou, San Diego, CA (US); Heehyoung Lee, Arcadia, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/496,994

(22) Filed: Apr. 25, 2017

(65) Prior Publication Data

US 2017/0306048 A1    Oct. 26, 2017

Related U.S. Application Data

(60) Provisional application No. 62/419,778, filed on Nov. 9, 2016, provisional application No. 62/327,178, filed on Apr. 25, 2016.

(51) Int. Cl.
*C07K 16/32* (2006.01)
*A61K 39/00* (2006.01)

(52) U.S. Cl.
CPC ........ *C07K 16/32* (2013.01); *A61K 2039/505* (2013.01); *C07K 2317/56* (2013.01); *C07K 2317/565* (2013.01); *C07K 2317/73* (2013.01); *C07K 2317/76* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 2006/0141514 A1 | 6/2006 | Rozzelle et al. |
| 2008/0124340 A1 | 5/2008 | Borges et al. |
| 2009/0233358 A1 | 9/2009 | Rhee et al. |
| 2012/0315282 A1 | 12/2012 | Bedinger et al. |
| 2013/0344069 A1 | 12/2013 | Gastwirt et al. |
| 2014/0011982 A1 | 1/2014 | Marasco et al. |
| 2014/0294841 A1 | 10/2014 | Scheinberg et al. |
| 2015/0316561 A1 | 11/2015 | Zhang et al. |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*
International Search Report for International Application No. PCT/US2017/029431 dated Sep. 18, 2017, 5 pages.

* cited by examiner

*Primary Examiner* — Nelson B Moseley, II
(74) *Attorney, Agent, or Firm* — Womble Bond Dickinson (US) LLP; Danielle L. Herritt; Cristin H. Cowles

(57) ABSTRACT

The present disclosure provides anti-STAT3 antibodies, and antigen-binding portions thereof. In certain embodiments, the antibodies or fragments thereof, are used for the treatment of cancer.

21 Claims, 56 Drawing Sheets
(8 of 56 Drawing Sheet(s) Filed in Color)
Specification includes a Sequence Listing.

Sequence 5' to 3' =
TCC ATG AGC TTC CTG ATG CT (SEQ ID NO: 19)

Sequence 5' to 3' =
TCC ATG AGC TTC CTG ATG CT
(SEQ ID NO: 19)

Ab#1: anti-STAT3 ST3G12
Ab#2: anti-STAT3 ST1A5
Ab#3: anti-STAT3 ST5G12

| | Stat3 (3G12)-Unmodified Superblock | Stat3 (3G12)-O/B Superblock |
|---|---|---|
| HilSlope | 1.456 | 1.588 |
| EC50 | 122.0 | 186.5 |

| | Stat3 (3G12)-Unmodified Superblock | Stat3 (3G12)-O/S Superblock |
|---|---|---|
| HilSlope | 0.9552 | 0.9834 |
| EC50 | 25.68 | 64.34 |

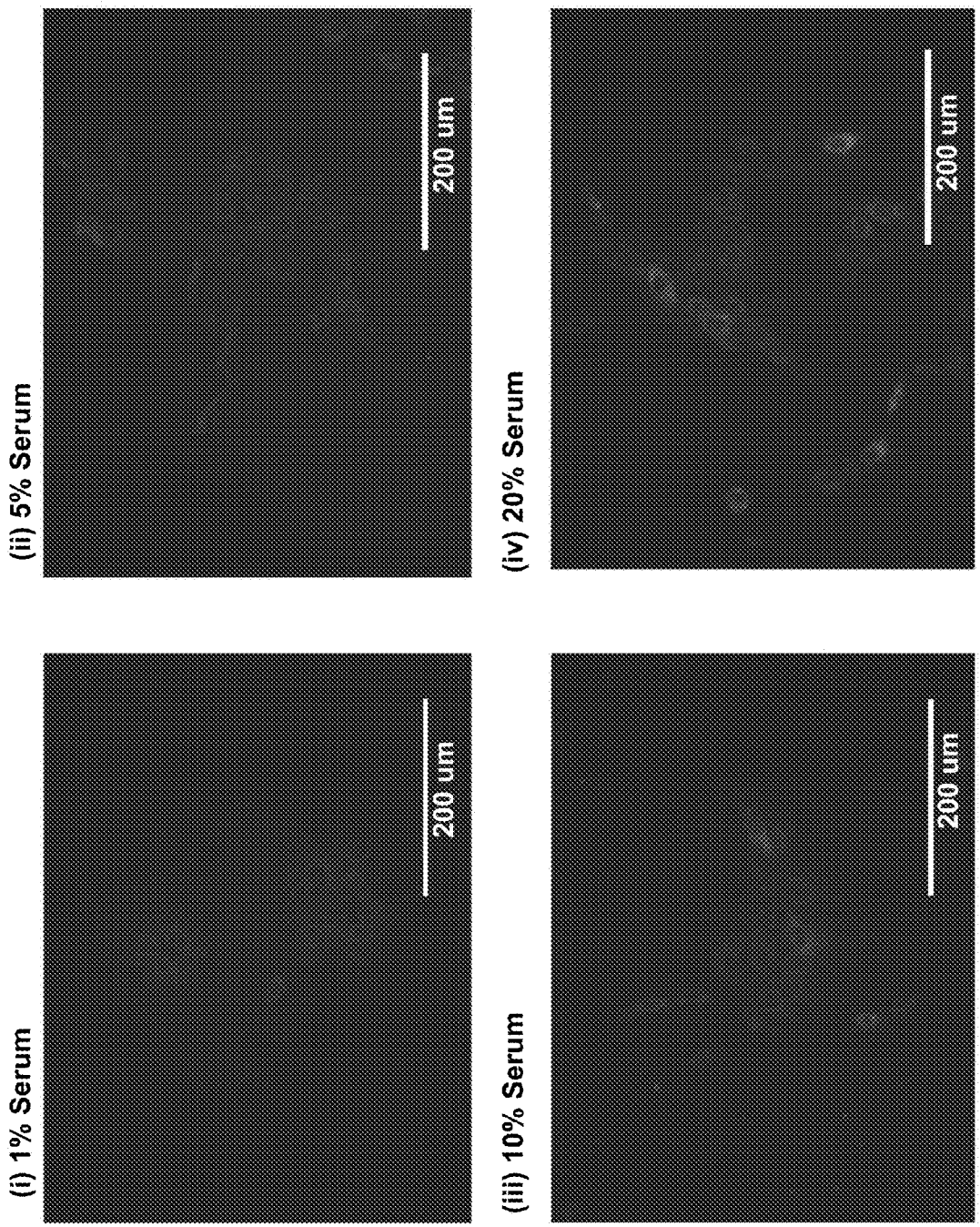

FIG. 14
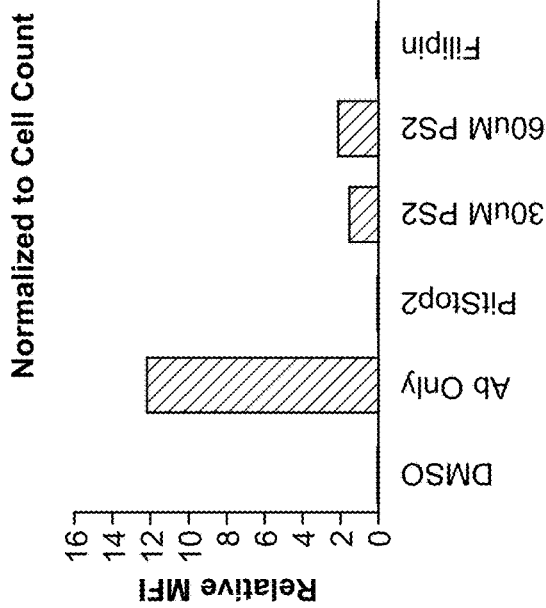
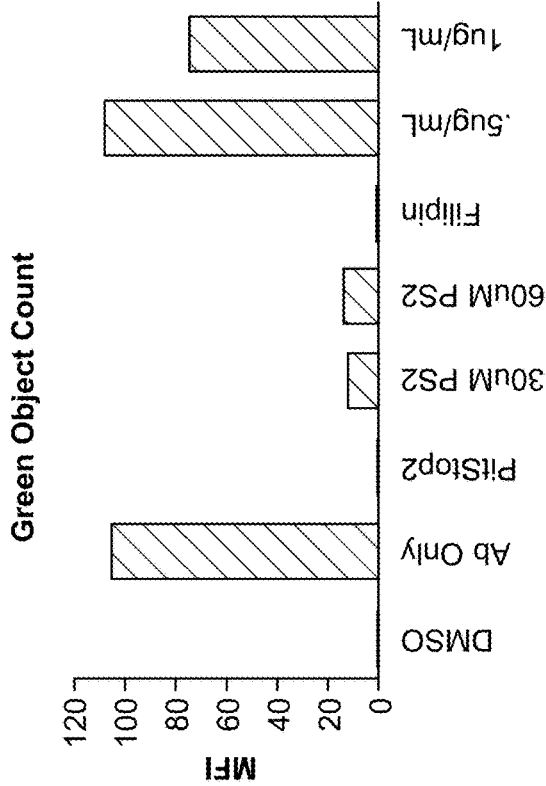

FIG. 15
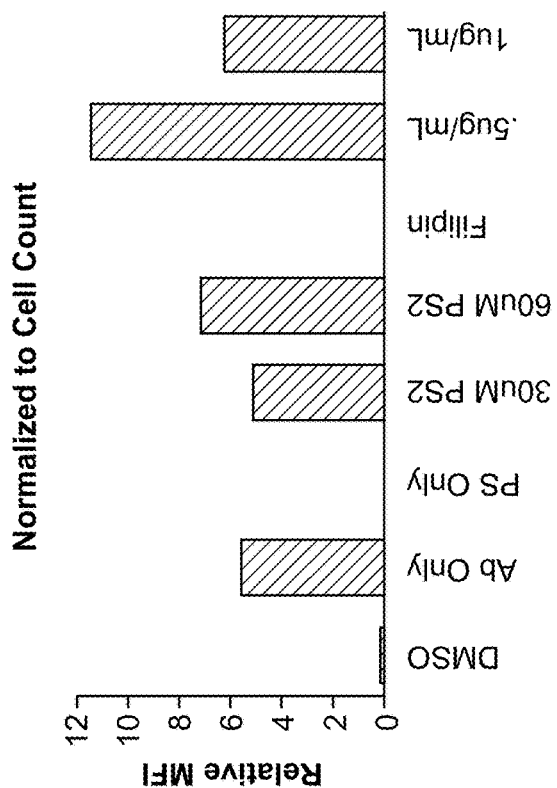
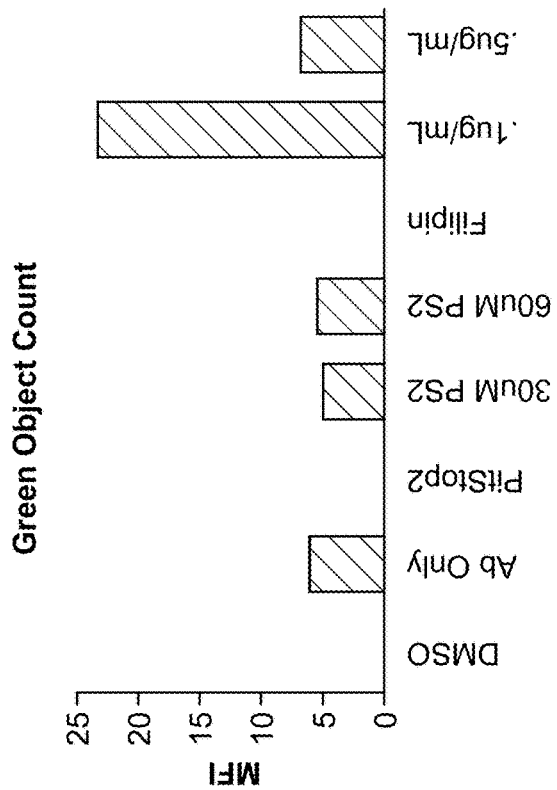

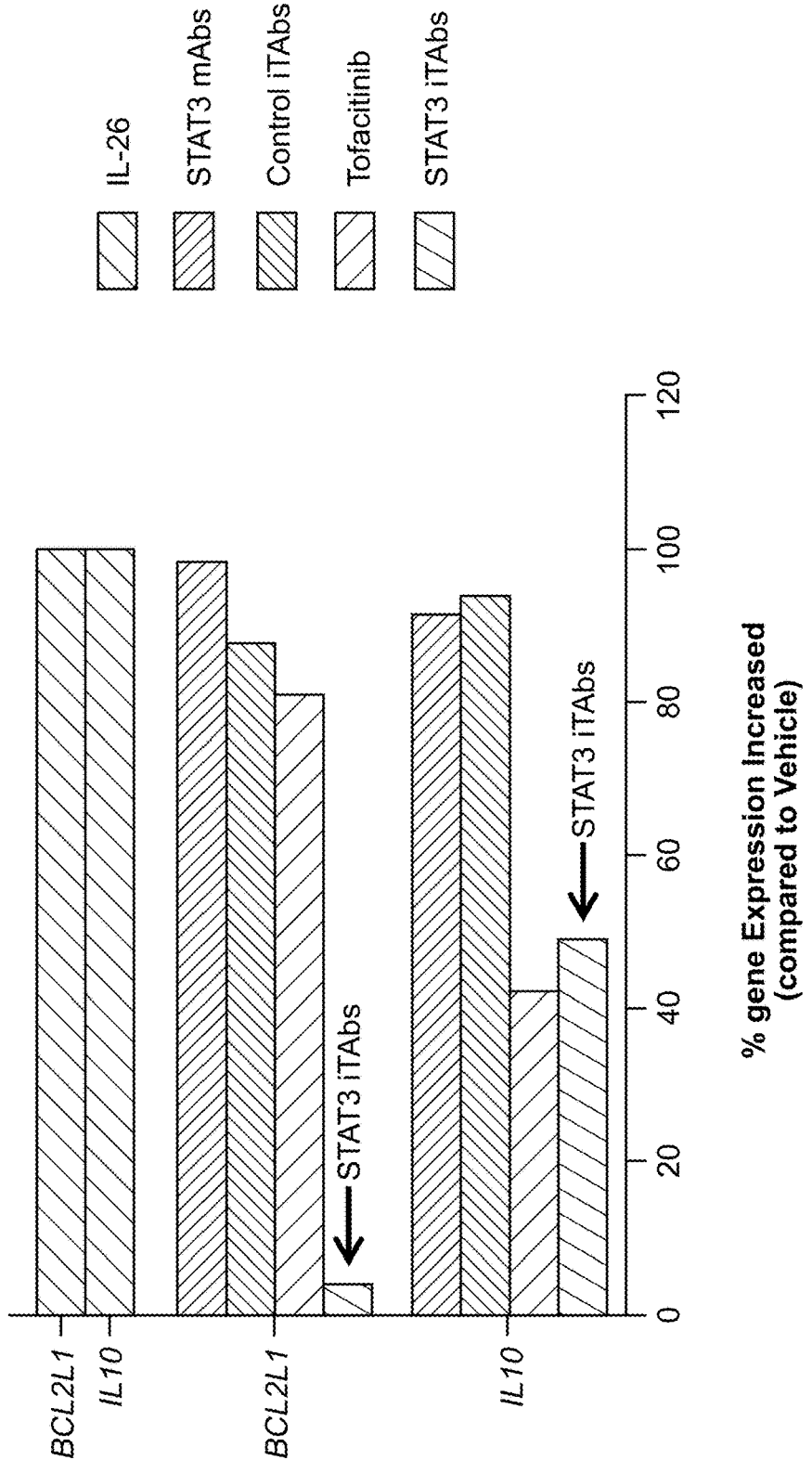

FIG. 18C
(i) Alexa Fluor® 488 dye-lebeled anti-STAT3 mAbs
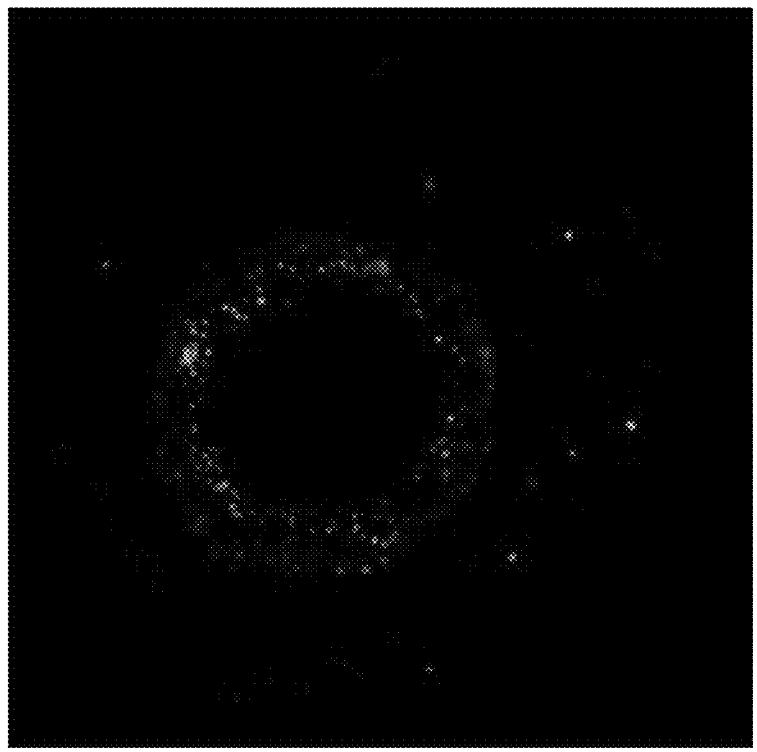
(ii) Alexa Fluor® 488 dye-lebeled STAT3 iTAbs
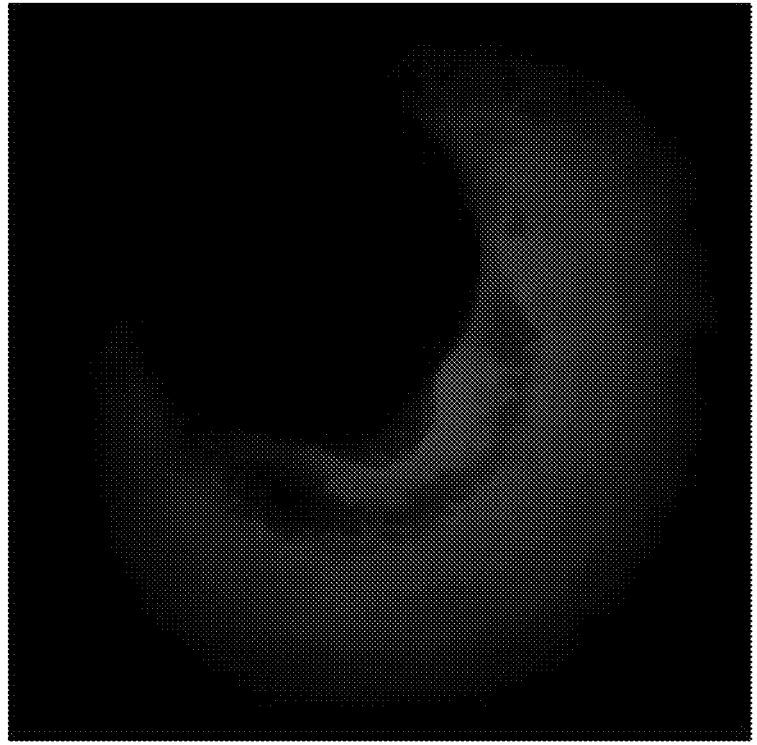

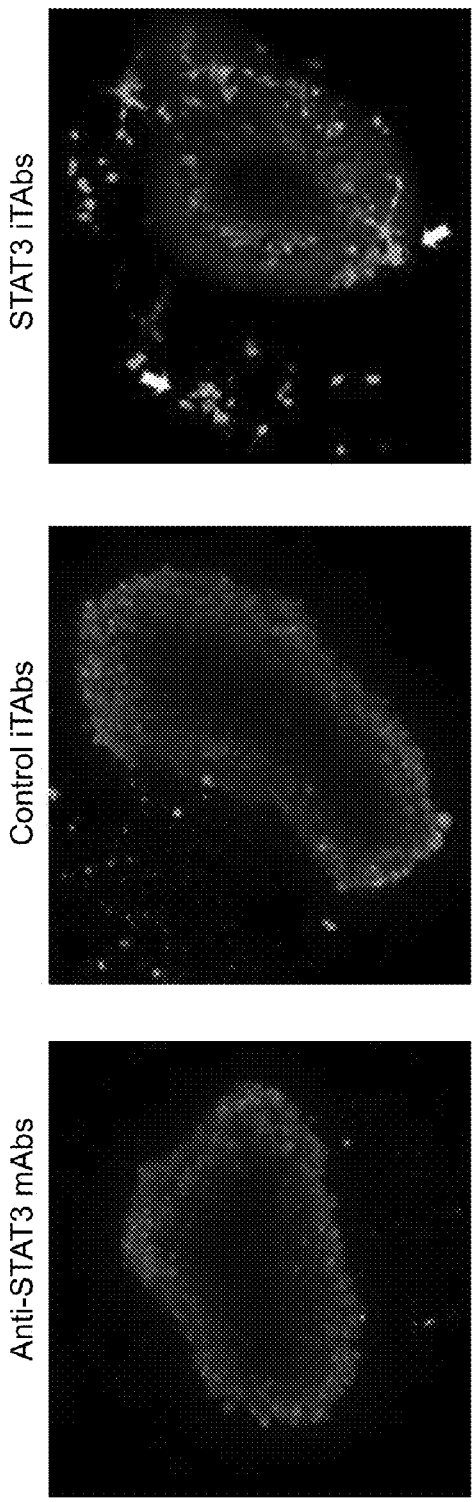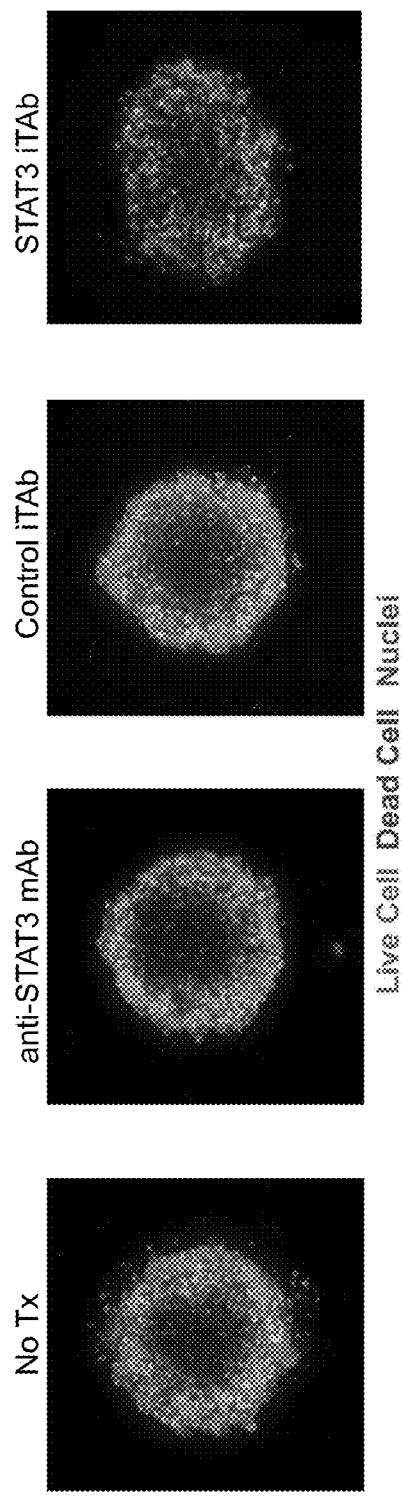
FIG. 20A
FIG. 20B

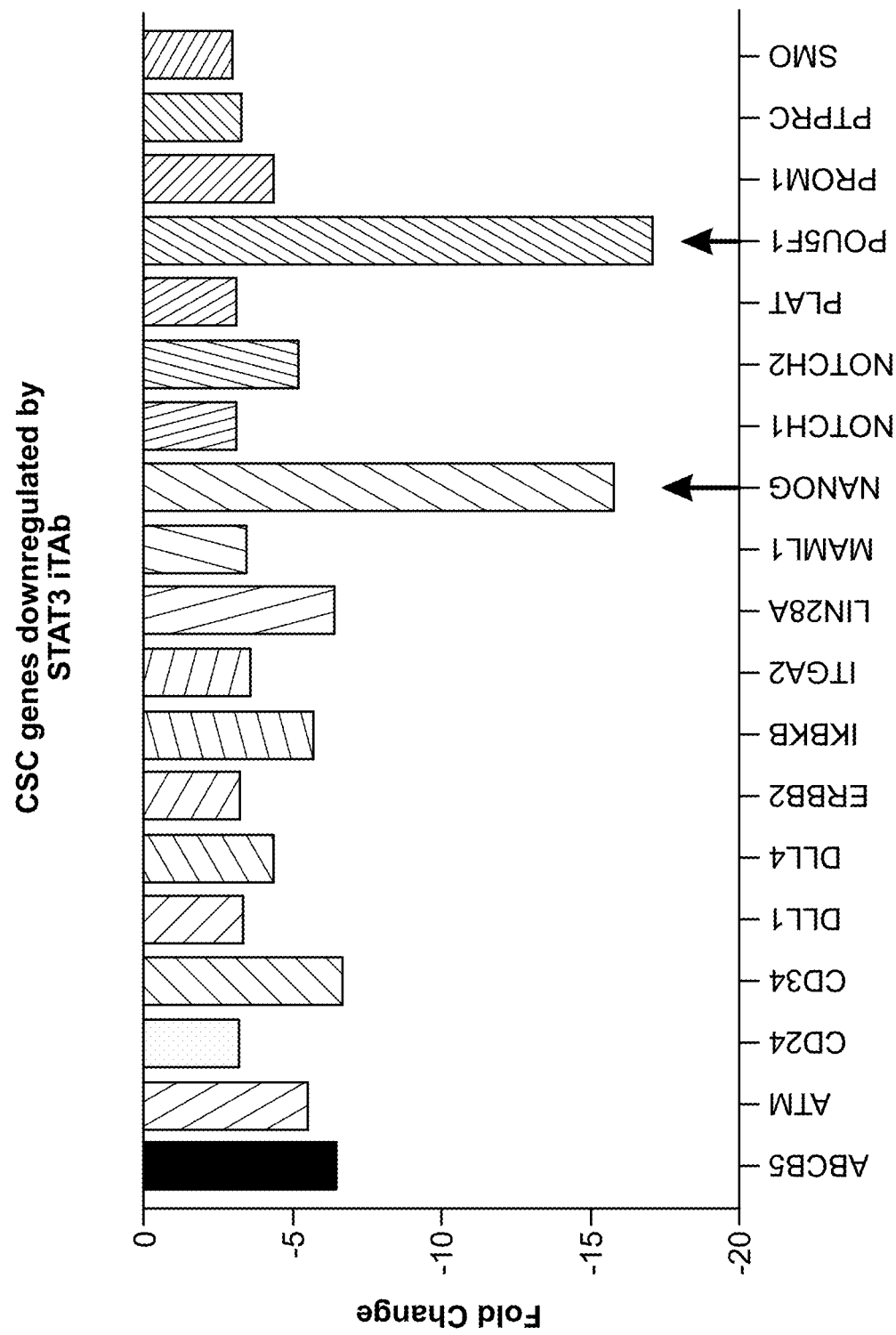

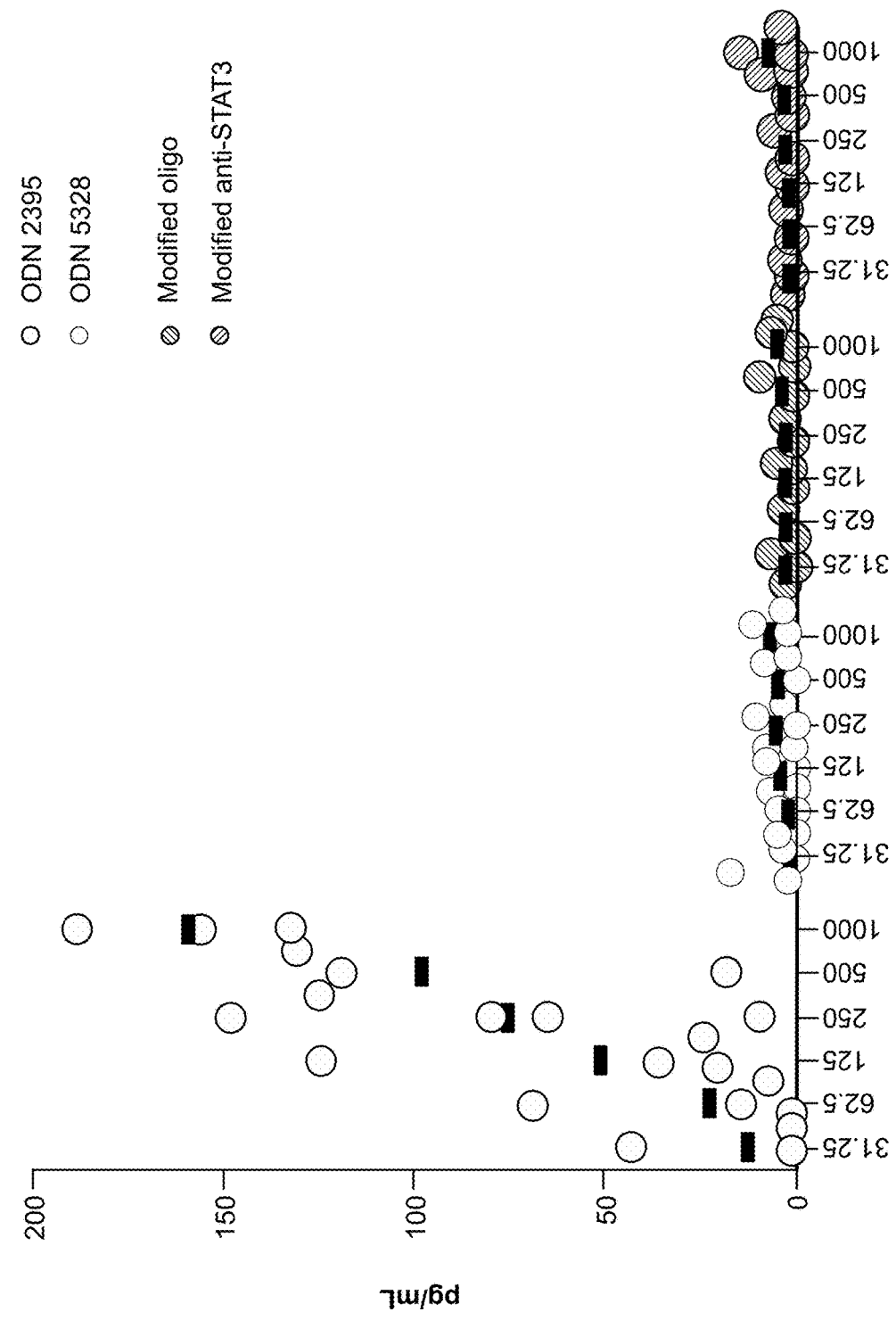

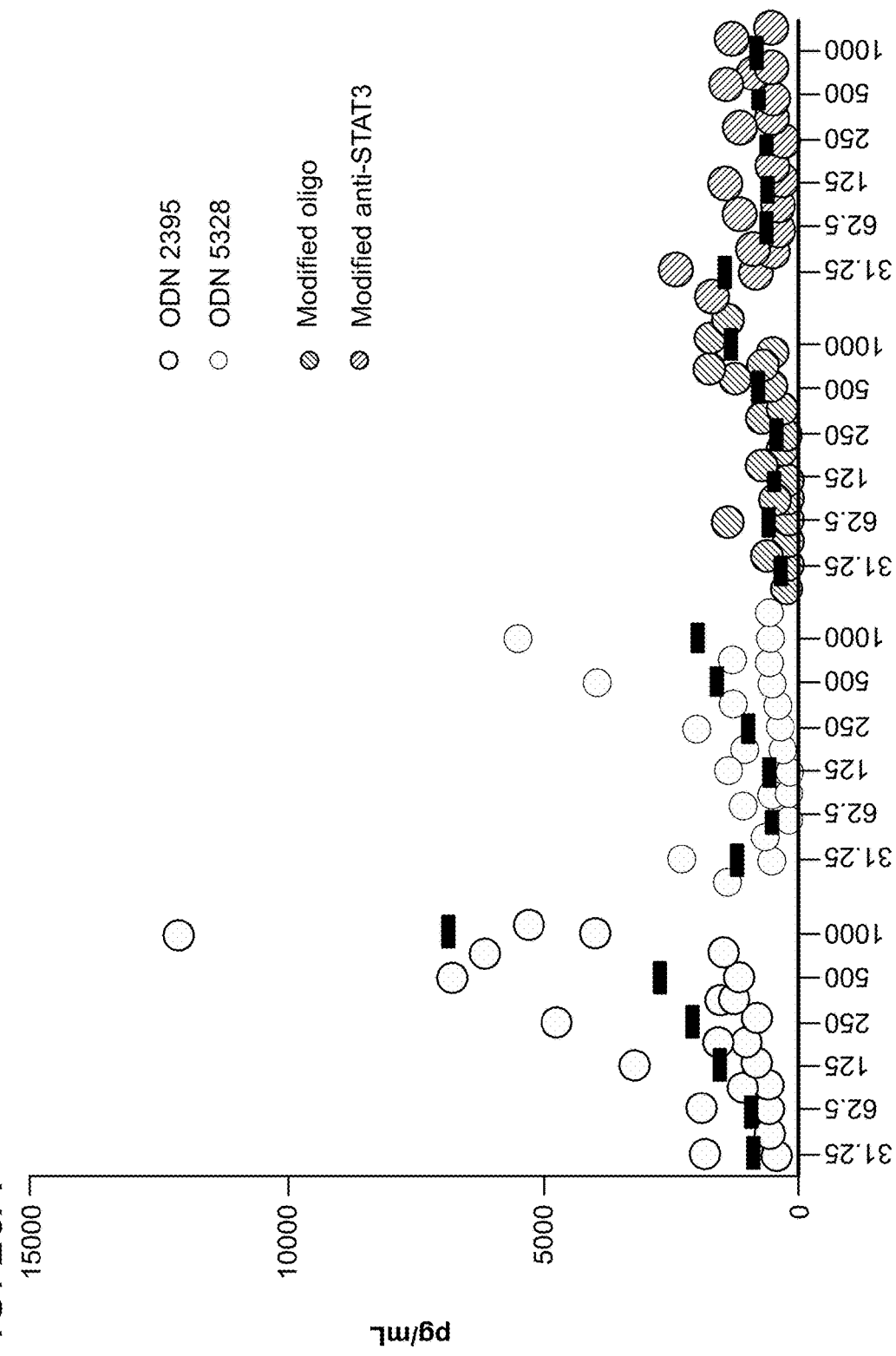

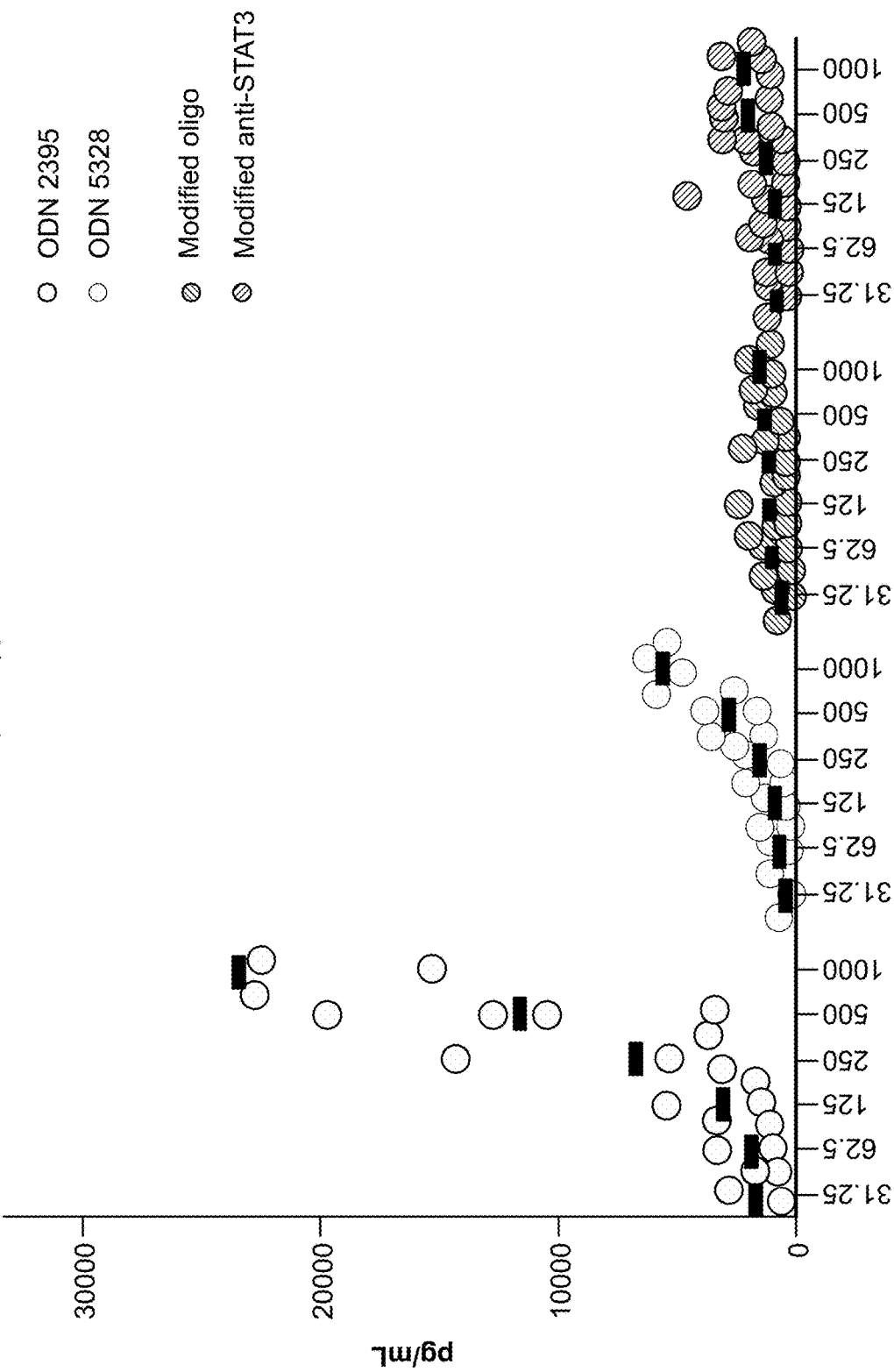

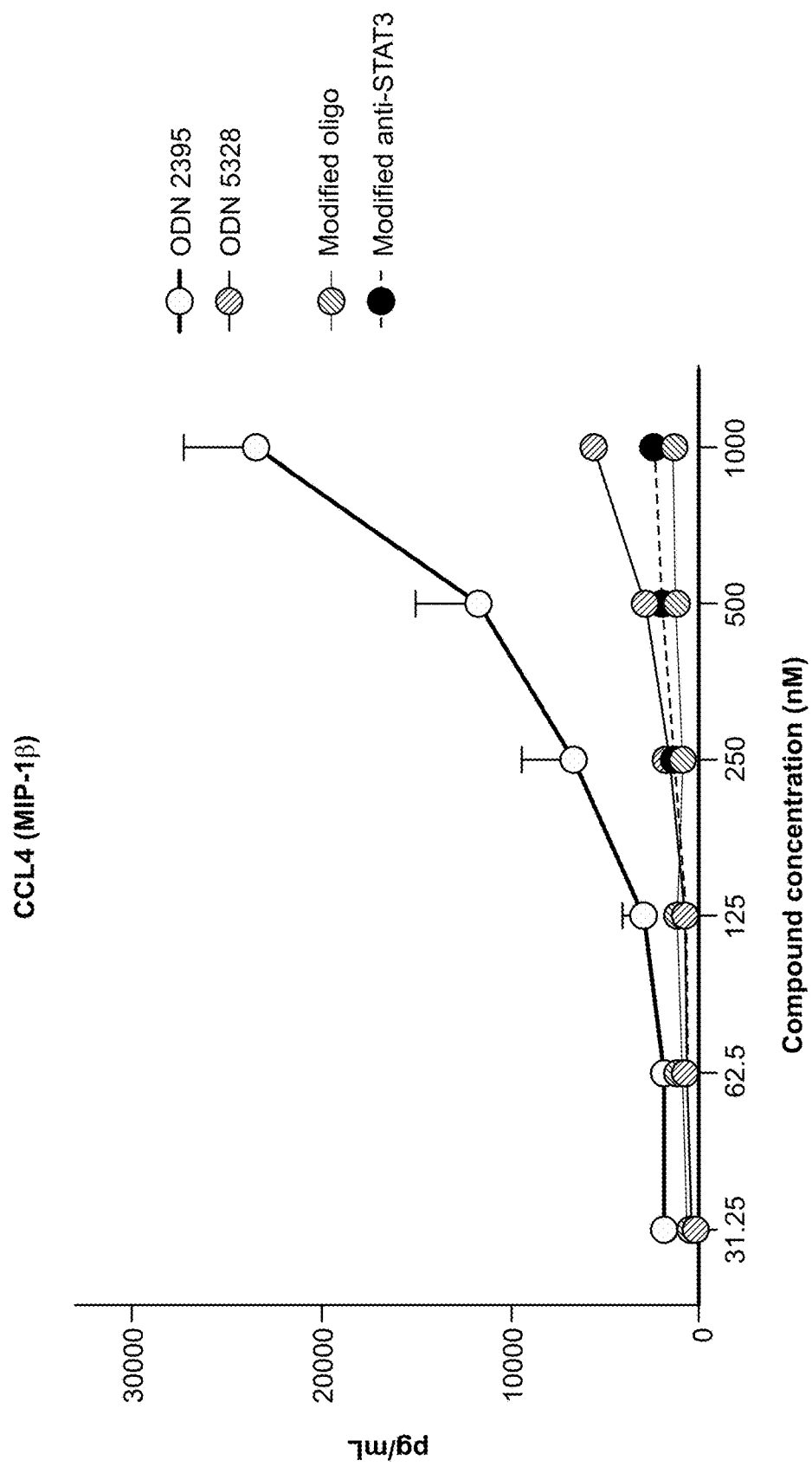

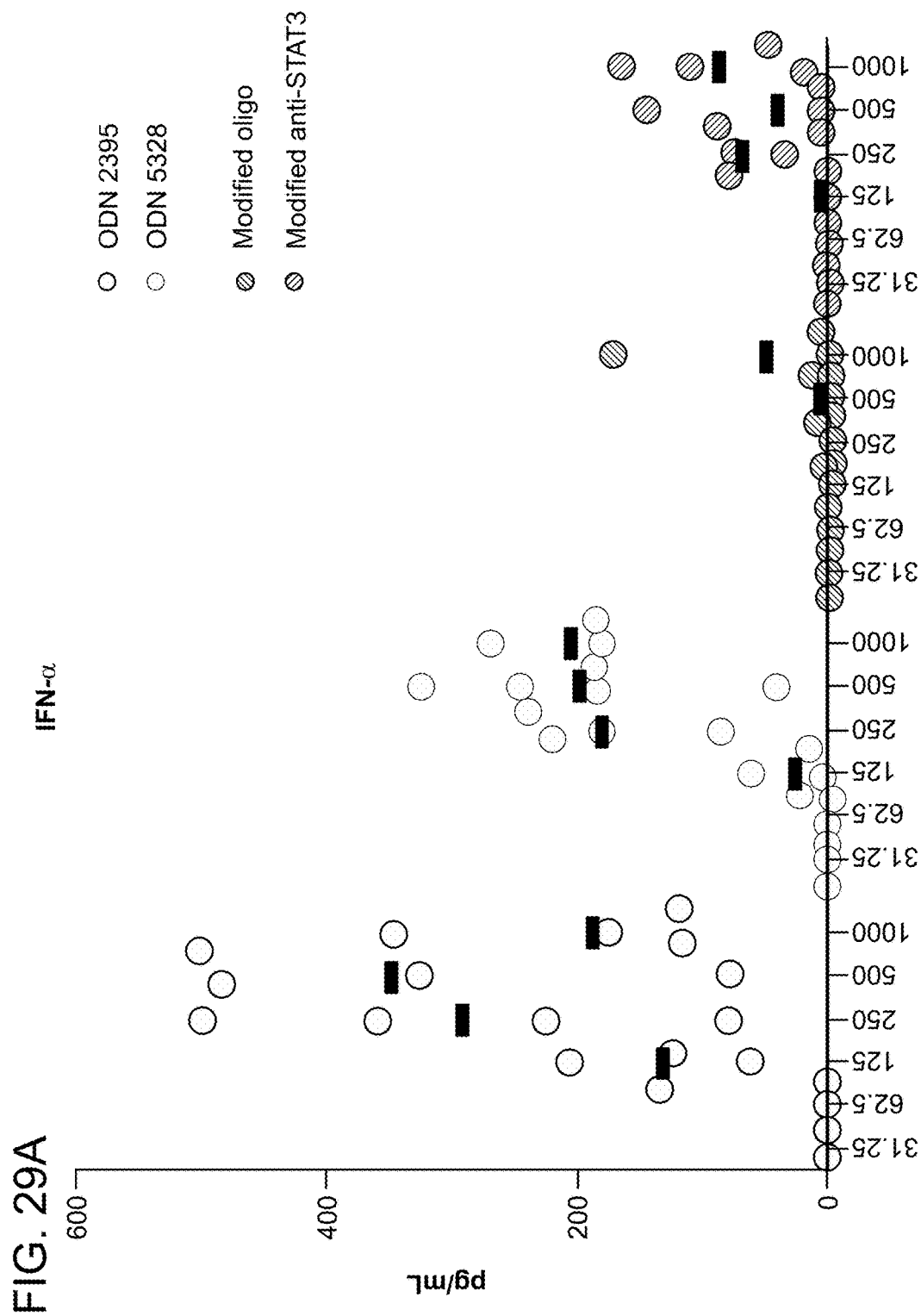

SEQUENCE LISTING

<160> NUMBER OF SEQ ID NOS: 19

<210> SEQ ID NO 1
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Gly Leu Gly Trp Gly Thr Tyr Phe Arg Leu Gly Asp
                100                 105                 110

Ala Phe Asp Ile Trp Gly Gln Gly Thr Met Val Thr Val Ser Ser
            115                 120                 125

<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Glu
                20                  25                  30

Gly Ala Ala Trp Leu Gln Gln His Gln Gly His Pro Pro Lys Leu Leu
            35                  40                  45

```
Ser Tyr Arg Asn Phe Asn Arg Pro Ser Gly Ile Ser Glu Arg Phe Ser
        50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Trp Asp Ser Ser Leu
                 85                  90                  95

Ser Ala Trp Val Phe Gly Gly Gly Thr Lys Leu Thr Val Leu
            100                 105                 110

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Tyr Val His Ser Phe Asp Ile Trp Gly Gln Gly Thr
            100                 105                 110

Met Val Thr Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Pro Val Leu Thr Gln Pro Pro Ser Ala Ser Ala Leu Leu Gly Ala
 1               5                  10                  15

Ser Ile Lys Leu Thr Cys Thr Leu Ser Ser Glu His Ser Thr Tyr Thr
            20                  25                  30

Val Glu Trp Tyr Gln Gln Arg Pro Gly Arg Ser Pro Gln Tyr Ile Met
        35                  40                  45

Asn Val Lys Ser Asp Gly Ser Tyr Asn Lys Gly Asp Gly Ile Pro Asp
    50                  55                  60

Arg Phe Met Gly Ser Ser Ser Gly Ala Asp Arg Tyr Leu Thr Phe Ser
 65                  70                  75                  80

Asn Leu Gln Ser Asp Asp Glu Ala Glu Tyr His Cys Gly Glu Ser His
                 85                  90                  95

Arg Ile Asp Gly Gln Val Gly Val Val Phe Gly Gly Gly Thr Lys Leu
            100                 105                 110
```

Thr Val Leu
        115

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Pro Ser Cys Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Pro Pro Cys Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Thr Gly Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Asn Pro Asn Ser Gly Gly Thr
1               5

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Asp Gly Gly Leu Gly Trp Gly Thr Tyr Phe Arg Leu Gly Asp
1               5                   10                  15

Ala Phe Asp Ile
            20

<210> SEQ ID NO 10

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Asn Asn Val Gly Asn Glu Gly
1               5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Asn Phe
1

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ala Trp Asp Ser Ser Leu Ser Ala Trp Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Tyr Thr Phe Thr Ser Tyr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Asn Pro Ser Gly Gly Ser Thr
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Ala Arg Ser Asp Tyr Val His Ser Phe Asp Ile
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Glu His Ser Thr Tyr Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Lys Ser Asp Gly Ser Tyr
1               5

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Glu Ser His Arg Ile Asp Gly Gln Val Gly Val Val
1               5                   10

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tccatgagct tcctgatgct                                              20
```

ANTIBODY THERAPEUTICS THAT BIND STAT3

RELATED APPLICATIONS

This application claims priority to U.S. Provisional Application No. 62/419,778, filed on Nov. 9, 2016, and U.S. Provisional Application No. 62/327,178, filed on Apr. 25, 2016, the entire contents of each of which are incorporated by reference in their entireties herein.

SEQUENCE LISTING

The instant application contains a Sequence Listing which has been submitted electronically in ASCII format and is hereby incorporated by reference in its entirety. Said ASCII copy, created on Apr. 18, 2017, is named 126036-06203_SL.txt and is 8,273 bytes in size.

BACKGROUND

Signal transduction proteins important in carcinogenesis and cancer progression present attractive targets for the development of novel anticancer therapeutics. The STAT (signal transducers and activators of transcription) family of proteins are DNA-binding proteins that play a dual role in signal transduction and activation of transcription. Six distinct members of the STAT family include STAT1, STAT2, STAT3, STAT4, STAT5, and STATE.

The activities of the STATs are modulated by various cytokines and mitogenic stimuli. Binding of a cytokine to its receptor results in the activation of Janus protein tyrosine kinases (JAKs) associated with these receptors. This phosphorylates STAT, resulting in translocation to the nucleus and transcriptional activation of STAT responsive genes. Phosphorylation on a specific tyrosine residue on the STATs results in their activation, resulting in the formation of homodimers and/or heterodimers of STAT which bind to specific gene promoter sequences. Events mediated by cytokines through STAT activation include cell proliferation and differentiation and prevention of apoptosis.

STAT3 is expressed in most cell types (Zhong et al., *Proc. Natl. Acad. Sci. USA*, 1994, 91, 4806-4810), and induces the expression of genes involved in response to tissue injury and inflammation. STAT3 has been shown to prevent apoptosis through the expression of bc1-2 (Fukada et al., *Immunity*, 1996, 5, 449-460). STAT3 is a master regulator of genes controlling cell proliferation, survival, migration and immune suppression. Aberrant expression of or constitutive expression of STAT3 has been associated with a number of disease processes. Constitutive activation of STAT3 has been found in a wide variety of cancers and STAT3 has been found to be persistently activated in tumor cells as well as non-transformed cells in the tumor microenvironment.

SUMMARY OF THE INVENTION

The invention includes antibodies, including isolated human antibodies, that bind to STAT3, including human STAT3.

In a first aspect, the invention features an isolated anti-Signal Transducer and Activator of Transcription 3 (STAT3) antibody, or an antigen-binding fragment thereof, comprising a heavy chain variable domain comprising a CDR3 domain comprising an amino acid sequence as set forth in SEQ ID NO: 9, a CDR2 domain comprising an amino acid sequence as set forth in SEQ ID NO: 8, and a CDR1 domain comprising an amino acid sequence as set forth in SEQ ID NO: 7; and a light chain variable domain comprising a CDR3 domain comprising an amino acid sequence as set forth in SEQ ID NO: 12, a CDR2 domain comprising an amino acid sequence as set forth in SEQ ID NO: 11, and a CDR1 domain comprising an amino acid sequence as set forth in SEQ ID NO: 10.

In one embodiment, the heavy chain variable domain comprises an amino acid sequence as set forth in SEQ ID NO: 1, and the light chain variable domain comprises an amino acid sequence as set forth in SEQ ID NO: 2.

In another aspect, the present invention features an isolated anti-STAT3 antibody, or an antigen-binding fragment thereof, comprising a heavy chain variable domain comprising a CDR3 domain comprising an amino acid sequence as set forth in SEQ ID NO: 15, a CDR2 domain comprising an amino acid sequence as set forth in SEQ ID NO: 14, and a CDR1 domain comprising an amino acid sequence as set forth in SEQ ID NO: 13; and light chain variable domain comprising a CDR3 domain comprising an amino acid sequence as set forth in SEQ ID NO: 18, a CDR2 domain comprising an amino acid sequence as set forth in SEQ ID NO: 17, and a CDR1 domain comprising an amino acid sequence as set forth in SEQ ID NO: 16.

In one embodiment, the heavy chain variable domain comprises an amino acid sequence as set forth in SEQ ID NO: 3, and the light chain variable domain comprises an amino acid sequence as set forth in SEQ ID NO: 4.

In another aspect, the present invention features an isolated anti-STAT3 antibody, or antigen-binding fragment thereof, comprising a heavy chain variable domain comprising an amino acid sequence that is at least 95% identical to an amino acid sequence selected from SEQ ID NO: 1 or SEQ ID NO: 3; and a light chain variable domain comprising an amino acid sequence that is at least 95% identical to an amino acid sequence selected from SEQ ID NO: 2 or SEQ ID NO: 4.

In one embodiment, the heavy chain variable domain comprises an amino acid sequence that is at least 96% identical to an amino acid sequence selected from SEQ ID NO: 1 or SEQ ID NO: 3; and the light chain variable domain comprises an amino acid sequence that is at least 96% identical to an amino acid sequence selected from SEQ ID NO: 2 or SEQ ID NO: 4.

In another embodiment, the heavy chain variable domain comprises an amino acid sequence that is at least 97% identical to an amino acid sequence selected from SEQ ID NO: 1 or SEQ ID NO: 3; and the light chain variable domain comprises an amino acid sequence that is at least 97% identical to an amino acid sequence selected from SEQ ID NO: 2 or SEQ ID NO: 4.

In a further embodiment, the heavy chain variable domain comprises an amino acid sequence that is at least 98% identical to an amino acid sequence selected from SEQ ID NO: 1 or SEQ ID NO: 3; and the light chain variable domain comprises an amino acid sequence that is at least 98% identical to an amino acid sequence selected from SEQ ID NO: 2 or SEQ ID NO: 4.

In another further embodiment, the heavy chain variable domain comprises an amino acid sequence that is at least 99% identical to an amino acid sequence selected from SEQ ID NO: 1 or SEQ ID NO: 3; and the light chain variable domain comprises an amino acid sequence that is at least 99% identical to an amino acid sequence selected from SEQ ID NO: 2 or SEQ ID NO: 4.

In one embodiment, the heavy chain variable domain comprises an amino acid sequence selected from SEQ ID NO: 1 or SEQ ID NO: 3; and the light chain variable domain comprises an amino acid sequence selected from SEQ ID NO: 2 or SEQ ID NO: 4.

In one embodiment, the antibody conjugate is the structure shown in FIG. 1B. FIG. 1B is a drawing of an exemplary antibody conjugate of the present invention, Compound 901a, where the antibody ($A_T$) is ST3G12 and one $R^1$ in FIG. 1A is an alkylfluorophore moiety.

In one embodiment, the antibody conjugate is the structure shown in FIG. 1C. FIG. 1C is a drawing of an exemplary antibody conjugate of the present invention, Compound 901, where the antibody ($A_T$) is ST3G12 and each $R^1$ in FIG. 1A is hydrogen.

In another embodiment of any one of the above aspects, the anti-STAT3 antibody, or antigen-binding fragment thereof, has a $K_D$ of at least $1\times10^{-6}$ M.

In another embodiment of any one of the above aspects, the anti-STAT3 antibody, or antigen-binding fragment thereof, has a $K_D$ of $1\times10^{-6}$ M or less.

In another embodiment of any one of the above aspects, the anti-STAT3 antibody, or antigen-binding fragment thereof, is a human antibody.

In a further embodiment of any one of the above aspects, the anti-STAT3 antibody, or antigen-binding fragment thereof, is an IgG1, IgG2, IgG3 or an IgG4. In particular embodiments, the antibody is an IgG1 or an IgG4 isotype.

In another further embodiment of any one of the above aspects, the anti-STAT3 antibody, or antigen-binding fragment thereof, is a Fab fragment or an scFv.

In certain embodiments, the anti-STAT3 antibody is an intact antibody comprising the CDR or variable amino acid sequences described herein.

In one embodiment of any one of the above aspects, the anti-STAT3 antibody, or an antigen-binding fragment thereof, is conjugated to an intracellular delivery compound.

In one embodiment, the invention features a method for treating a subject having cancer, the method comprising administering an effective amount of the anti-STAT3 antibody, or antigen-binding fragment thereof, of any one of the above aspects to the subject.

In a further embodiment, the cancer is a solid tumor.

In another further embodiment, the cancer is selected from the group consisting of melanoma, glioma, medulloblastoma, renal cell carcinoma, pancreatic adenocarcinoma, ovarian carcinoma, rhabdomyosarcoma, osteosarcoma, glioblastoma, breast, pancreas, ovarian, prostate, lung, liver, colon, colorectal, gastric, head, neck, and kidney. In a further related embodiment, the cancer is a hematological cancer. In related embodiments, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia and large granular lymphocyte leukemia.

In another embodiment, the invention features a method for treating a subject having an autoimmune disease, the method comprising administering an effective amount of the anti-STAT3 antibody, or antigen-binding fragment thereof, of any one of the above aspects to the subject.

In a further embodiment, the autoimmune disease is selected from multiple sclerosis, Crohn's disease, certain bacterially induced colitis, arthritis, lupus, diabetes, asthma, inflammatory bowel disease, scleroderma, and vasculitis.

In another embodiment, the invention features pharmaceutical compositions comprising the anti-STAT3 antibody, or antibody fragment of any one of the above aspects, and a pharmaceutically acceptable carrier.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1B discloses SEQ ID NO: 19 (tccatgagcttcctgatgct), which corresponds to the bases on the oligonucleotide of the structure.

FIG. 1C discloses SEQ ID NO: 19 (tccatgagcttcctgatgct), which corresponds to the bases on the oligonucleotide of the structure.

Figure 6:
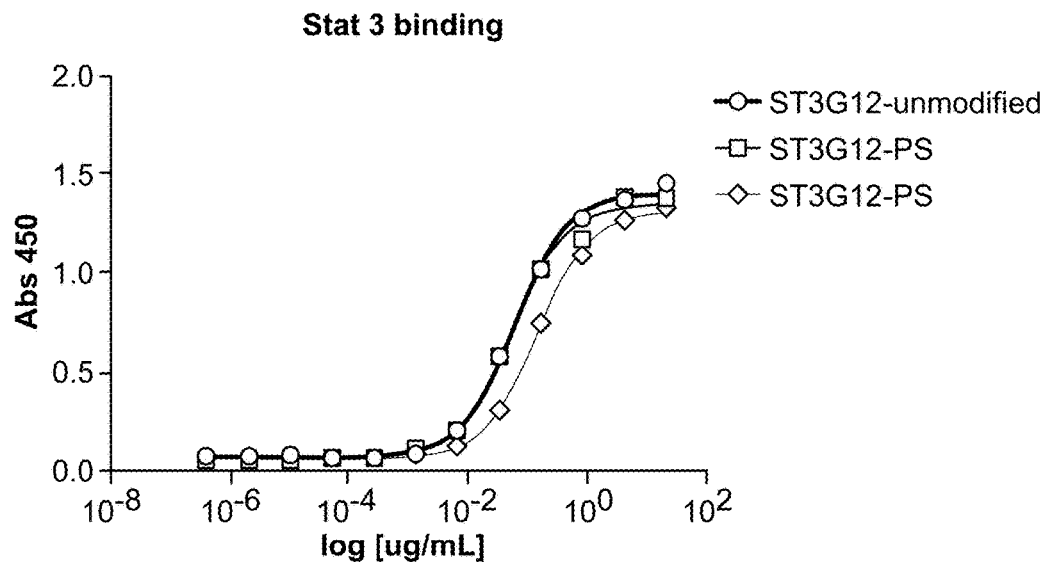

FIG. 6 is a graph that shows the results of an ELISA assay used to assess the binding of the anti-STAT3 ST3G12 antibodies that were unmodified ("ST3G12-unmodified") and PS modified ST3G12 antibody conjugates ("ST3G12-PS") to recombinant human STAT3 proteins.

Figure 7A:
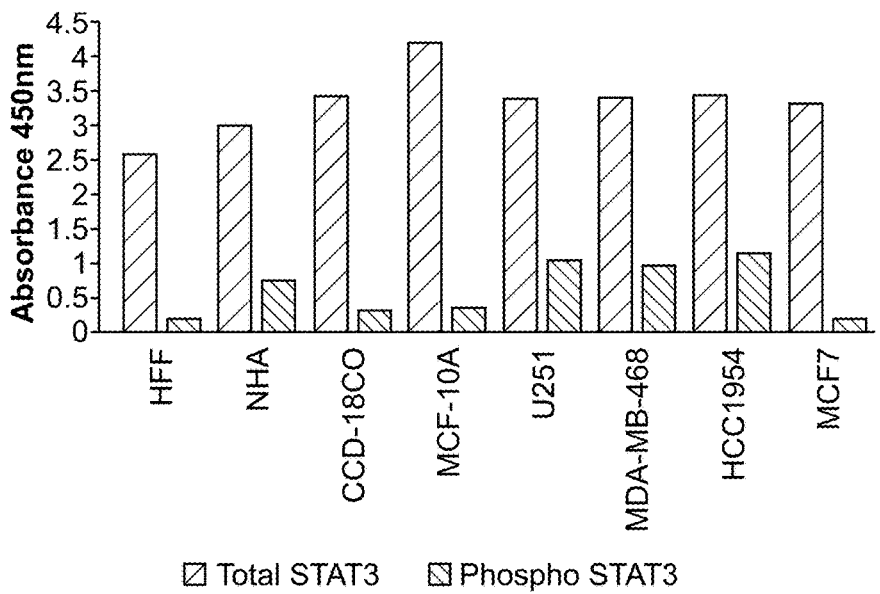

FIG. 7A is a graph that shows the results of an ELISA assay carried out to determine the total level of STAT3 and the level of phosphorylated STAT3 (phospho-STAT3) in human foreskin fibroblast (HFF), normal human astrocytes (NHA), normal colon fibroblasts (CCD-18CO), normal breast epithelial cells (MCF-10A), glioblastoma (U251), triple negative breast cancer (MDA-MB-468), triple negative breast cancer (HCC1954) and ER+ breast cancer (MCF-7). Levels of phosphorylated STAT3 were determined by ELISA using an antibody to phospo-STAT3. Controls used were primary antibody alone, secondary antibody alone and an isotype matched control IgG.

Figure 7B:
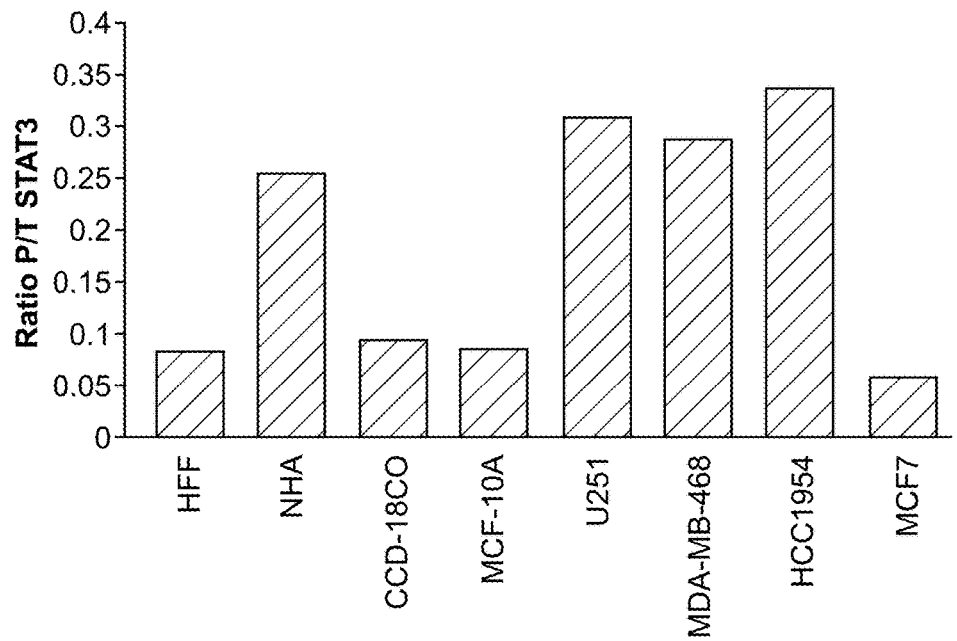

FIG. 7B is a graph that shows the ratio of phosphorylated to total STAT3 (ratio P/T STAT3) in the cells tested in FIG. 7A.

Figure 7C:
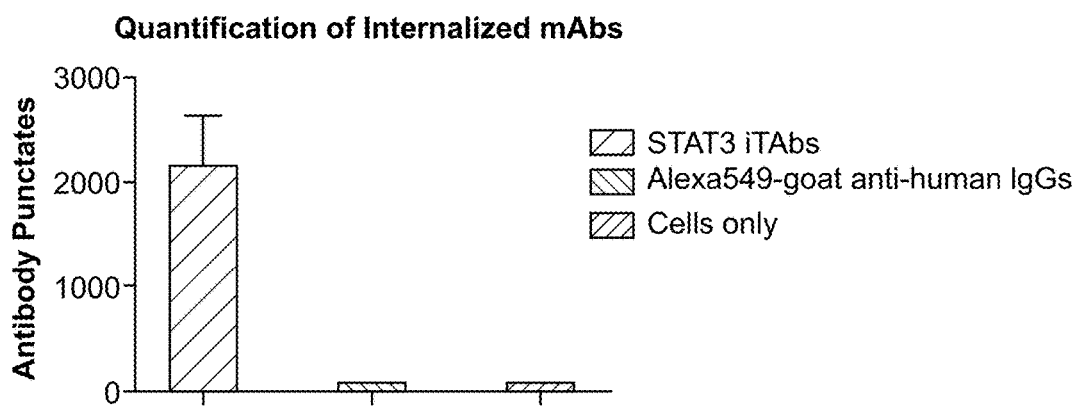

FIG. 7C is a graph that shows quantification of internalized anti-STAT3 antibody conjugate, "STAT3 iTAbs", (compound 901) by the number of antibody punctates in HeLa cells. As a control, Alexa 549-goat anti-human IgGs were used or cells alone (no treatment).

Figure 8A:
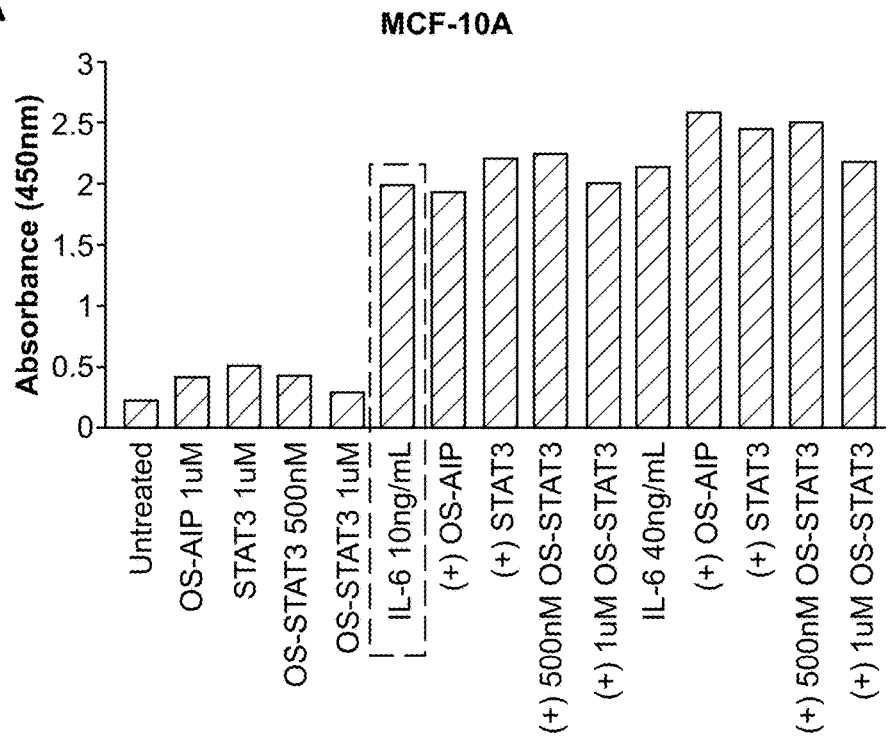

FIG. 8A is a graph that shows the results of experiments to determine the effect of modified STAT3 antibody conjugate (ST3G12-PS) on STAT3 phosphorylation in MCF-10A cells. Cells were pre-treated overnight with antibody, and then stimulated with various concentrations of IL-6 (10 ng/ml or 40 ng/ml) for 20 minutes, to activate STAT3. Cells were then lysed and the protein lysates were subjected to ELISA to determine the phosphorylation status. "OS-AIP" refers to an oligosaccharide conjugated anti-bacterial AIP (staphylococcal auto-inducing peptide) antibody used as a control. "STAT3" refers to anti-STAT3 ST3G12 antibodies. "OS-STAT3" refers to anti-STAT3 ST3G12 antibody conjugates (compound 901). IL-6 is a STAT3 activator. Bars with the designation "(+)" indicates cells that were treated with IL-6 (10 ng/ml or 40 ng/ml) and either anti-STATe ST3G12 antibodies ("(+) STAT3") or anti-STAT3 ST3G12 antibody conjugates (compound 901) "(+) OS-STAT3") at the indicated concentrations.

Figure 8B:
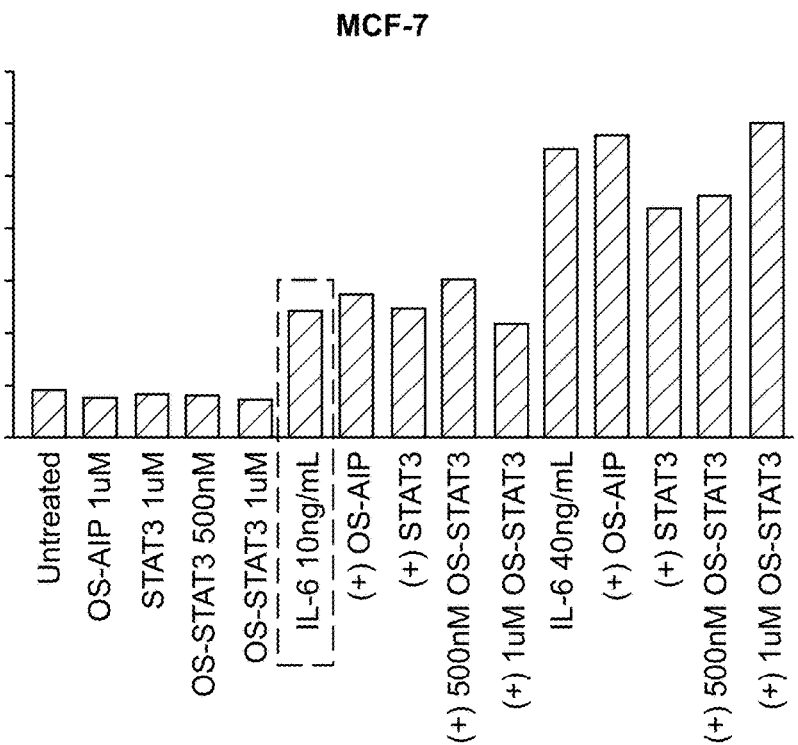

FIG. 8B is a graph that shows the results of experiments to determine the effect of ST3G12 and ST3G12-PS antibody conjugates on STAT3 phosphorylation in MCF7 cells. The experimental procedure was the same as described in FIG. 8A.

Figure 9A:
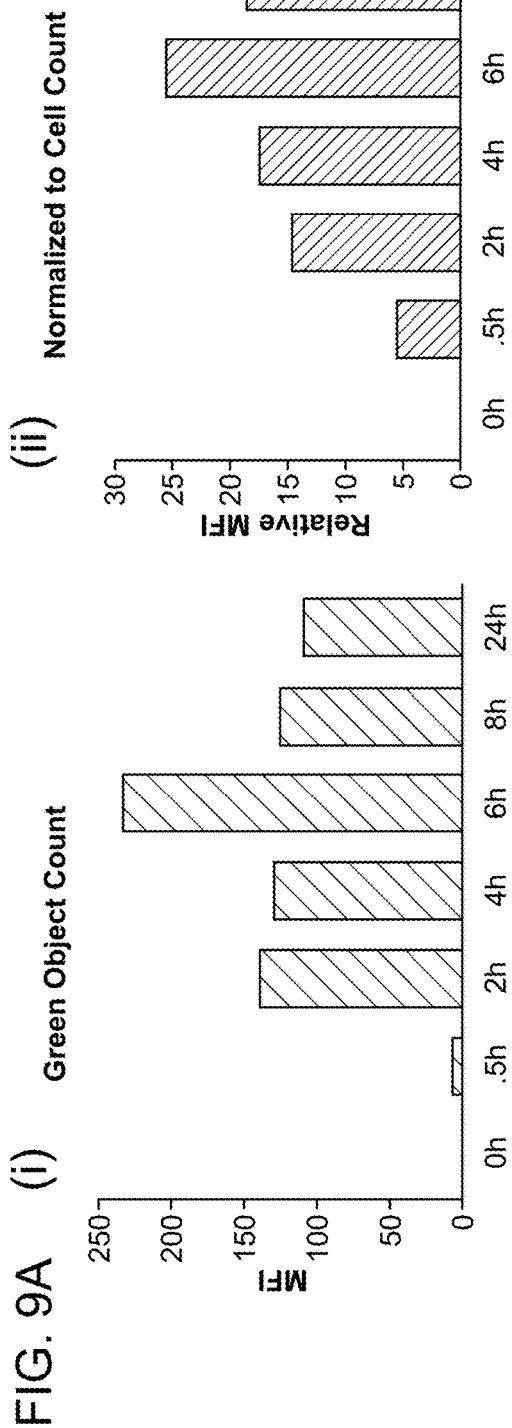

FIG. 9A is a graph that shows the results of a time course experiment showing ST3G12-PS antibody accumulation in MDA-MB-468 cells. Cells were seeded in 96 well plates overnight. 20 ug/ml of anti-STAT3 antibody ST3G12-PS-Alexa 488 was added for the indicated duration of 0.5, 2, 4, 6, 8 and 24 hours, and cells were fixed and imaged. Green object count refers to the number of green fluorescing cells. FIG. 9 panel (i) and panel (ii) show that accumulation of the antibody increased as time increases. FIG. 9A, panel (ii) shows the data from FIG. 9A, panel (i) normalized to cell count. The results show the prolonged accumulation of ST3G12-PS antibody in tumor cells.

Figure 9B:
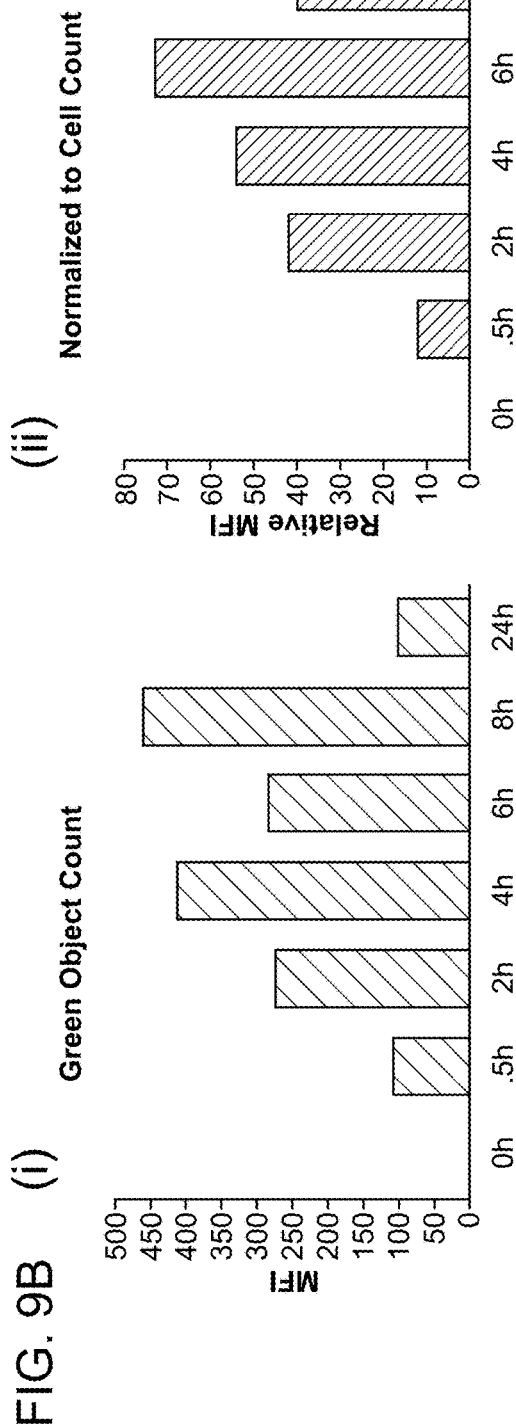

FIG. 9B is a graph that shows the same experiments described in FIG. 9A, performed in MCF-10A cells. The results show that accumulation of ST3G12-PS antibody decreased after 6 hours.

Figure 9C:
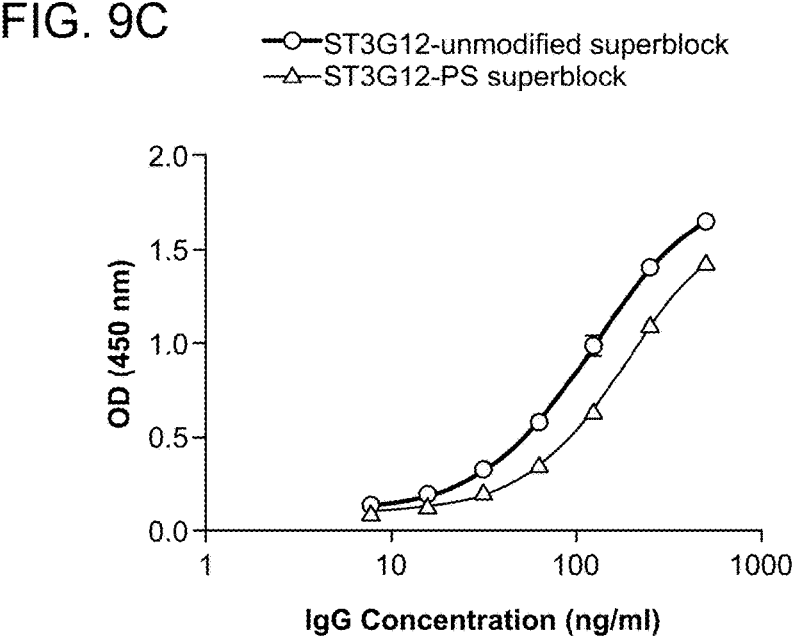

FIG. 9C is a graph that shows the results of an ELISA experiment carried out to show that modification of the ST3G12 antibody with the PS oligo did not affect its binding affinity to human IgG. "ST3G12-unmodified" refers to the unmodified ST3G12 anti-STAT3 antibody and "ST3G12-PS" refers to the modified ST3G12 anti-STAT3 antibody conjugates. Superblock refers to the blocking buffer used in the ELISA assay.

Figure 9D:
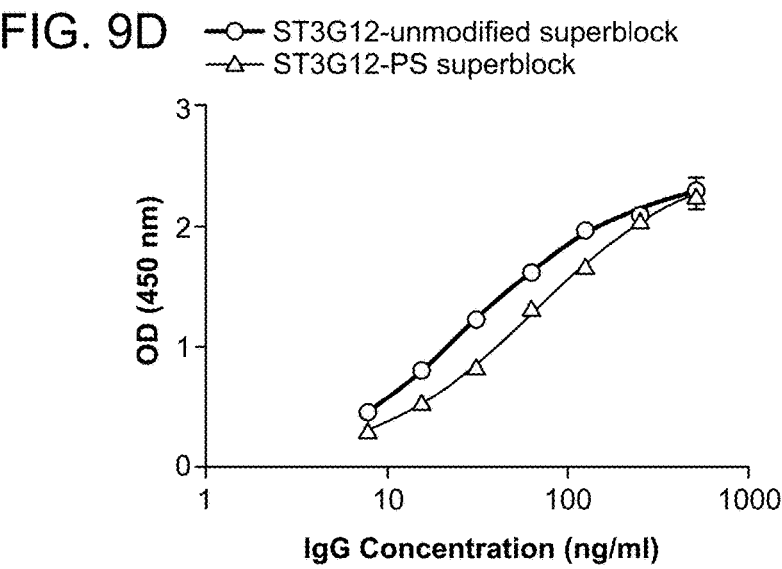

FIG. 9D is a graph that shows the results of an ELISA experiment carried out to show that modification of the ST3G12 antibody did not affect its binding affinity. "ST3G12-unmodified" refers to the unmodified ST3G12 anti-STAT3 antibody and "ST3G12-PS" refers to the modified ST3G12 anti-STAT3 antibody conjugates. Superblock refers to the blocking buffer used in the ELISA assay.

Figure 10A:
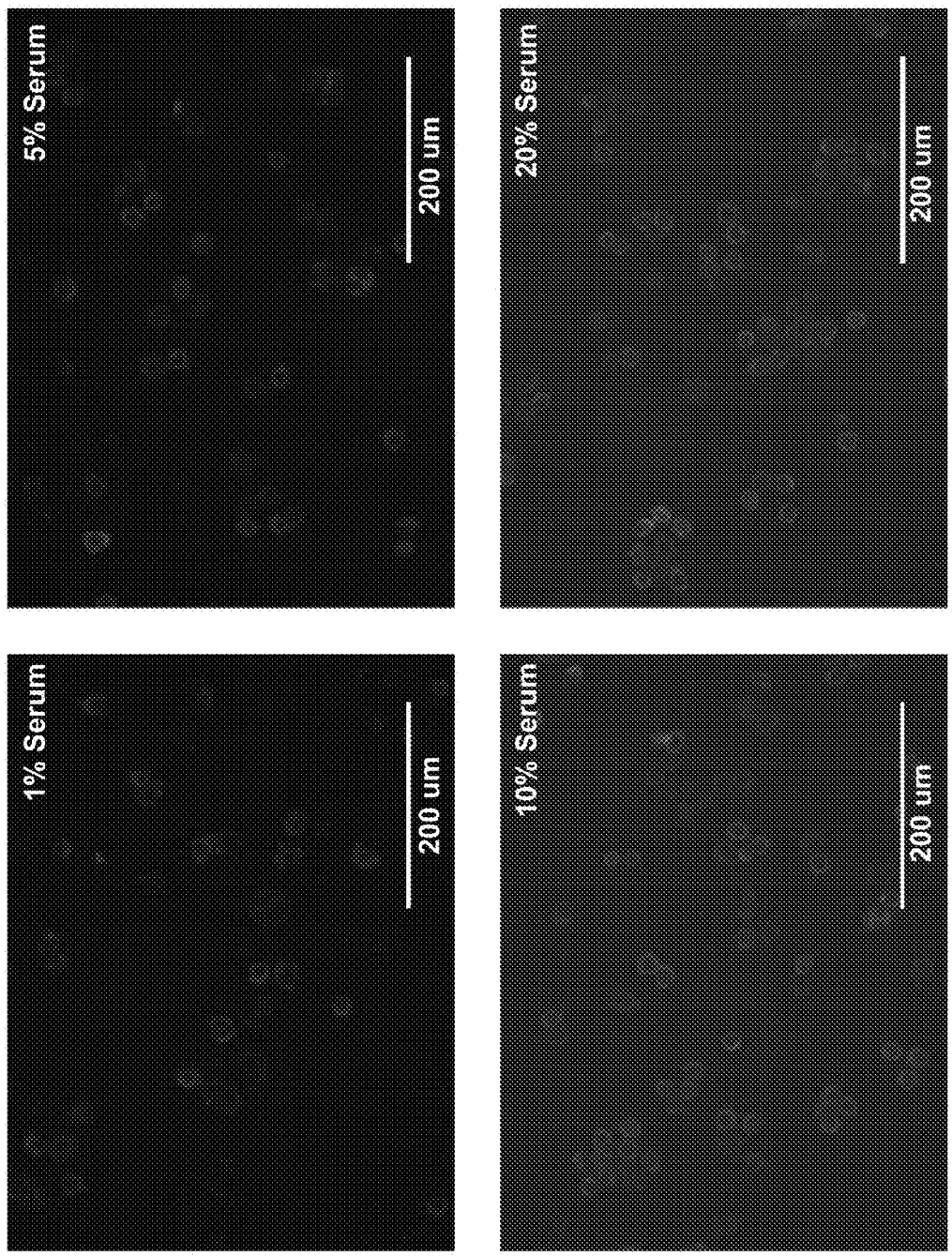

FIG. 10A shows immunofluorescent microscopic images from experiments in which MDA-MB-468 triple negative breast cancer cells were treated with 10 ug/ml of the anti-STAT3 conjugate ST3G12-PS in increasing proportions of human serum (1%, 5%, 10% and 20%). Cells were then fixed, permeabilized and stained with anti-human IgG Alexa 546. Red fluorescence shows accumulation of the antibody, where increased accumulation was seen with increased concentrations of serum.

Figure 10B:
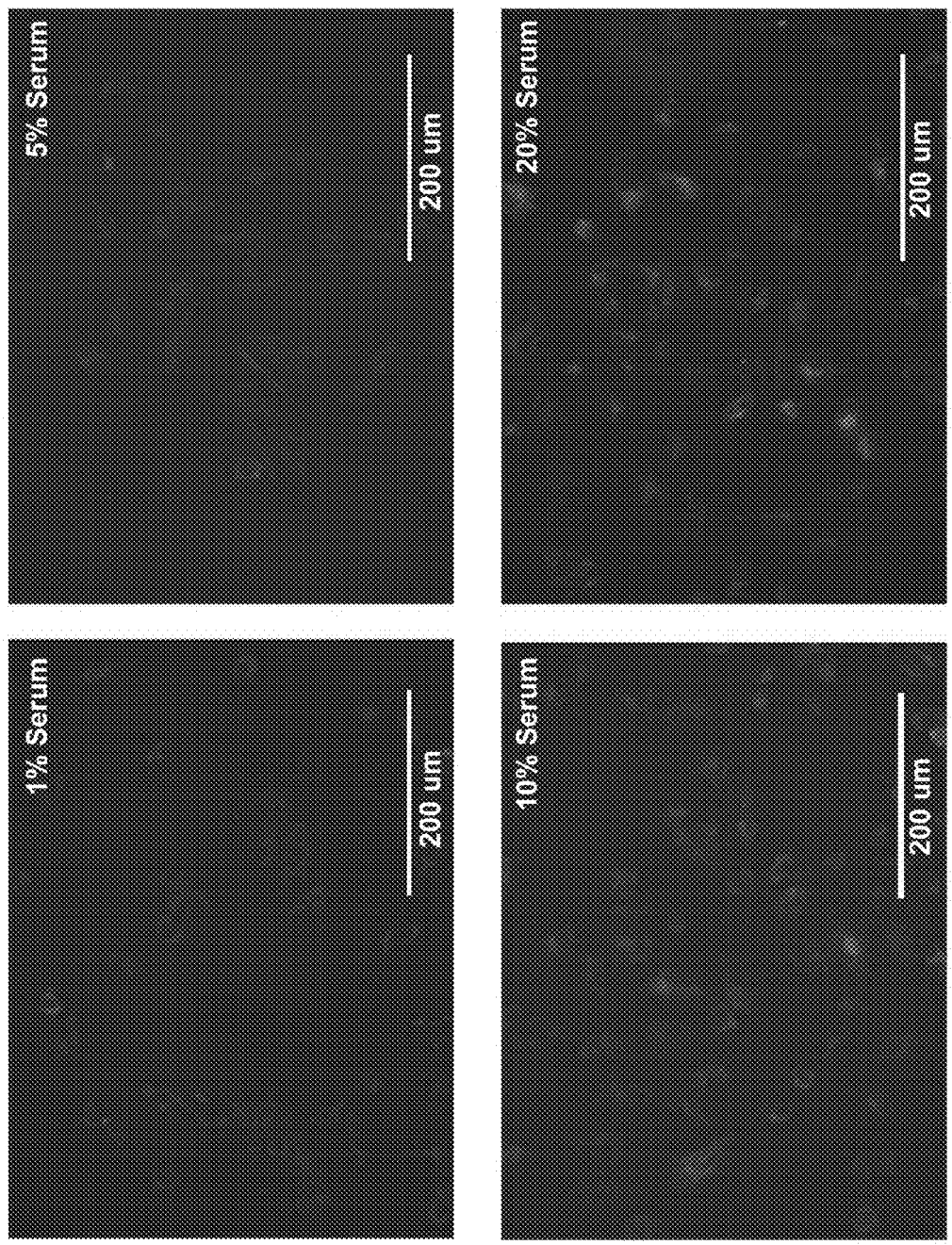

FIG. 10B is an immunofluorescent microscopic image of ST3G12-PS antibody conjugate that has accumulated in U251 cells. Red fluorescence shows accumulation of the antibody, where increased accumulation was seen with increased concentrations of serum.

FIG. 10C is an immunofluorescent microscopic image of ST3G12-PS antibody conjugate uptake in MCF10A human normal breast epithelial cells. Red fluorescence shows accumulation of the antibody, where increased accumulation was seen with increased concentrations of serum.

Figure 10D:
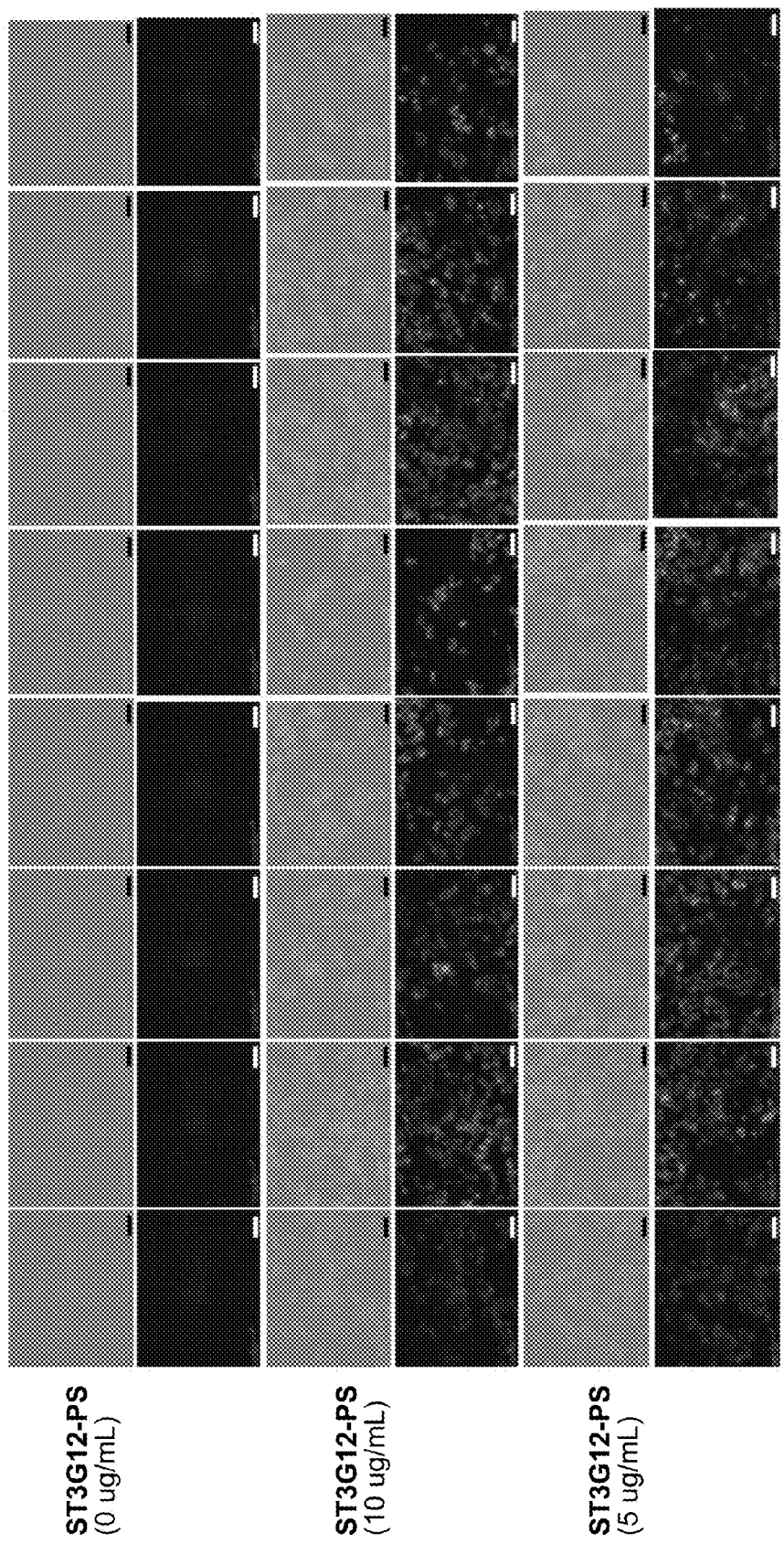

FIG. 10D is a confocal microscopic image of ST3G12-PS antibody conjugate (compound 901a) in MDA-MB-468 human breast cancer cells. ST3G12-PS was tested at 0 μg/ml, 10 μg/ml and 5 μg/ml. As shown in FIG. 10D, at concentrations of 5 μg/ml, and 10 μg/ml, ST3G12-PS accumulated in the cells.

Figure 10E:
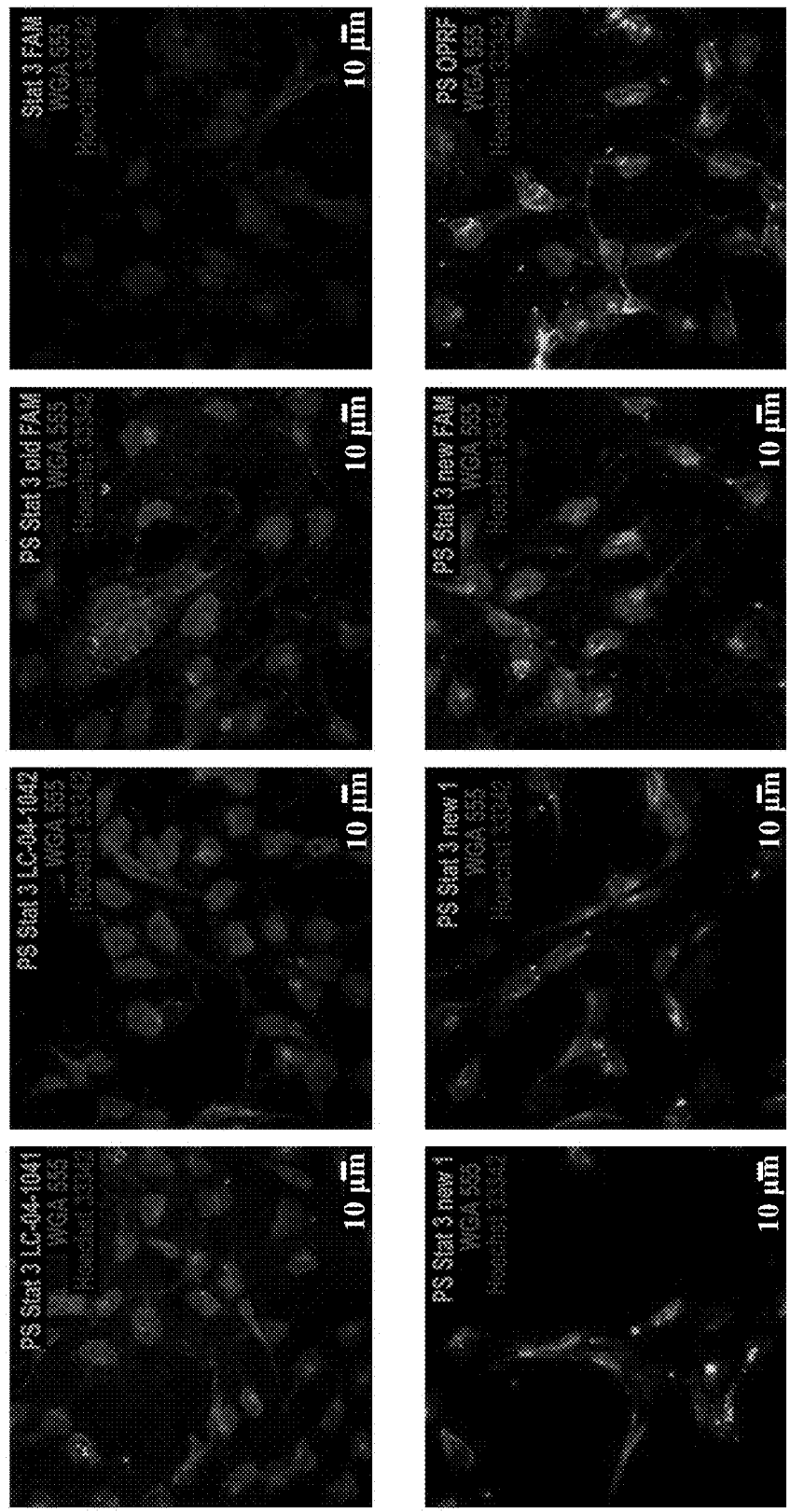

FIG. 10E is a confocal microscopic image of ST3G12 and ST3G12-PS antibody conjugate internalization in U251 cells. Nuclei were stained with Hoescht dye and are shown in blue. Wheat Germ Agglutinin (WGA), Alexa Fluor 555 Conjugate is shown in red. PS-ST3G12, ST3G12 or control PS-OPRF are shown in green. The results shown in FIG. 10E show that the ST3G12 antibody conjugate (ST3G12-PS) was able to penetrate the cells.

Figure 11A:
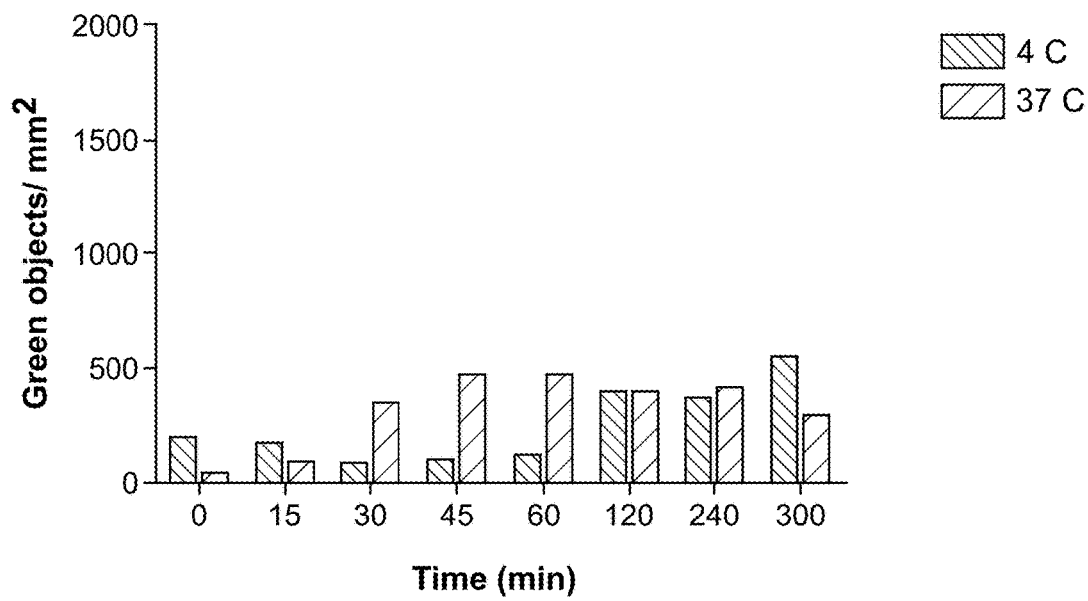

FIG. 11A is a graph that shows the effect of temperature on internalization of ST3G12-PS antibody conjugate in U251 cells. U251 cells were incubated with PS-ST3G12 with an Alexa flour NHS 488 label at a concentration of 10 ug/ml. The results are counted as the number of green objects, corresponding to the number of cells that internalized the antibody conjugate, over time, at 4° C. and 37° C.

Figure 11B:
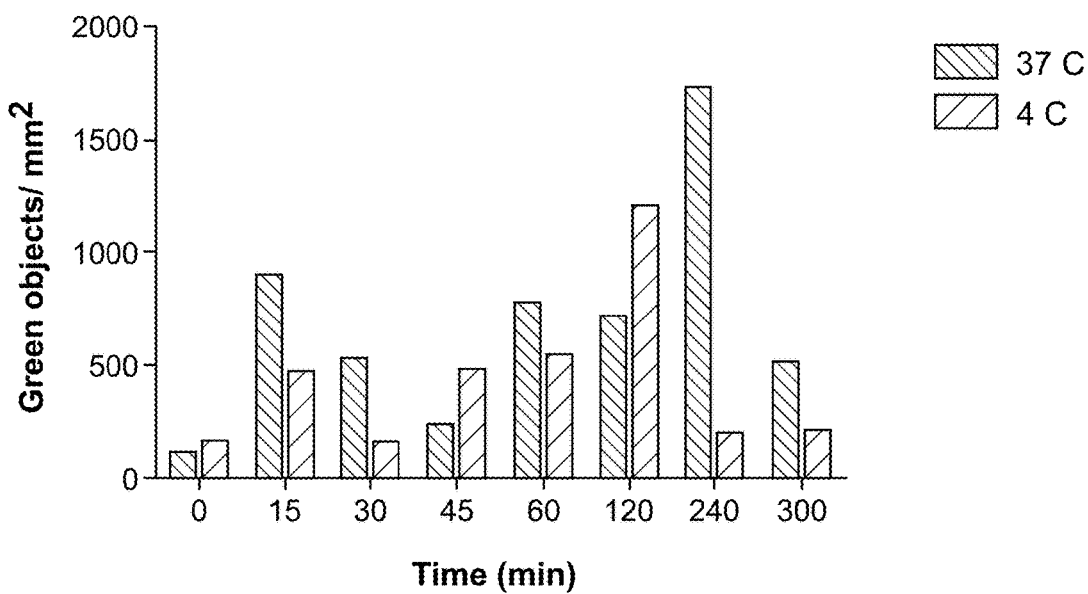

FIG. 11B is a graph that shows the effect of temperature on internalization of ST3G12-PS antibody conjugate in MDA-MB-468 cells. MDA-MB-468 cells were incubated with ST3G12-PS with an Alexa flour NHS 488 label at a concentration of 10 ug/ml. The results are counted as the number of green objects, corresponding to the number of cells that internalized the antibody conjugate, over time, at 4° C. and 37° C.

Figure 12A:
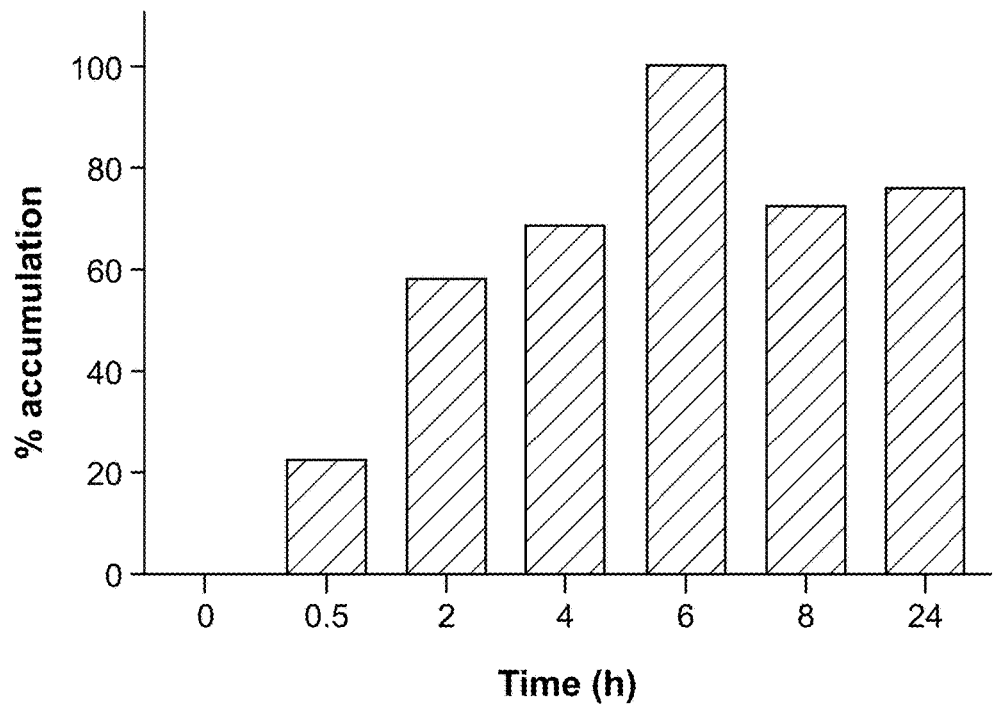

FIG. 12A is a graph that shows the results of a time course analysis that was carried out to determine the cellular uptake of ST3G12-PS antibody conjugate in MDA-MB-468 cells. ST3G12-PS labeled with Alexa 488 was added to the cells for the following durations: 0.5 hours, 2 hours, 4 hours, 6 hours, 8 hours and 24 hours. Cells were then fixed and imaged using Incucyte. Accumulation of the antibody in cells appeared to peak at 6 hours.

Figure 12B:
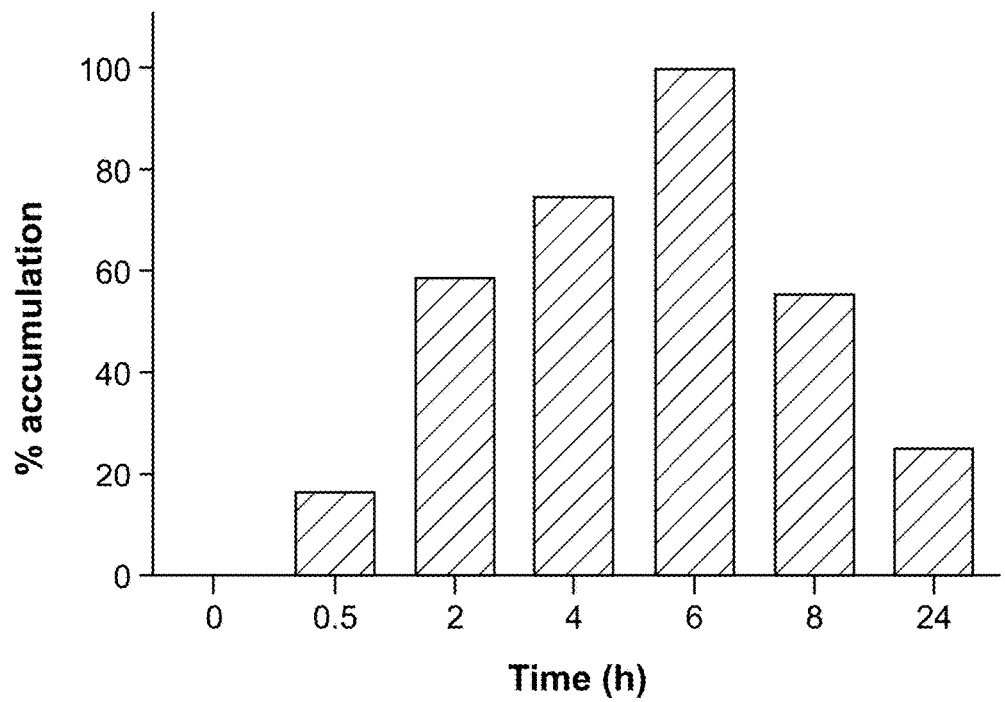

FIG. 12B is a graph that shows the results of a time course analysis that was carried out to determine the cellular uptake of ST3G12-PS antibody conjugate in MCF-10A cells. ST3G12-PS labeled with Alexa 488 was added to the cells for the following durations: 0.5 hours, 2 hours, 4 hours, 6 hours, 8 hours and 24 hours. Cells were then fixed and imaged using Incucyte. Accumulation of the ST3G12-PS appeared to peak at 6 hours.

Figure 13:
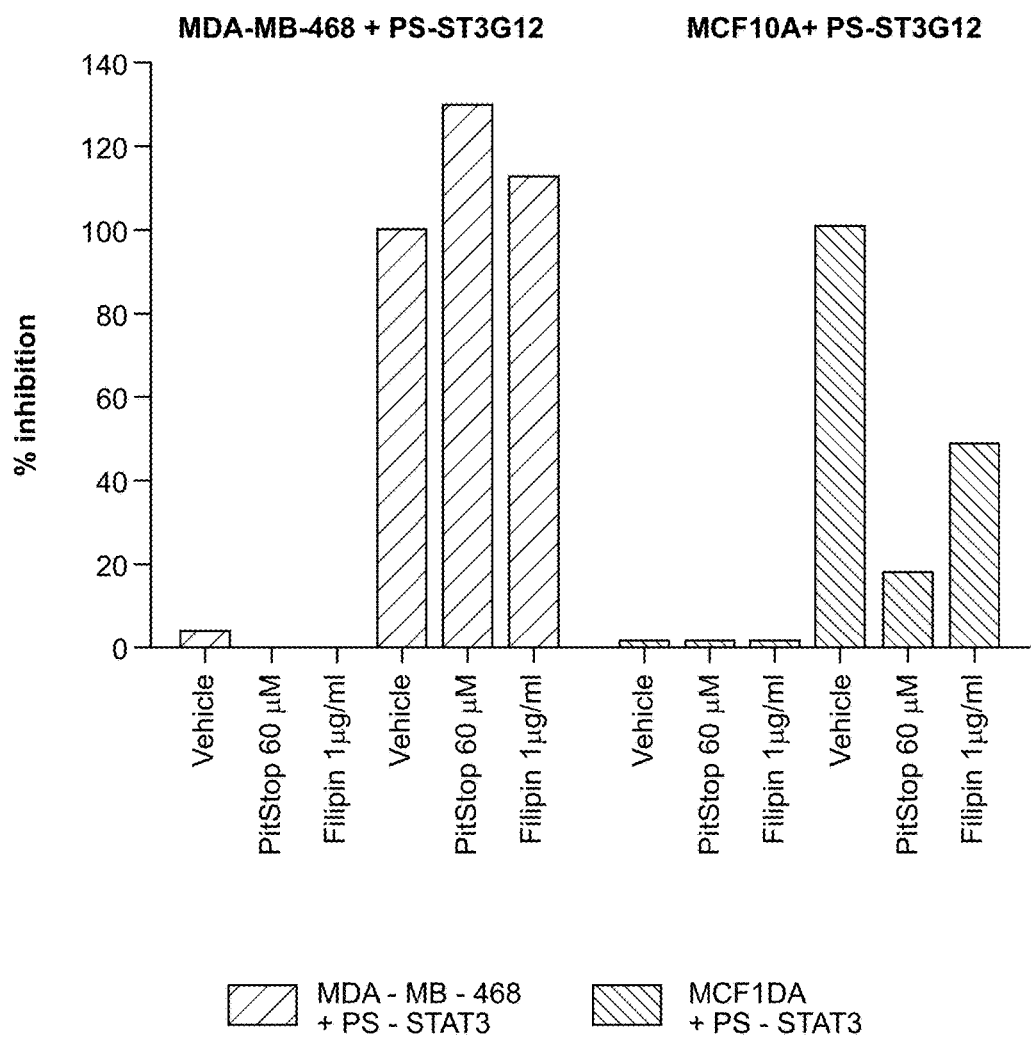

FIG. 13 is a graph that shows that ST3G12-PS enters MDA-MB-468 (STAT3 high) tumor cells using endocytosis independent mechanism. Normal breast epithelial cell line, MCF-10A (STAT3 low), was also tested. Vehicle alone was used as a control. Results were measured as percent inhibition of antibody entry into cells.

FIGS. 14 (i) and (ii) are graphs that shows the effects of the clathrin inhibitor Pitstop2 (PS2; 30 uM or 60 uM) or the caveolin inhibitor filipin (0.5 ug/ml or 1.0 ug/ml) on ST3G12-PS mediated uptake in MCF-10A cells. As shown in FIG. 14 panel (i), treatment with the clathrin inhibitor PS2 at concentrations of 30 uM and 60 uM inhibited ST3G12-PS uptake, while treatment with the caveolin inhibitor, filipin, had little effect at a concentration of 0.5 ug/ml, and a greater effect at 1.0 ug/ml. "Green object count" refers to cells that have internalized ST3G12-PS and are detected by their green fluorescence. FIG. 14 panel (ii) shows the data from FIG. 14 panel (i) normalized to cell count.

FIGS. 15(i) and (ii) are graphs that shows the results of the same experiments done in FIGS. 14 (i) and (ii), in MDA-MB-468 breast carcinoma cells.

Figure 16A:
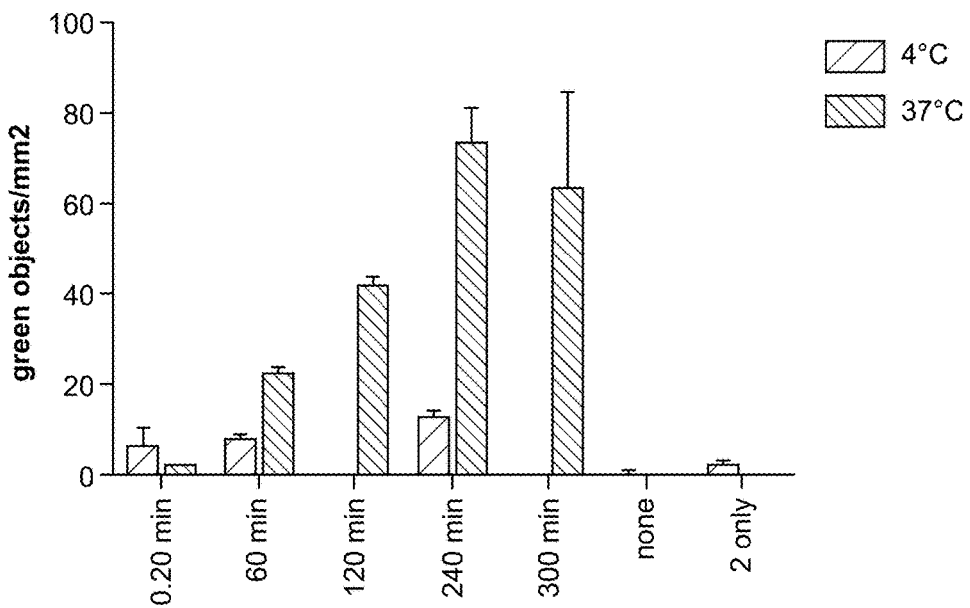

FIG. 16A is a graph that shows the results of experiments that were carried out to determine if the entrance of ST3G12-PS antibody conjugate was dependent on temperature. FIG. 16A shows an inhibition of ST3G12-PS at 4° C. as determined by number of green objects/mm$^2$. The number of green objects refers to cells which have internalized ST3G12-PS. As shown in FIG. 16A, as time increased, the green object count did not increase. For ST3G12-PS tested at 37° C., the green object count increased until 240 minutes. After 240 minutes, there was either a taper or a plateau.

Figure 16B:
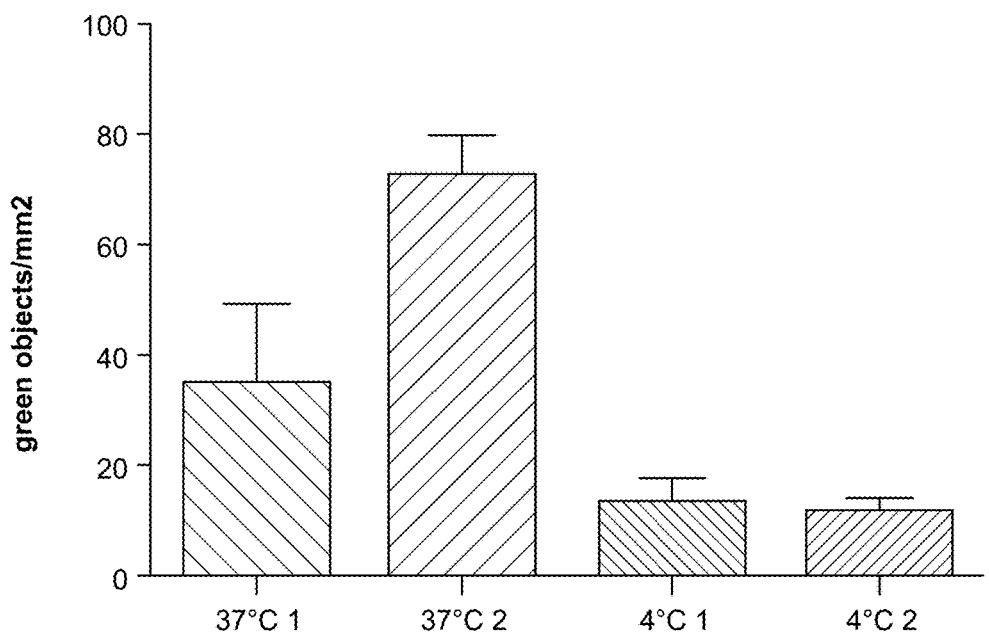

FIG. 16B is a graph that shows the results of experiments that were carried out to determine if the entrance of ST3G12-PS antibody conjugate was dependent on temperature. FIG. 16B compares the 240 minute time point from the experiment described in FIG. 16A ("37° C. 1" and "4° C. 1") with a second identical experiment at the 240 minute time point ("37° C. 2" and 4° C. 2")). The signal at 4° C. remained about the same, but there was a large boost in 37° C. signal.

Figure 17A:
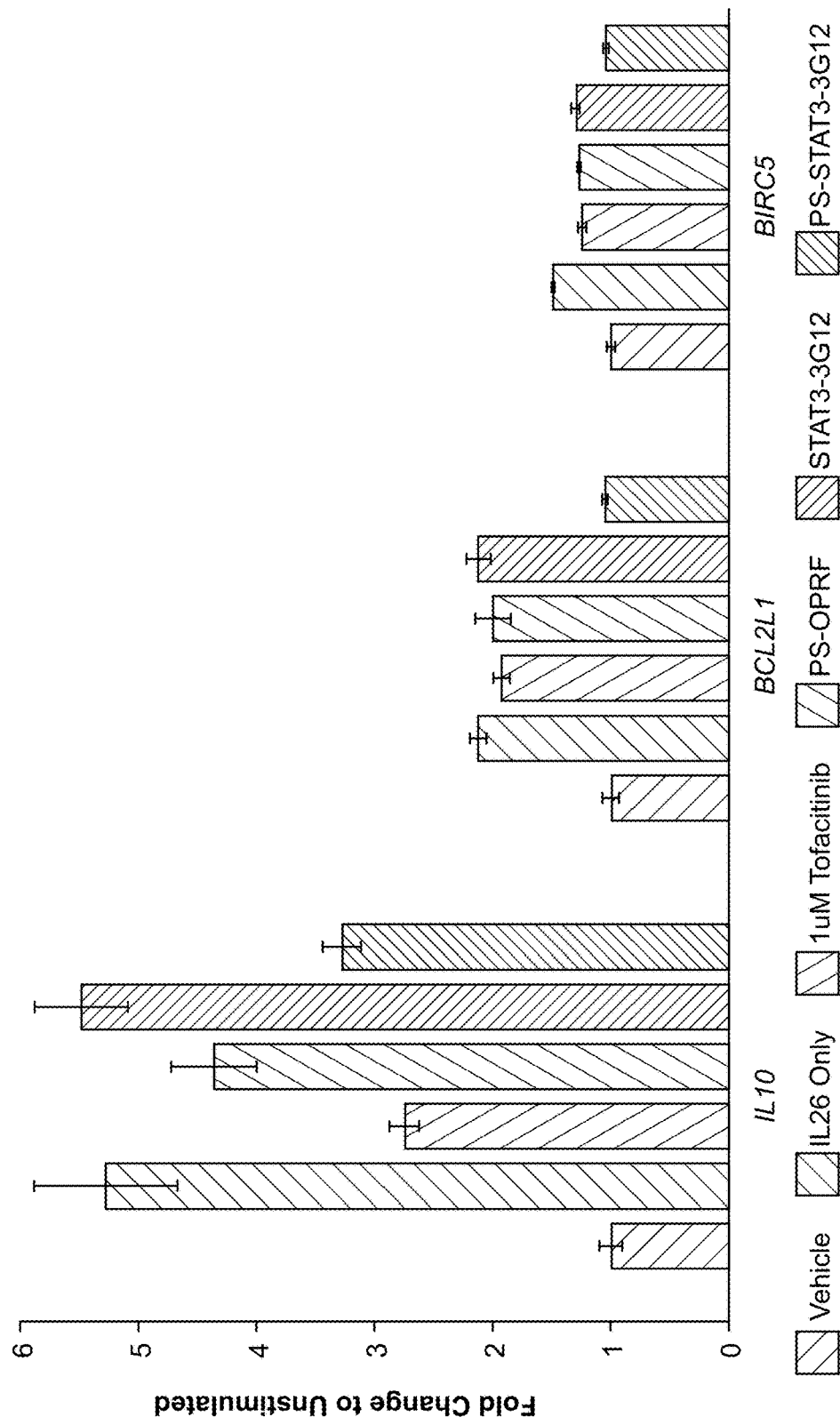

FIG. 17A is a graph that shows the results of experiments that were carried out to test whether ST3G12-PS can block mRNA expression of IL-26 induced IL-10 cytokine and anti-apoptotic genes BCL2L1 and BIRC5. Cells were pre-incubated with 50 ug/mL PS-OPRF (oligo conjugated OPRF antibody), unmodified STAT3-3G12, and ST3G12-PS antibody conjugate or 1 uM JAK inhibitor Tofacitinib. OPRF is a bacterial protein that is used as a control. The fold-change in gene expression level of IL-10, BCL2L1 (BCL-XL), and BIRC5 (Survivin) was determined.

FIG. 17B is a graph that shows the results of experiments that were carried out to determine the effect of anti-STAT3 antibody conjugate, "STAT3 iTAbs" (compound 901) on expression of STAT3 downstream genes in Colo205 cells. "Control iTAb" indicates the control antibody conjugate.

Figure 17C:
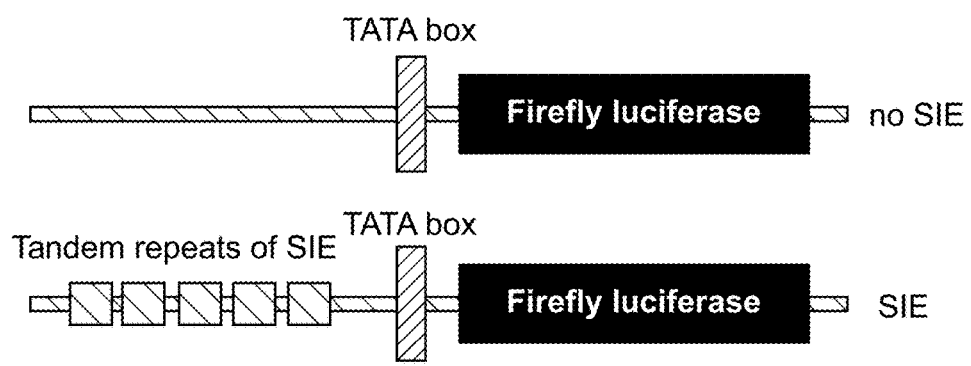

FIG. 17C is a schematic of two constructs that were used: one with tandem repeats of SIE upstream of the TATA box, and the other without the SIE tandem repeats to serve as a control.

Figure 17D:
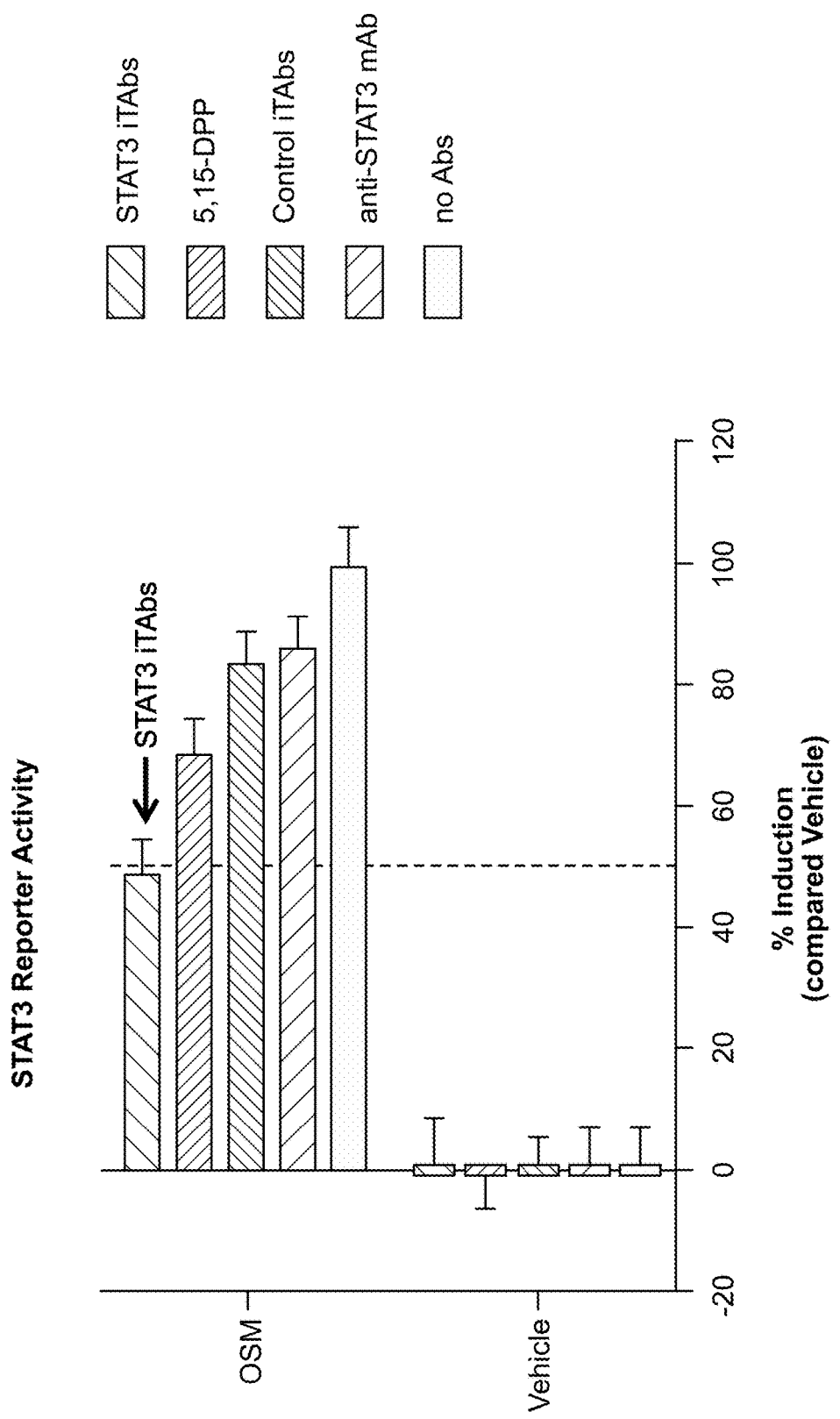

FIG. 17D is a graph that shows the results of a STAT3 reporter assay in HeLa cells. "STAT3 iTAbs" refers to the anti-STAT3 conjugate PS-ST3G12. "Control iTAb" indicates the control antibody conjugate.

Figure 17E:
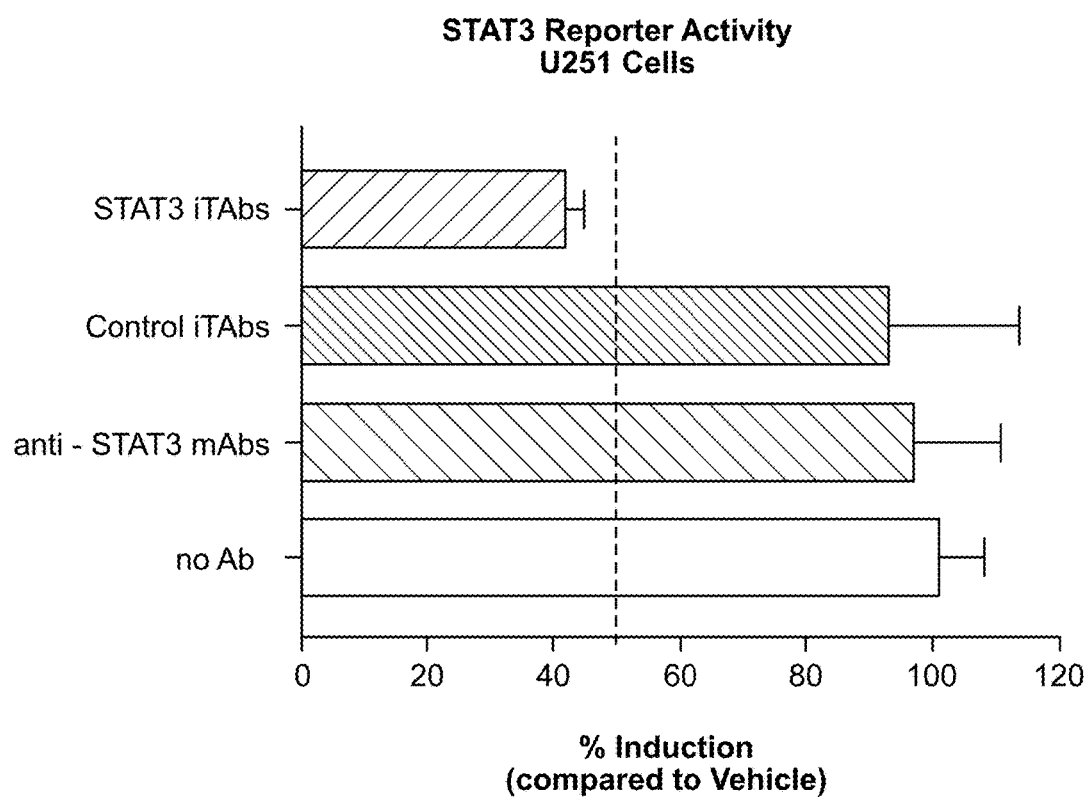

FIG. 17E is a graph that shows the results of a STAT3 reporter assay in U251 cells.

Figure 18A:
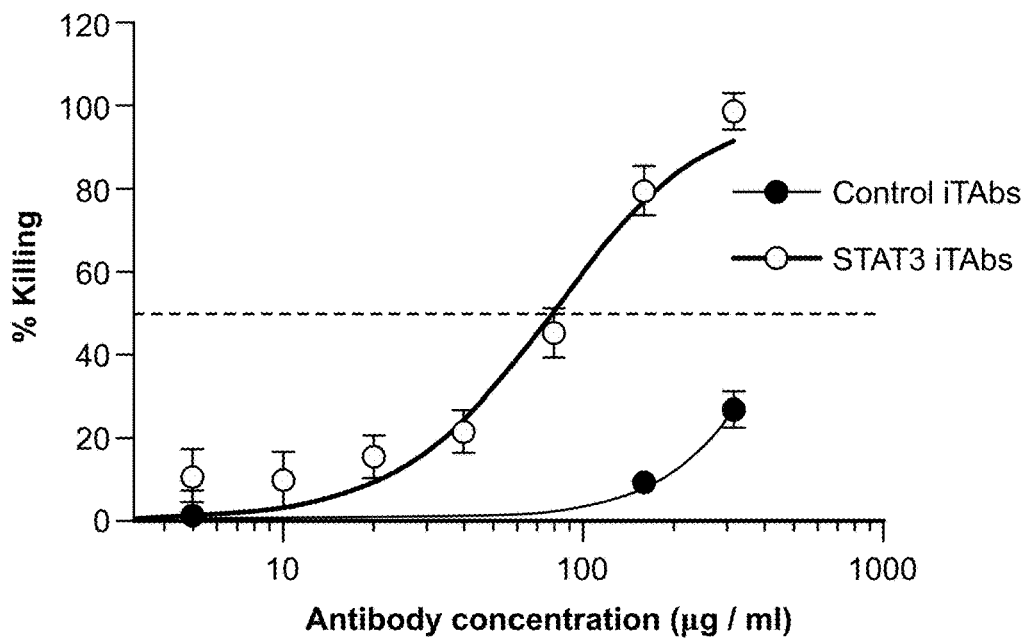

FIG. 18A is a graph that shows the percent killing of DU145 human prostate cancer cells with increasing antibody concentration (ug/ml) in a 2-dimensional (2D) tumor growth assay. Growth was monitored by MTS assay in triplicate wells. Error bars show one standard deviation. "STAT3 iTAbs" refers to the anti-STAT3 conjugate PS-ST3G12. "Control iTAb" indicates the control antibody conjugate.

Figure 18B:
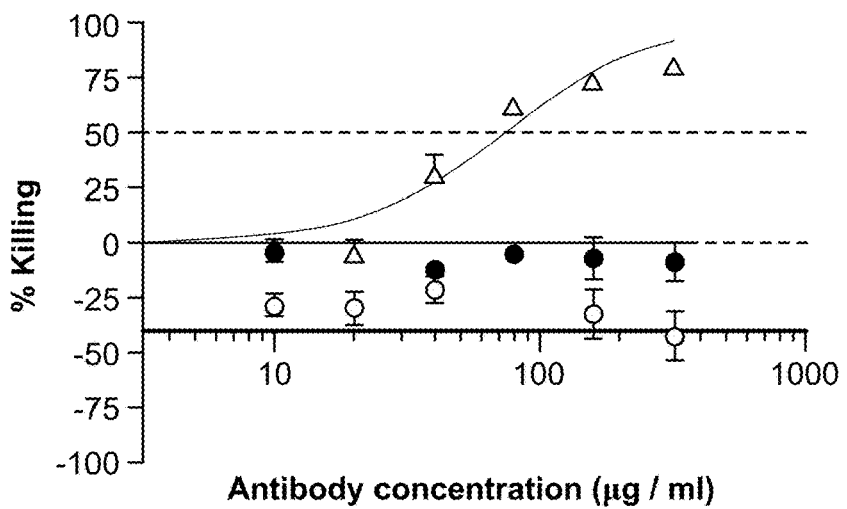

FIG. 18B is a graph that shows the percent killing of MDA-MB-231 human triple negative breast cancer (TNBC) cells with increasing antibody concentration (μg/ml) in the 2D assay. Growth was monitored by CTG assay in triplicate wells. Error bars show one standard deviation. "STAT3 iTAbs" refers to the anti-STAT3 conjugate PS-ST3G12. "Control iTAb" indicates the control antibody conjugate.

FIG. 18C shows detection of Alexa fluor by microscopy. As shown in FIG. 18C, the anti-STAT3 antibody conjugate (e.g. compound 901) was able to penetrate the tumor spheroids (ii) while the anti-STAT3 monoclonal antibodies did not (i). "STAT3 iTAbs" refers to the anti-STAT3 conjugate PS-ST3G12.

Figure 19A:
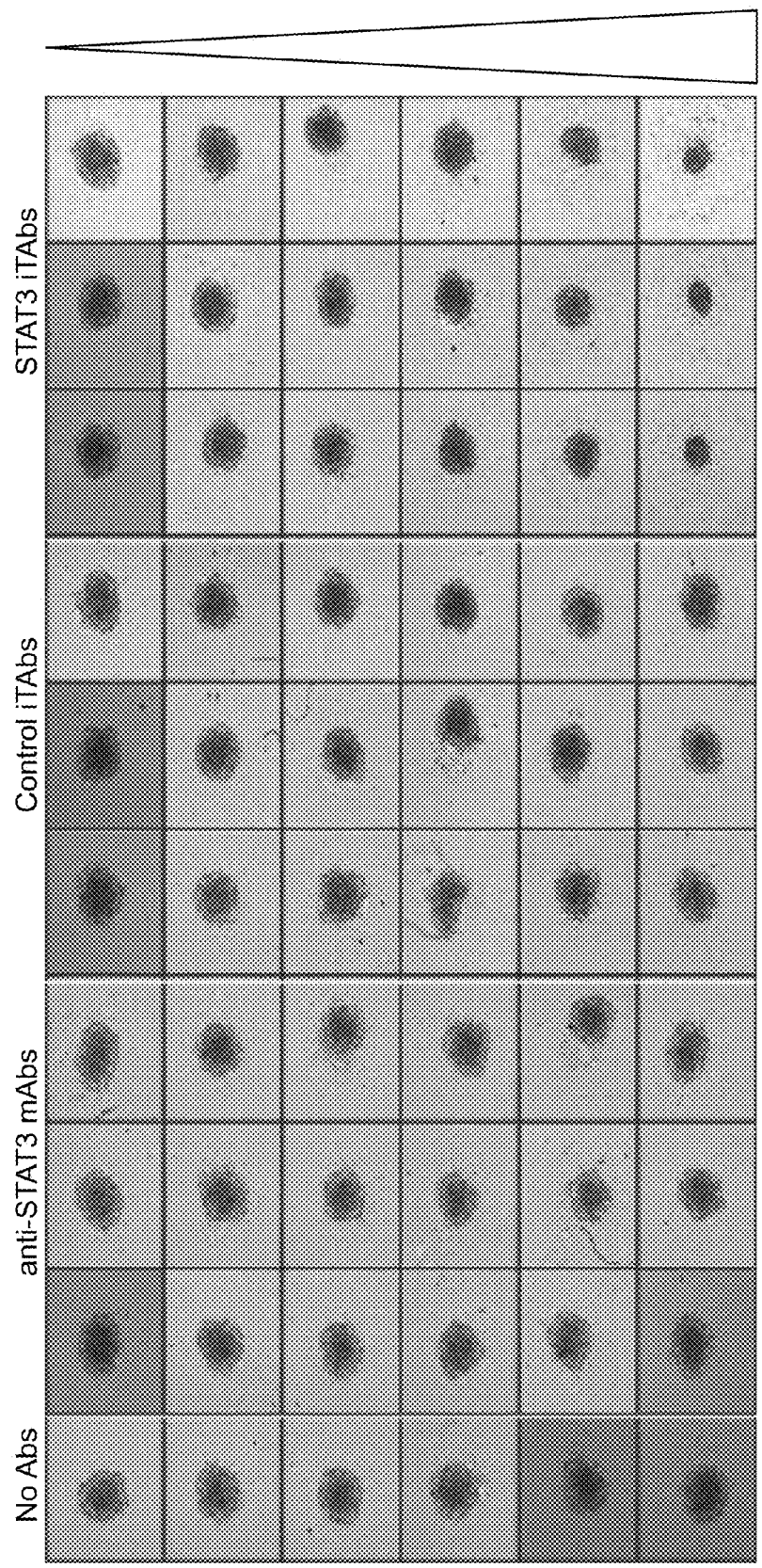

FIG. 19A shows the effect of the anti-STAT3 antibody conjugate (compound 901) on the growth of 3D tumor spheroids. DU145 human prostate cancer cell growth in a 3D tumor spheroid assay was monitored by ImageXpress HCS confocal microscopy in triplicate wells. Cells were treated with no antibodies, anti-STAT3 monoclonal antibodies, control conjugate ("Control iTAbs"), or anti-STAT3 antibody conjugate ST3G12 ("STAT3iTAbs").

Figure 19B:
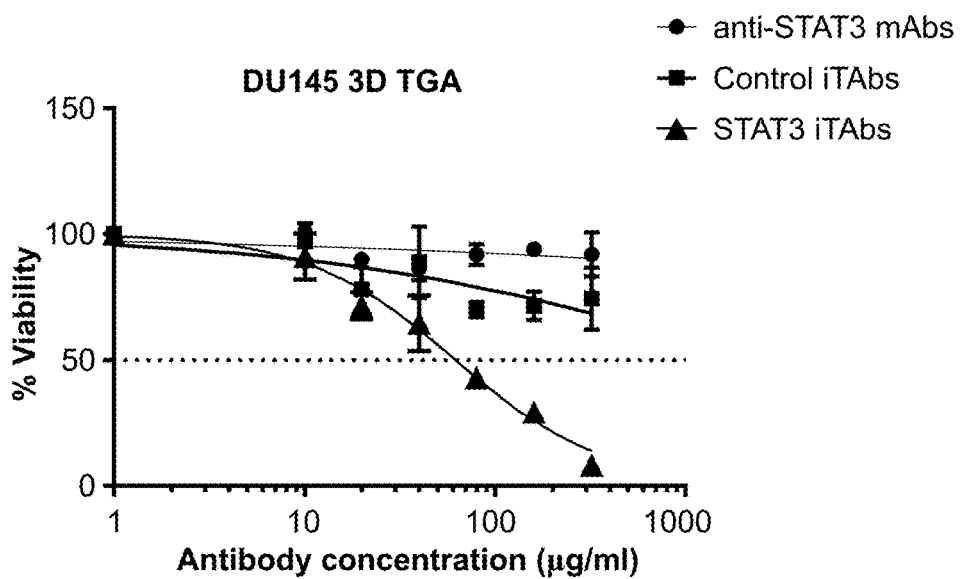

FIG. 19B is a graph that shows the effect of the anti-STAT3 antibody conjugate (compound 901) on the growth of 3D tumor spheroids. DU145 human prostate cancer cell growth in a 3D tumor spheroid assay was monitored by CTG assay in triplicate wells. "STAT3 iTAbs" refers to the anti-STAT3 conjugate PS-ST3G12.

Figure 19C:
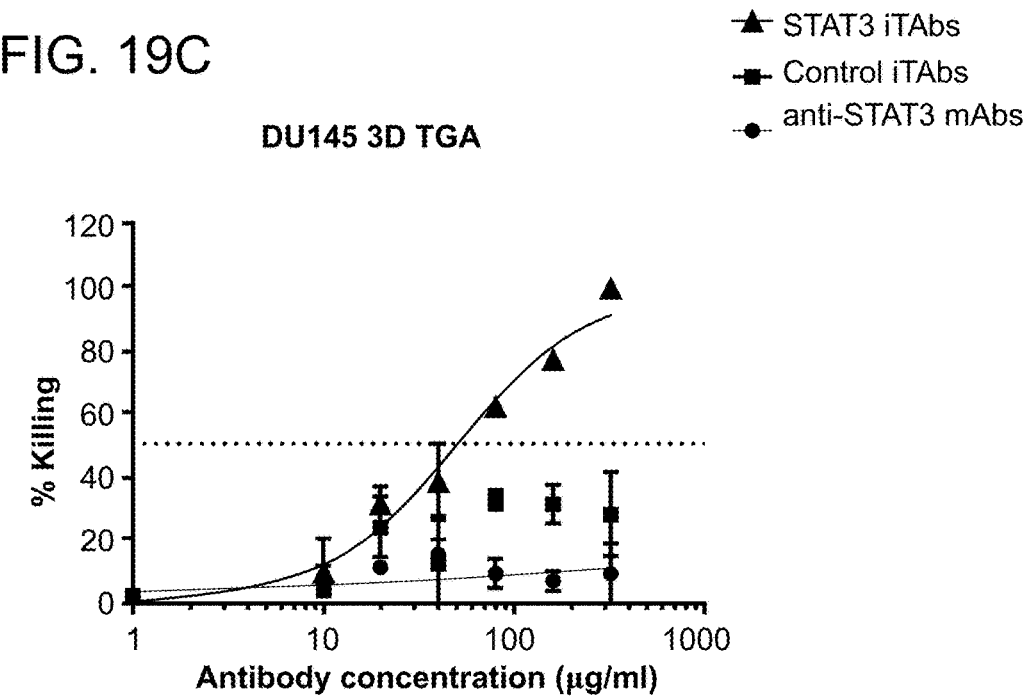

FIG. 19C is a graph that shows the effect of the anti-STAT3 antibody conjugate (compound 901) on the growth of 3D tumor spheroids. Percent killing of the cells is shown in FIG. 19C. "STAT3 iTAbs" refers to the anti-STAT3 conjugate PS-ST3G12.

FIG. 20A is an image that shows anti-STAT3 antibody conjugates can reduce the size of spheroids and may also induce a differentiated phenotype. Cells were treated with anti-STAT3 monoclonal antibodies, control antibody conjugate (PS conjugated anti-bacterial outer membrane protein I (OprI) antibody) or anti-STAT3 antibody conjugates. Live cells were stained with calcein AM live cell dye. In live cells the nonfluorescent calcein AM is converted to a green-fluorescent calcein. "STAT3 iTAbs" refers to the anti-STAT3 conjugate PS-ST3G12.

FIG. 20B is an image that shows the results of experiments to test the drug sensitivity to STAT3 antibody conjugate (compound 901) in a 3D-tumor growth assay in patient derived classic glioblastoma (GBM) mesenchymal cells.

The high content screening (HCS) confocal images in FIG. 20B show spheroids stained with fluorescent markers against Calcein AM for live cells (green), Ethidium homodimer-1 for dead cells (red) and Hoechst for nuclei (blue). "STAT3 iTAbs" refers to the anti-STAT3 conjugate PS-ST3G12.

Figure 20C:
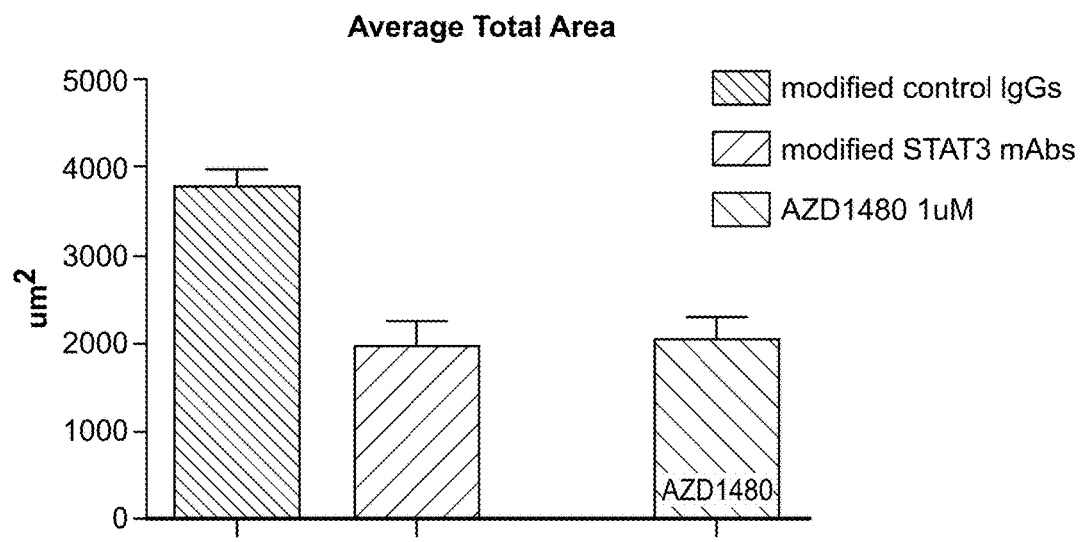

FIG. 20C is a graph that shows the average total area of the tumor spheroids after treatment with STAT3 antibody conjugate PS-ST3G12 ("modified STAT3 mAbs").

Figure 20D:
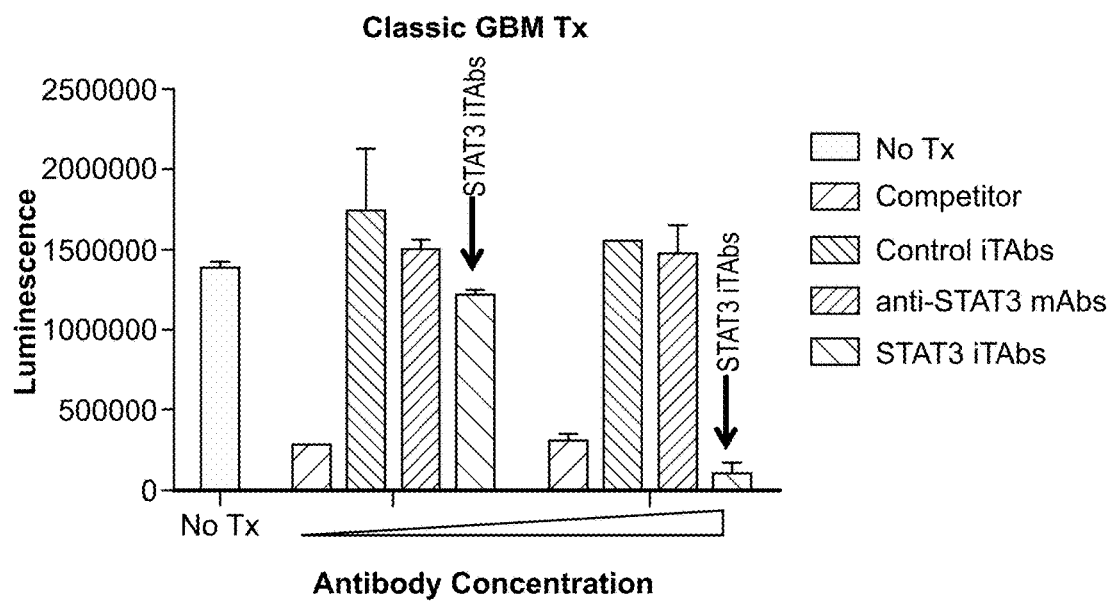

FIG. 20D is a graph that shows the results of experiments to test the drug sensitivity to STAT3 antibody conjugate (compound 901) in the 3D-tumor growth assay in patient derived classic glioblastoma (GBM). "STAT3 iTAbs" refers to the anti-STAT3 conjugate PS-ST3G12. "Control iTAb" indicates the control antibody conjugate.

Figure 20E:
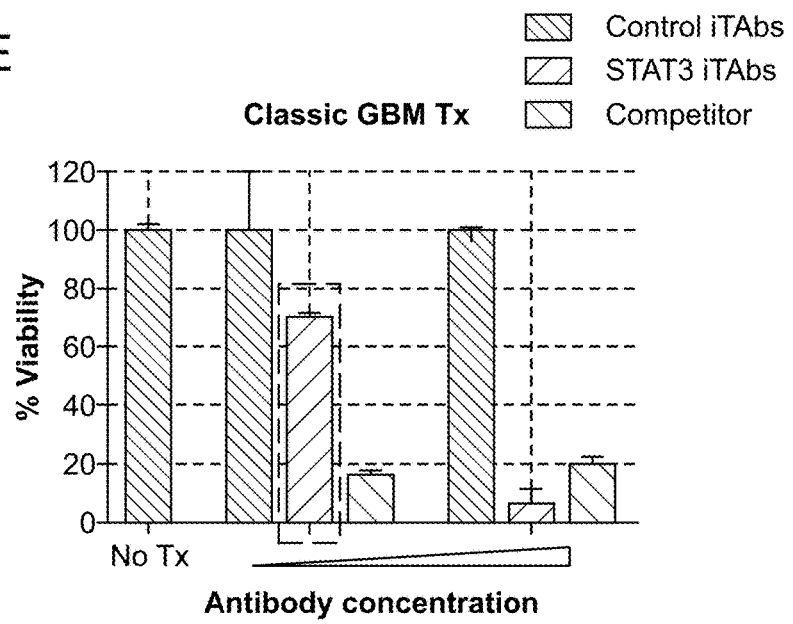

FIG. 20E is a graph that shows the results of experiments to test the drug sensitivity to STAT3 antibody conjugate (compound 901) in the 3D-tumor growth assay in patient derived classic glioblastoma (GBM). FIG. 20E shows percent viability of cells with increasing antibody concentration. "STAT3 iTAbs" refers to the anti-STAT3 conjugate PS-ST3G12. "Control iTAb" indicates the control antibody conjugate.

Figure 20F:
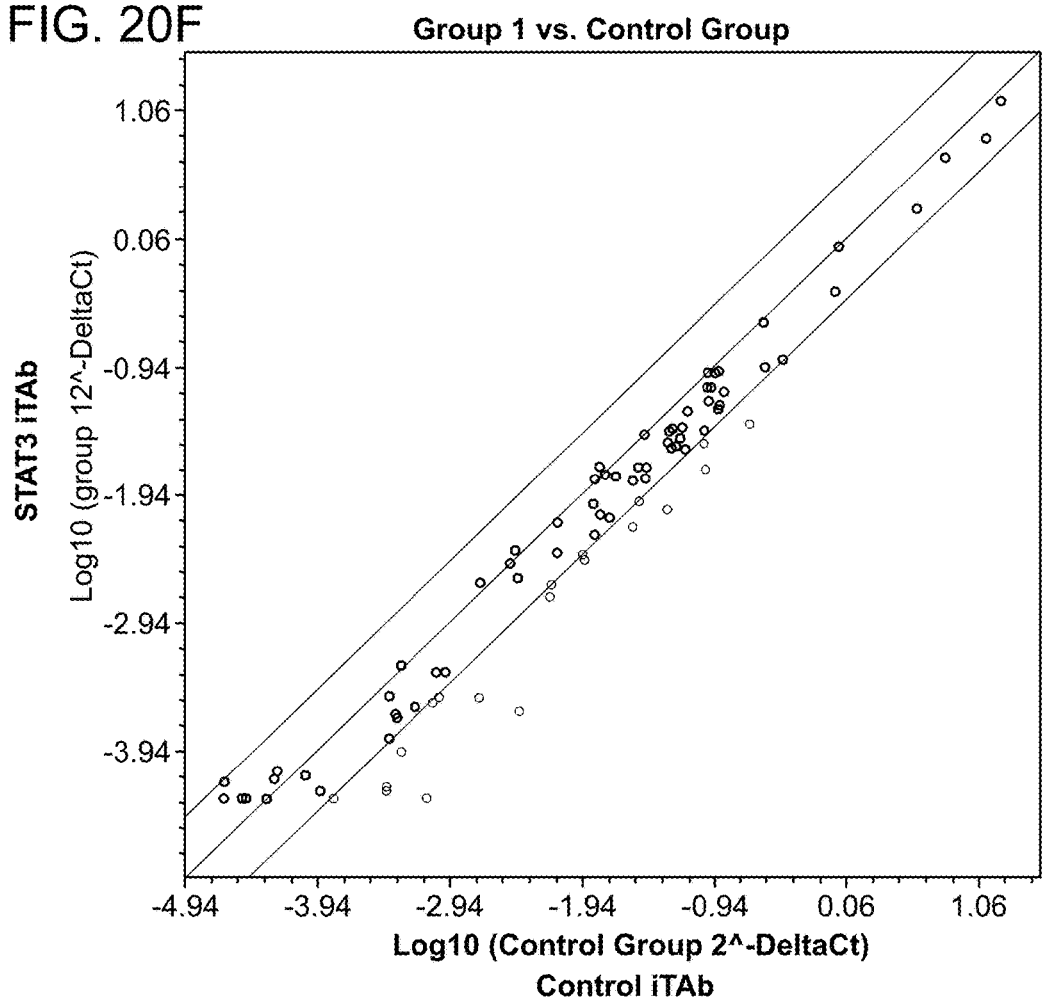

FIG. 20F is a graph that shows the scatter plots of signal intensity from each sample pair (STAT3 antibody conjugate (compound 901)-treated vs control antibody conjugate-treated) at the level of gene expression. "STAT3 iTAbs" refers to the anti-STAT3 conjugate PS-ST3G12. "Control iTAb" indicates the control antibody conjugate.

FIG. 20G is a graph that shows cancer stem cell genes that were downregulated by anti-STAT3 antibody conjugate (compound 901a) relative to control antibody conjugate (PS conjugated anti-bacterial outer membrane protein I (OprI) antibody). "STAT3 iTAbs" refers to the anti-STAT3 conjugate PS-ST3G12.

Figure 21A:
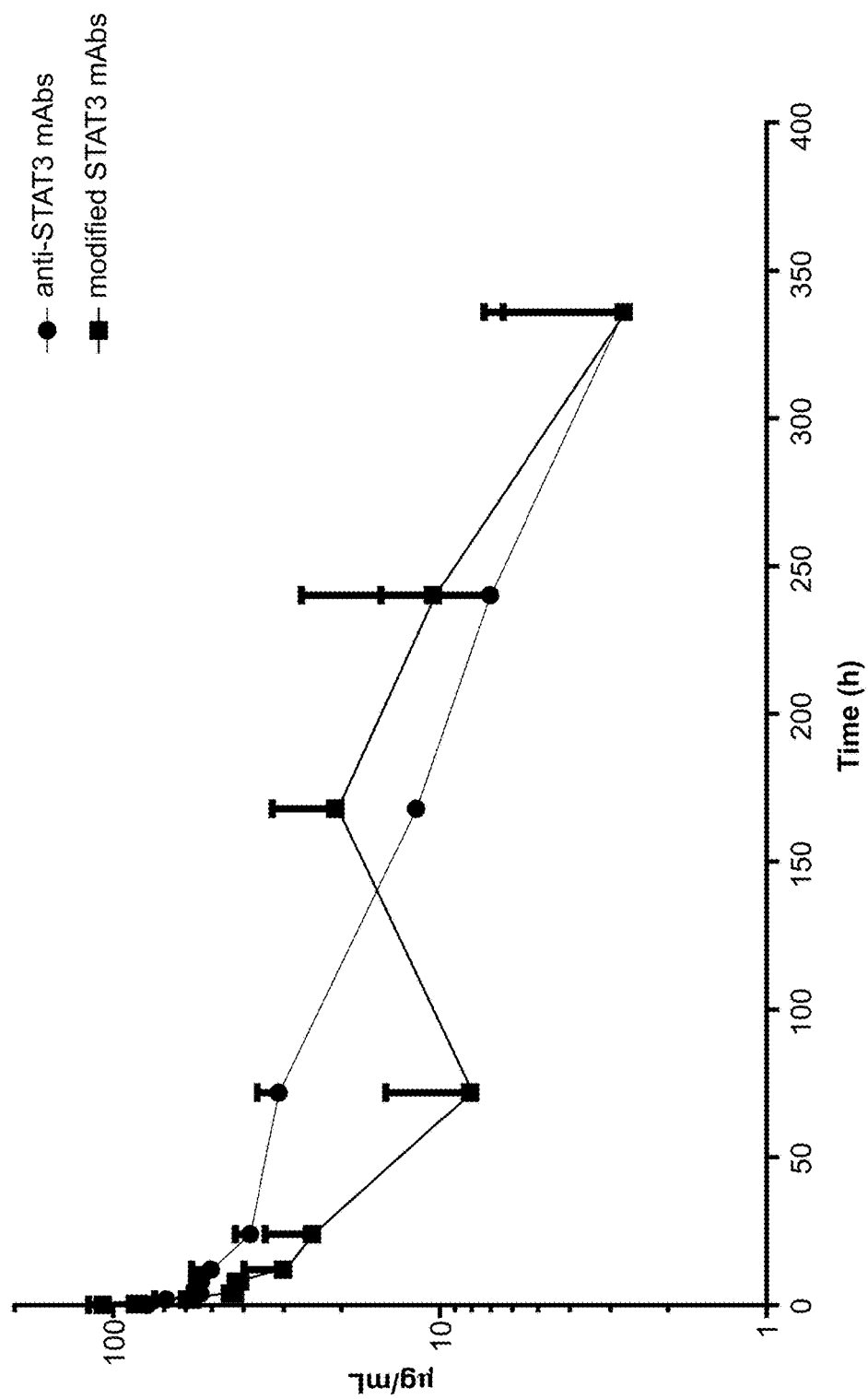

FIG. 21A is a graph that shows Pharmacokinetic profiling of STAT3 ST3G12 and STAT3 antibody conjugate PS-ST3G12 ("modified STAT3 mAbs") in athymic nude mice.

Figure 21B:
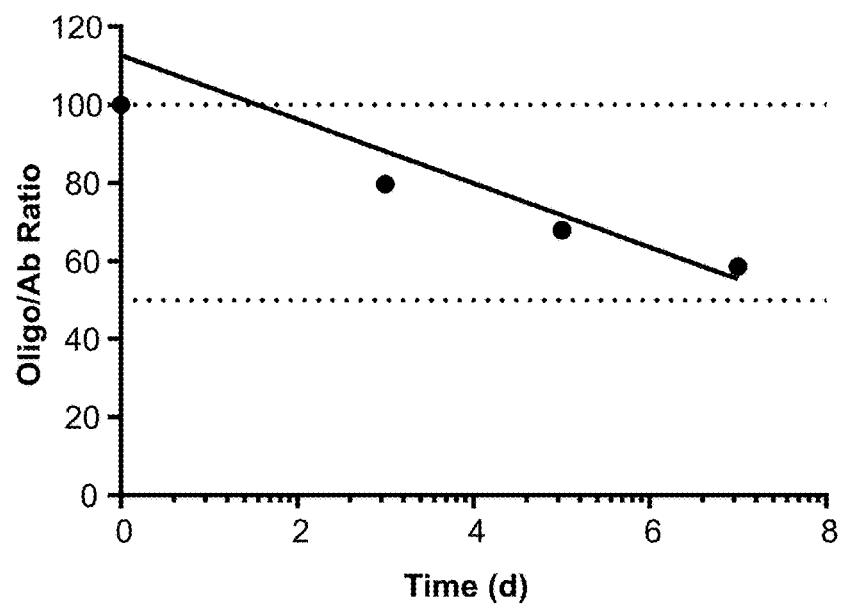

FIG. 21B is a graph that shows the results of experiments to assess anti-STAT3 antibody conjugate (compound 901) stability in human serum as determined by ELISA. Antibody amount spiked in the human sera was determined using anti-human IgG labeled with HRP. For the detection of PS oligos bound to STAT3 PS-ST3G12 (compound 901), Biotin-oligos complementary to PS oligos were first hybridized with serum spiked antibody conjugates and then the amount of antibody-bound oligos were assessed by ELISA as mentioned in the above, except that the anti-Streptavidin-HRP was used as detection antibody. Data were plotted as the ratio of signal from oligos to signal from antibody and shown as oligo/Ab ratio to indicate the change in antibody-bound oligo amount over time.

Figure 22A:
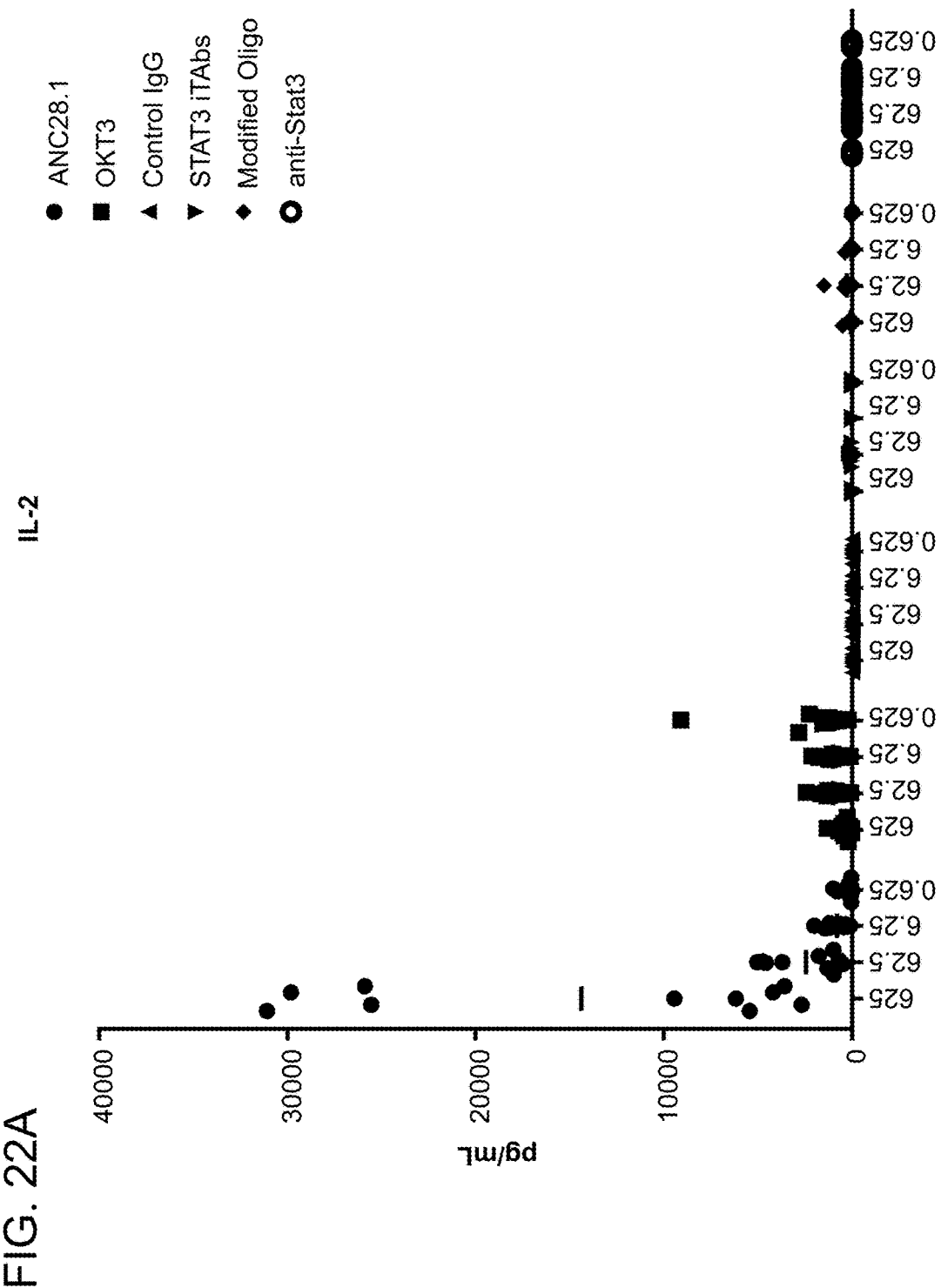

FIG. 22A is a graph that shows anti-STAT3 antibody conjugate (compound 901) did not stimulate the release of IL-2 from human PMBCs. Amount of IL-2 is shown in pg/mL. "STAT3 iTAbs" refers to the anti-STAT3 conjugate PS-ST3G12.

Figure 22B:
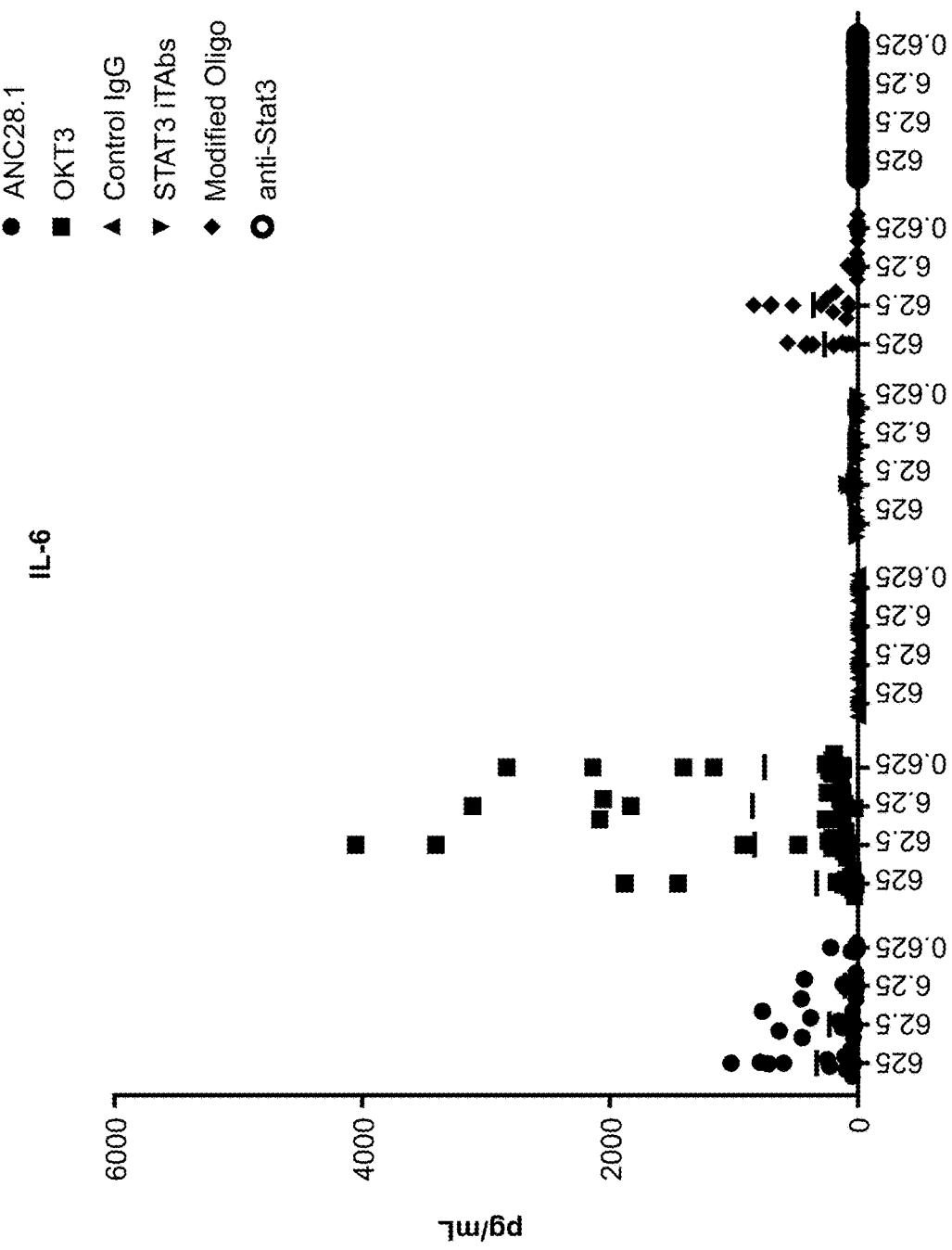

FIG. 22B is a graph that shows anti-STAT3 antibody conjugate (compound 901) did not stimulate the release of IL-6 from human PMBCs. Amount of IL-6 is shown in pg/mL. "STAT3 iTAbs" refers to the anti-STAT3 conjugate PS-ST3G12.

Figure 22C:
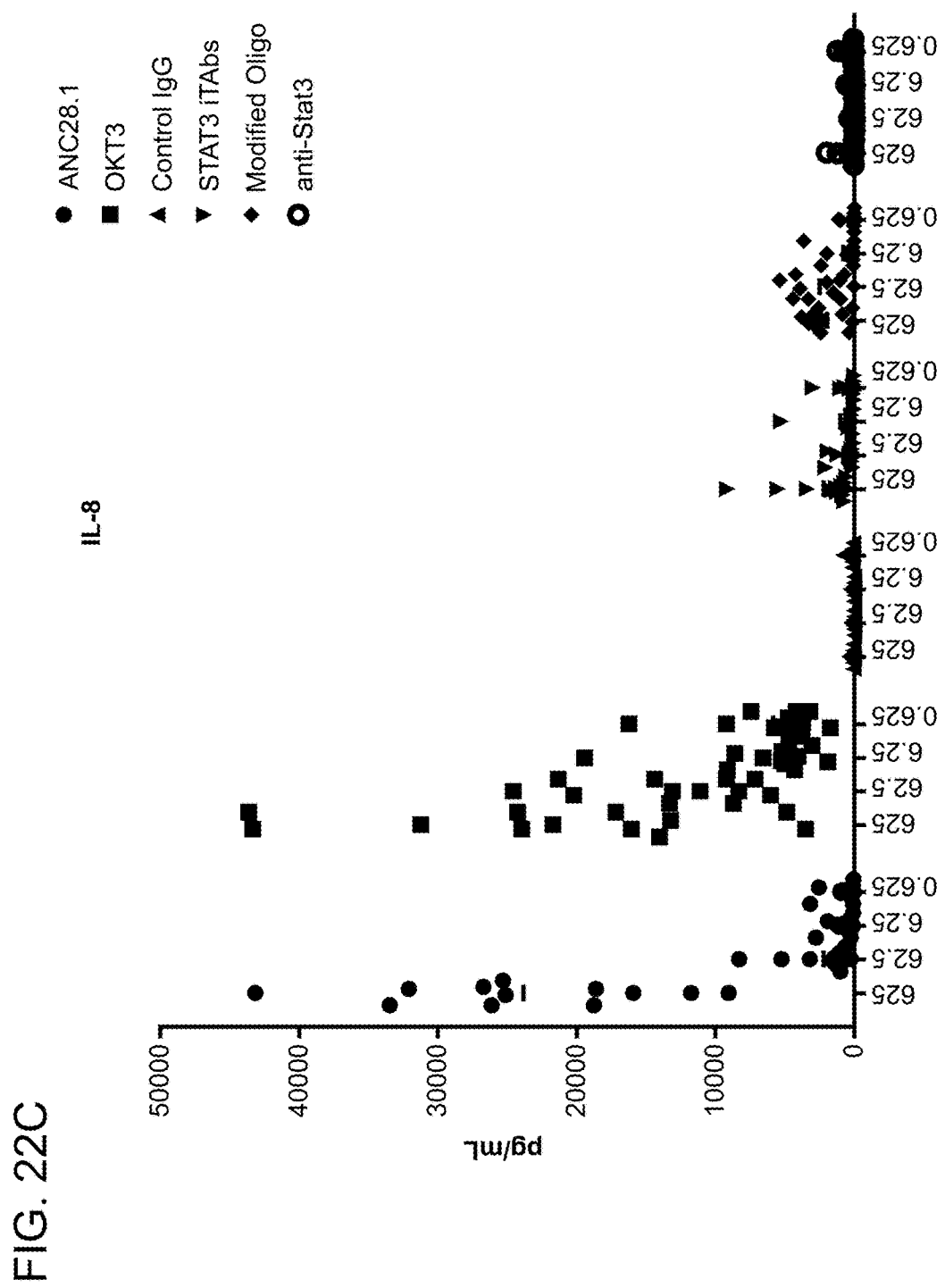

FIG. 22C is a graph that shows anti-STAT3 antibody conjugate (compound 901) did not stimulate the release of IL-8 from human PMBCs. Amount of IL-8 is shown in pg/mL. "STAT3 iTAbs" refers to the anti-STAT3 conjugate PS-ST3G12.

Figure 22D:
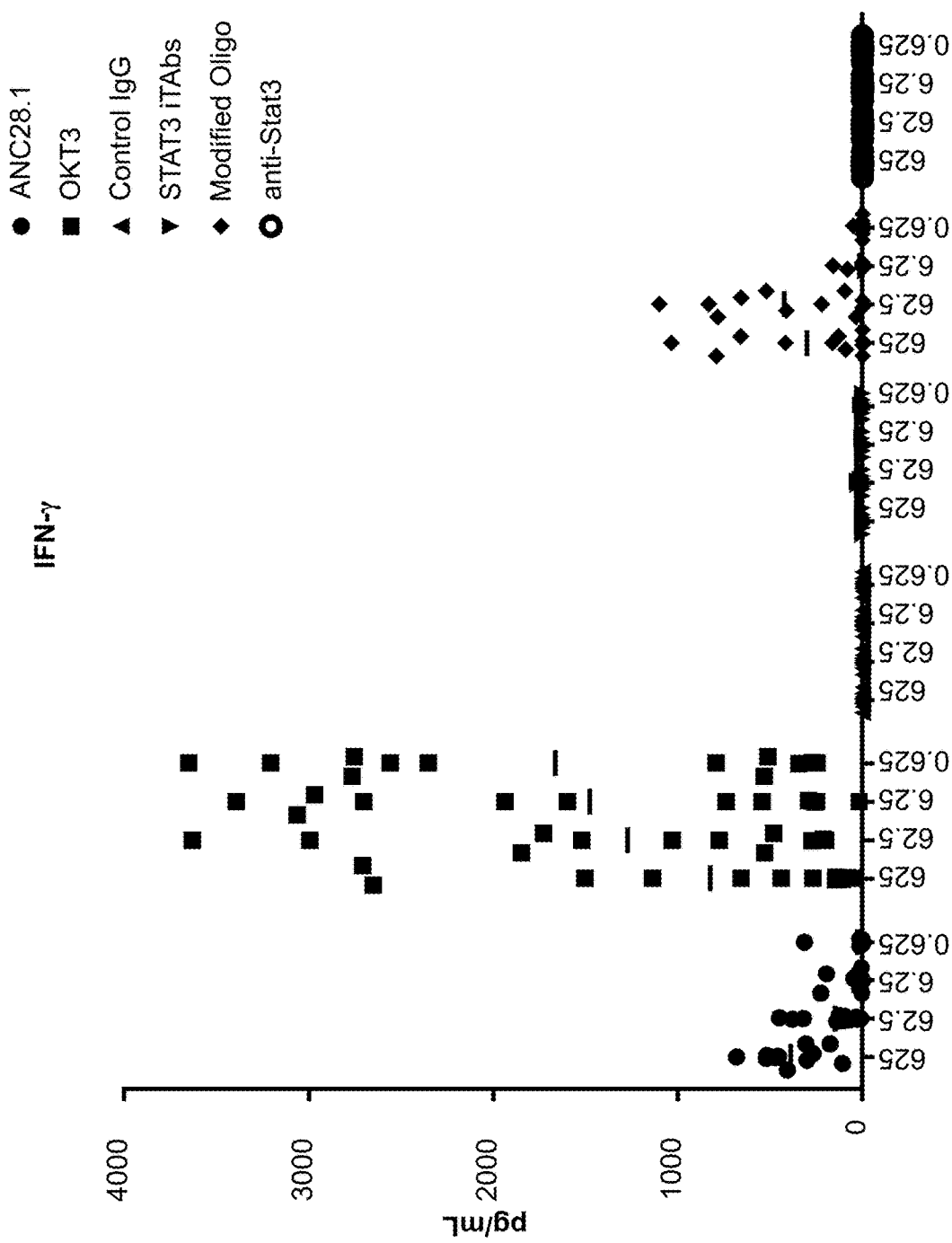

FIG. 22D is a graph that shows anti-STAT3 antibody conjugate (compound 901) did not stimulate the release of IFN-γ from human PMBCs. Amount of IFN-γ is shown in pg/mL. "STAT3 iTAbs" refers to the anti-STAT3 conjugate PS-ST3G12.

Figure 23:
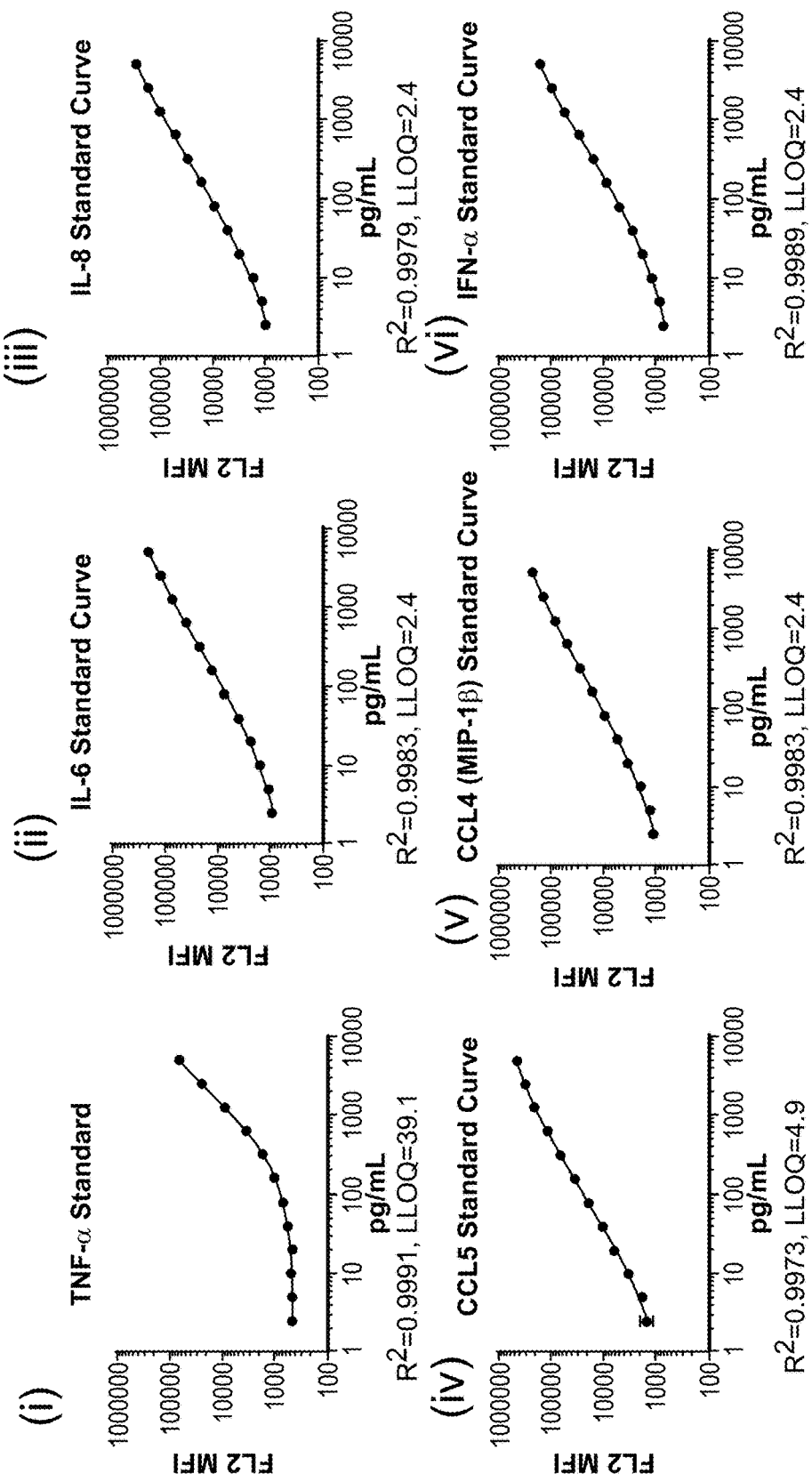

FIG. 23 is a panel of graphs ((i)-(vi)) reporting the standard curves showing the range of detection in the MultiCyt Qbeads plexscreen platform for (i) TNFα, (ii) IL-6, (iii) IL-8, (iv) CCL5, (v) CCL4 and (vi) IFNα.

Figure 24B:
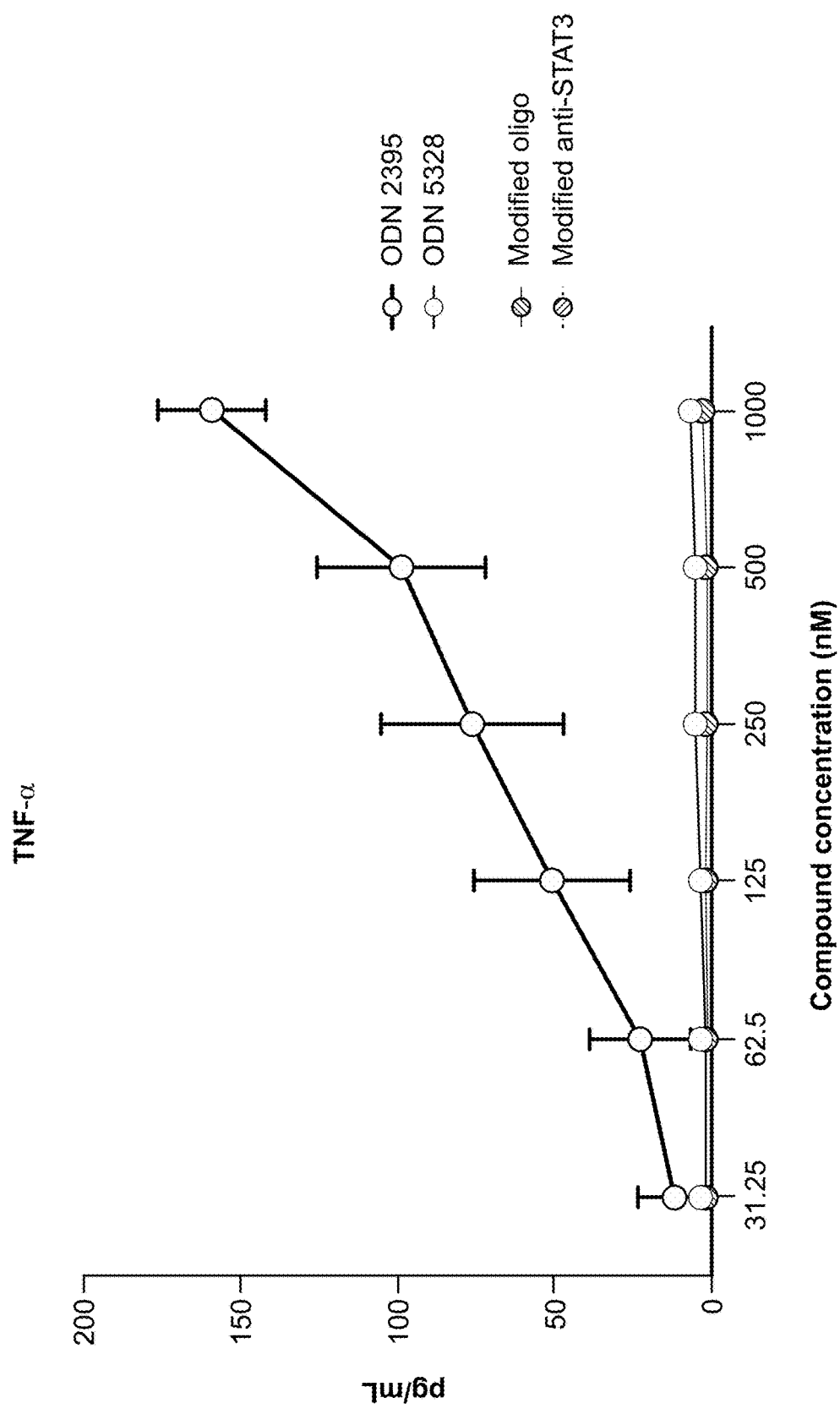

FIG. 24A and FIG. 24B are graphs that show the anti-STAT3 antibody conjugate, "modified STAT3 mAbs" (compound 901) did not stimulate the release of TNFα from human PMBCs. Compound concentration (nM) is shown on the x-axis, and TNFα detected in the conditioned media (pg/mL) is shown on the y-axis.

Figure 25A:
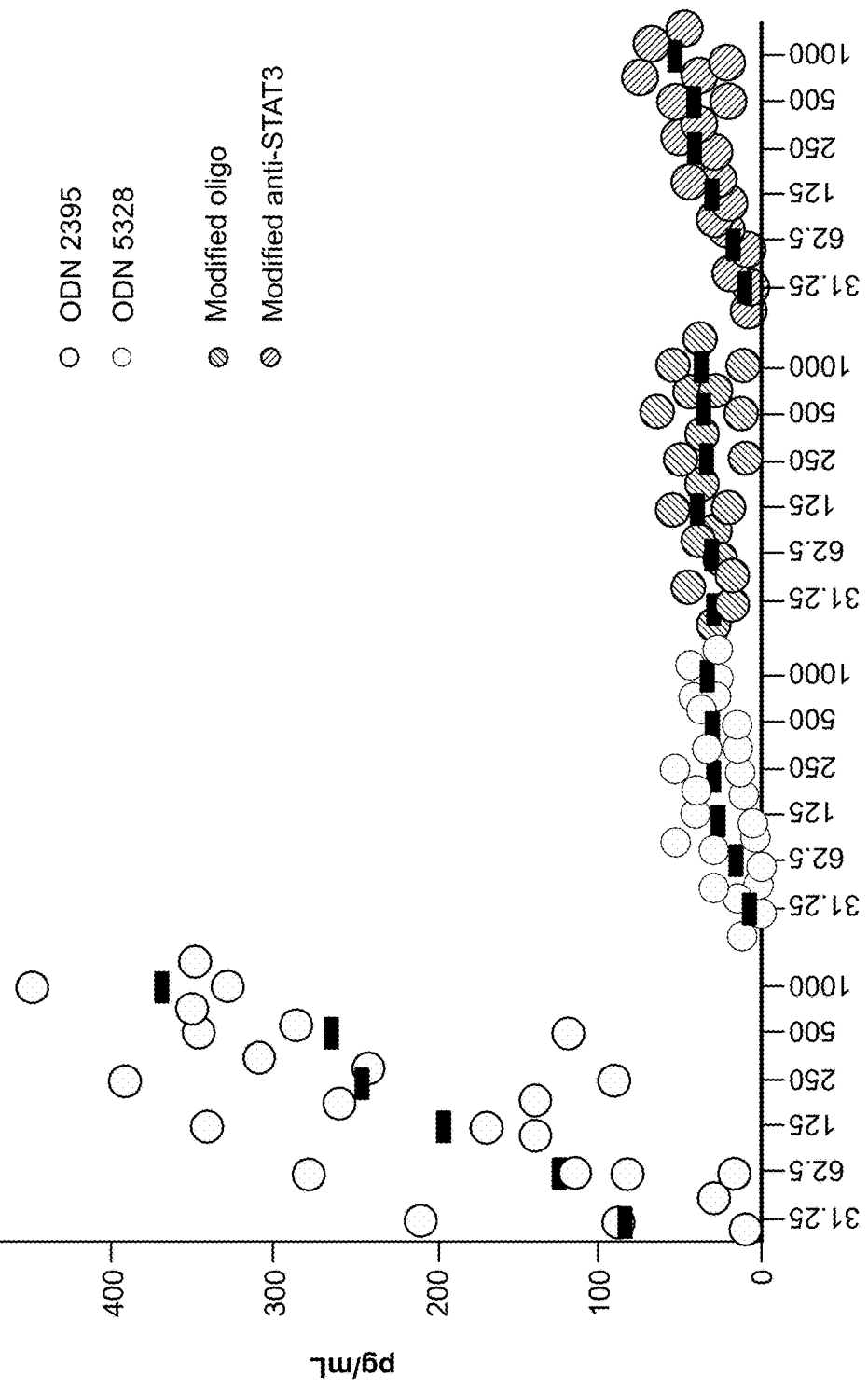
Figure 25B:
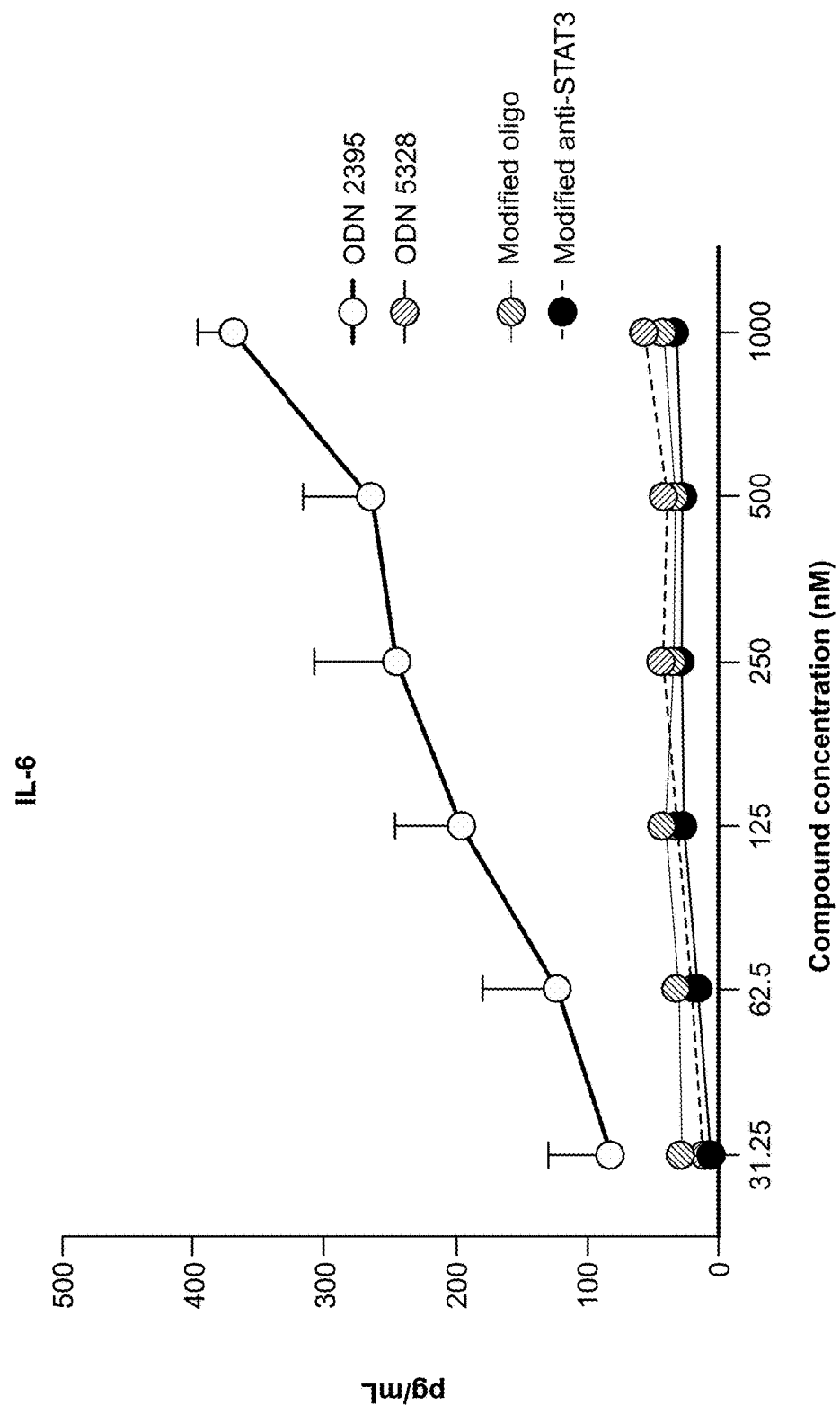

FIG. 25A and FIG. 25B are graphs that show the anti-STAT3 antibody conjugate, "modified STAT3 mAbs" (compound 901) did not stimulate the release of IL-6 from human PMBCs. Compound concentration (nM) is shown on the x-axis, and IL-6 detected in the conditioned media (pg/mL) is shown on the y-axis.

Figure 26B:
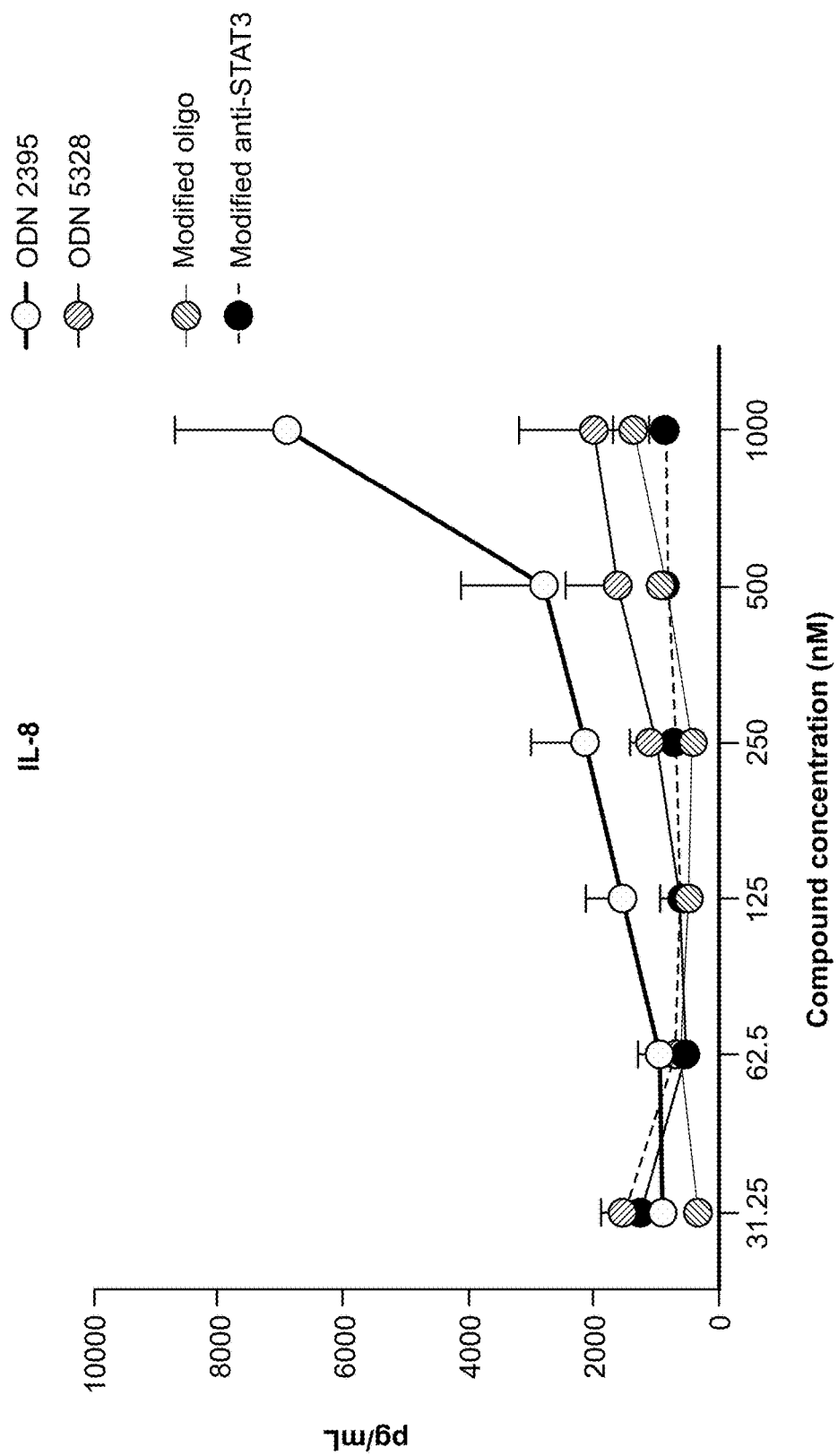

FIG. 26A and FIG. 26B are graphs that show the anti-STAT3 antibody conjugate, "modified STAT3 mAbs" (compound 901) did not stimulate the release of IL-8 from human PMBCs. Compound concentration (nM) is shown on the x-axis, and IL-8 detected in the conditioned media (pg/mL) is shown on the y-axis.

Figure 27A:
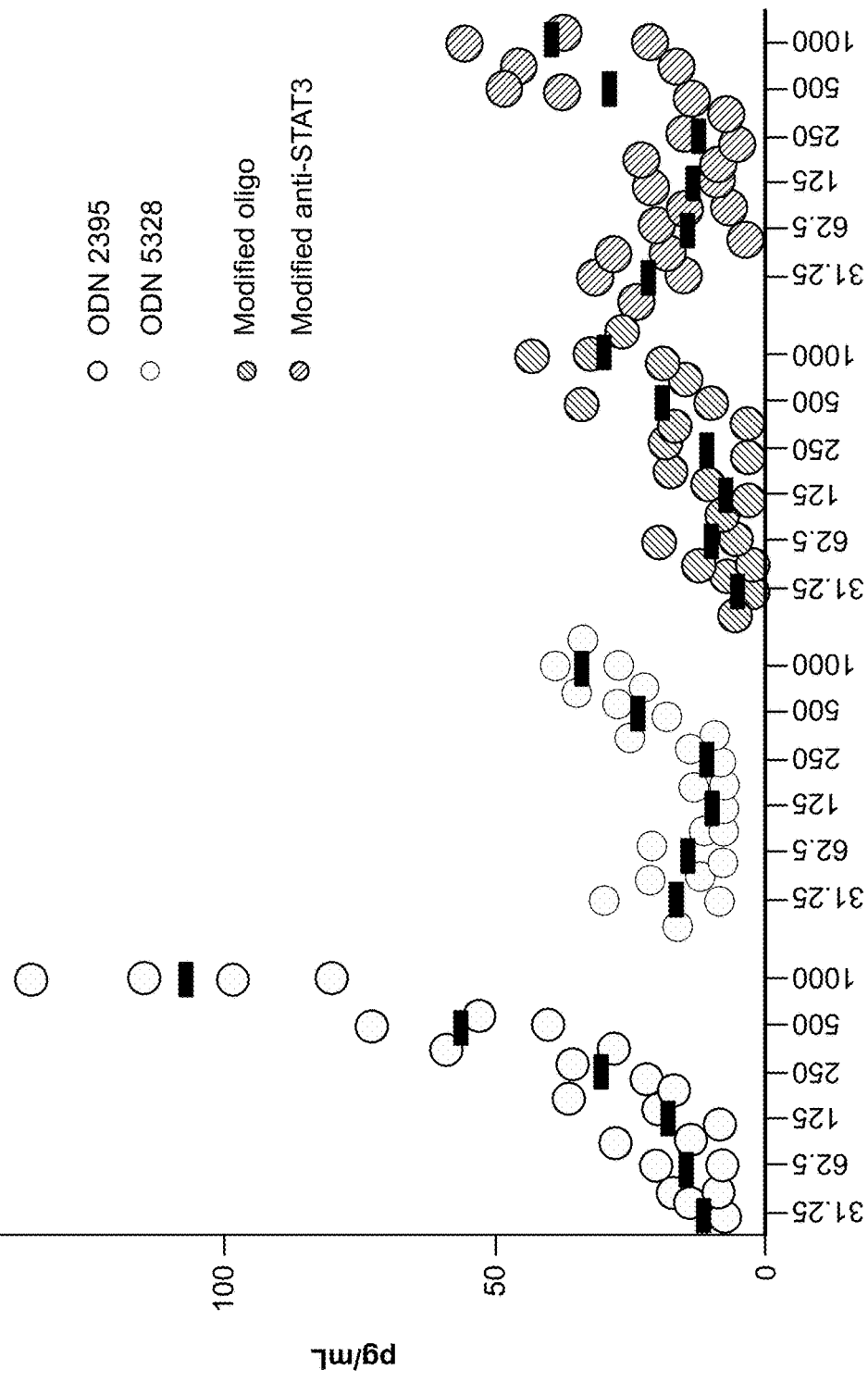
Figure 27B:
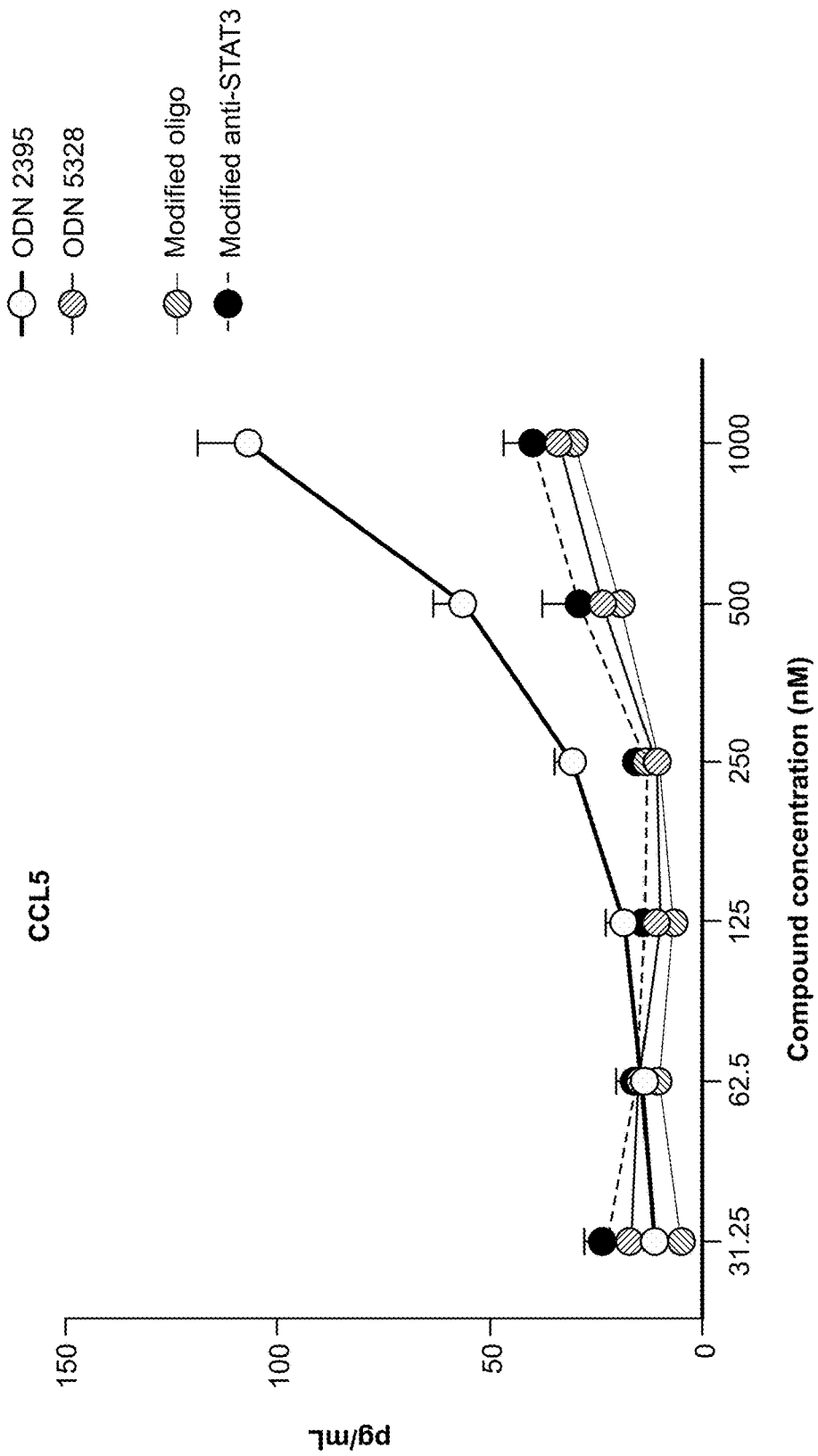

FIG. 27A and FIG. 27B are graphs that show the anti-STAT3 antibody conjugate, "modified STAT3 mAbs" (compound 901) did not stimulate the release of CCL5 from human PMBCs. Compound concentration (nM) is shown on the x-axis, and CCL5 detected in the conditioned media (pg/mL) is shown on the y-axis.

FIG. 28A and FIG. 28B are graphs that show the anti-STAT3 antibody conjugate, "modified STAT3 mAbs" (compound 901) did not stimulate the release of CCL7 from human PMBCs. Compound concentration (nM) is shown on the x-axis, and CCL7 detected in the conditioned media (pg/mL) is shown on the y-axis.

Figure 29B:
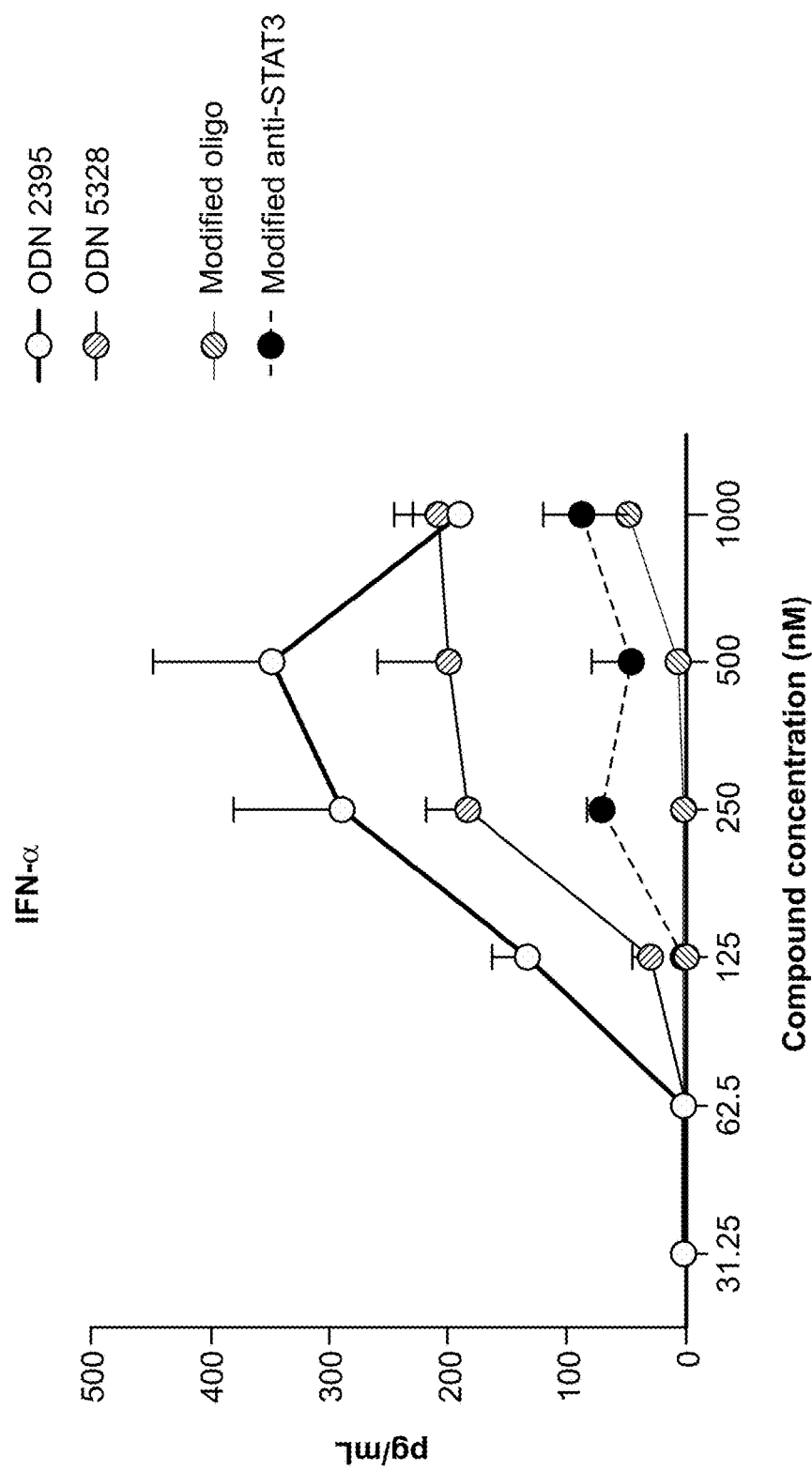

FIG. 29A and FIG. 29B are graphs that show the anti-STAT3 antibody conjugate, "modified STAT3 mAbs" (compound 901) did not stimulate the release of IFNα from human PMBCs. Compound concentration (nM) is shown on the x-axis, and IFNα detected in the conditioned media (pg/mL) is shown on the y-axis.

Figure 30:
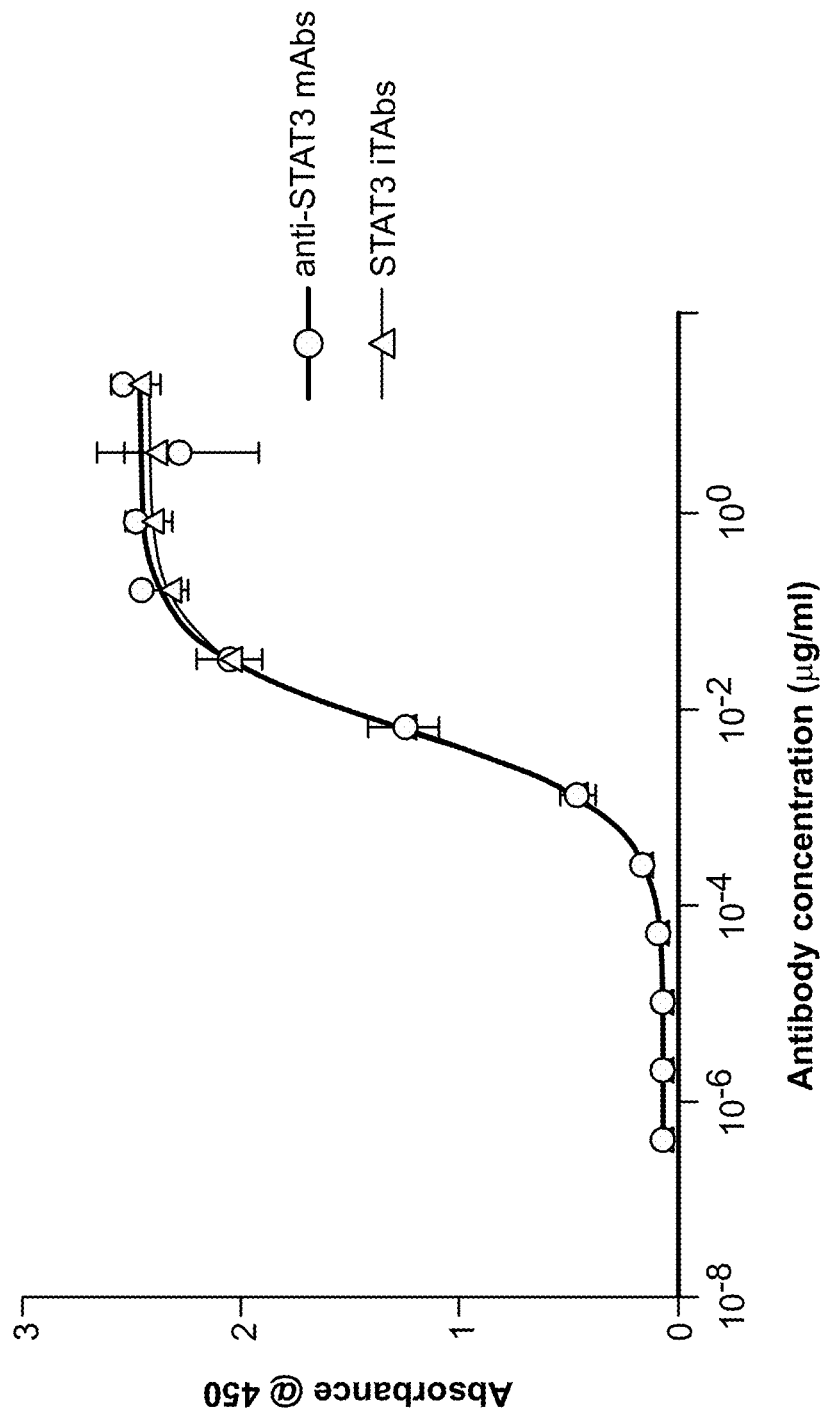

FIG. 30 is a graph that shows the results of an ELISA assay used to assess the binding of the PS modified ST3G12 antibody conjugate (compound 901)) and anti-STAT3 monoclonal antibodies to recombinant human STAT3 proteins. "STAT3 iTAbs" refers to the anti-STAT3 conjugate PS-ST3G12.

DETAILED DESCRIPTION

Definitions

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (i.e., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An "antigen binding domain," "antigen binding region," or "antigen binding site" is a portion of an antigen binding protein that contains amino acid residues (or other moieties) that interact with an antigen and contribute to the antigen binding proteins specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein). Generally the variable regions, particularly the CDRs, of an antibody interact with the epitope.

The term "antibody" refers to an immunoglobulin (Ig) molecule comprised of four polypeptide chains, two heavy (H) chains and two light (L) chains, or any functional fragment, mutant, variant, or derivation thereof, which retains the essential epitope binding features of an Ig molecule.

Generally, the amino-terminal portion of each antibody chain includes a variable region that is primarily responsible for antigen recognition. The carboxy-terminal portion of each chain defines a constant region, e.g., responsible for effector function. Human light chains are classified as kappa or lambda light chains Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites. A single VH or VL domain may be sufficient to confer antigen-binding specificity.

The variable regions of antibody heavy and light chains (VH and VL, respectively) exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is known in the art, including, for example, definitions as described in Kabat et al. in Sequences of Proteins of Immunological Interest, 5$^{th}$ Ed., US Dept. of Health and Human Services, PHS, NIH, NIH Publication no. 91-3242, 1991 (herein referred to as "Kabat numbering"). For example, the CDR regions of an antibody can be determined according to Kabat numbering.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

The terms "anti-STAT3 antibody" and "an antibody that binds to STAT3" refer to an antibody that is capable of binding STAT3 with sufficient affinity such that the antibody is useful as a diagnostic and/or therapeutic agent in targeting STAT3, including human STAT3.

The terms "intact antibody" or "full length antibody" refer to an antibody composed of two antibody light chains and two antibody heavy chains that each contain an Fc region.

The term "monospecific", as used herein, refers to an antibody, or antigen binding fragment thereof, that displays an affinity for one particular epitope. In contrast, a bispecific antibody, or antigen-binding fragment thereof, displays affinity for two different epitopes. In one embodiment, the methods and compositions described herein are useful for intracellular delivery of a monospecific antibody, or antigen-binding fragment thereof.

A "multi-specific antibody" is an antibody that recognizes more than one epitope on one or more antigens. A subclass of this type of antibody is a "bispecific antibody" which recognizes two distinct epitopes on the same or different antigens.

The terms "specific binding", "specifically binds" or "specifically binding", as used herein in the context of an antibody, refer to non-covalent or covalent preferential binding of an antibody to an antigen relative to other molecules or moieties (e.g., an antibody specifically binds to a particular antigen relative to other available antigens). In one embodiment, an antibody specifically binds to an antigen (e.g., STAT3) if it binds to the antigen with a dissociation constant $K_D$ of $10^{-5}$ M or less (e.g., $10^{-6}$ M or less, $10^{-7}$ M or less, $10^{-8}$ M or less, $10^{-9}$ M or less, or $10^{-10}$ M or less).

The term "human antibody", as used herein, refers to an antibody, or an antigen binding fragment of an antibody, comprising heavy and lights chains derived from human immunoglobulin sequences. Human antibodies may be identified in a variety of ways, examples of which are described below, including through the immunization with an antigen of interest of a mouse that is genetically modified to express antibodies derived from human heavy and/or light chain-encoding genes. In one embodiment, a human antibody is made using recombinant methods such that the glycosylation pattern of the antibody is different than an antibody having the same sequence if it were to exist in nature.

The term "chimeric antibody" refers to an antibody that contains one or more regions derived from a particular source or species, and one or more regions derived from a different source or species.

The term "humanized antibody" refers to antibodies which comprise heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. A humanized antibody has a sequence that differs from the sequence of an antibody derived from a non-human species by one or more amino acid substitutions, deletions, and/or additions. Generally, a humanized antibody is less likely to induce an immune response, and/or induces a less severe immune response, as compared to the non-human species antibody, e.g., a murine or chimeric antibody, when it is administered to a human subject. In one embodiment, certain amino acids in the framework and constant domains of the heavy and/or light chains of the non-human species antibody are mutated to produce the humanized antibody. Examples of how to make humanized antibodies may be found in U.S. Pat. Nos. 6,054,297, 5,886,152 and 5,877,293.

An "antibody fragment", "antibody portion", "antigen-binding fragment of an antibody", or "antigen-binding portion of an antibody" refers to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, and tetrabodies.

In one embodiment, the antibody fragment is an scFv. A single-chain antibody (scFv) is an antibody in which a $V_L$ and a $V_H$ region are joined via a linker (e.g., a synthetic sequence of amino acid residues) to form a continuous protein chain (see e.g., Bird et al. (1988) Science 242:423-426; and Huston et al. (1988) Proc. Natl. Acad. Sci. USA 85:5879-5883)).

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App Pub 20/0202512; 2004/0202995; 2004/0038291; 2004/0009507; 2003/0039958, and Ward et al., Nature 341:544-546, 1989).

Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or possibly more than one expression vector) comprising the coding sequence of the antibody, or a portion thereof (e.g., a DNA sequence encoding a heavy chain or a light chain). In one embodiment, said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds STAT3, which is sufficient to effect treatment of a disease associated with STAT3 signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

A "neutralizing antibody" or an "inhibitory antibody" is an antibody that inhibits the proteolytic activation of STAT3 when an excess of the anti-STAT3 antibody reduces the amount of activation by at least about 20% using an assay such as those described herein in the Examples. In various embodiments, the antigen binding protein reduces the amount of amount of proteolytic activation of STAT3 by at least 30%, 40%, 50%, 60%, 70%, 75%, 80%, 85%, 90%, 95%, 97%, 99%, and 99.9%.

An "intracellular delivery compound", as used herein, refers to a compound which is conjugated (covalently or non-covalently) to an antigen binding protein (e.g., an antibody or antibody fragment) which is capable of internalizing the antigen binding protein into a cell. Examples of intracellular delivery compounds (conjugated to an antibody) are provided in FIGS. 1A, 1B, and 1C.

STAT3 Antigen Binding Proteins

The invention provides anti-STAT3 antigen binding proteins, e.g., antibodies and fragments thereof, as well as methods of using and making the same. Signal transducer and activator of transcription 3 (STAT3) is a member of the STAT family of cytoplasmic transcription factors. STAT3 is a transcription factor encoded by a STAT3 gene, which has a human gene map locus of 17q21. Human STAT3 is a 770 amino acid protein and has a molecular weight of about 88 kDa.

The present invention pertains to STAT3 binding proteins, particularly anti-STAT3 antibodies, or antigen-binding portions thereof, that bind STAT3 (e.g., human STAT3), and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human STAT3, to inhibit STAT3 activity, either in vitro or in vivo, and to prevent or treat disorders such as cancer are also encompassed by the invention.

As described in Table 4 below, included in the invention are novel antibody heavy and light chain variable regions that are specific to STAT3. In one embodiment, the invention provides an anti-STAT3 antibody, or an antigen-binding fragment thereof, that comprises a heavy chain having a variable domain comprising an amino acid sequence as set forth in any one of SEQ ID NOs. 1 and 3. In one embodiment, the invention provides an anti-STAT3 antibody, or an antigen-binding fragment thereof, that comprises a light chain having a variable domain comprising an amino acid sequence as set forth in any one of SEQ ID NOs. 2 and 4. In one embodiment, the invention provides an anti-STAT3 antibody, or an antigen-binding fragment thereof, that comprises a light chain having a variable domain comprising an amino acid sequence as set forth in any one of SEQ ID NOs. 2 and 4; and a heavy chain having a variable domain comprising an amino acid sequence as set forth in any one of SEQ ID NOs. 1 and 3.

In one embodiment, the invention includes an anti-STAT3 antibody which is an IgG and comprises four polypeptide chains including two heavy chains each comprising a heavy chain variable domain and heavy chain constant regions $C_{H1}$, $C_{H2}$ and $C_{H3}$, and two light chains each comprising a light chain variable domain and a light chain constant region ($C_L$). In certain embodiments, the antibody is an IgG1, IgG2, IgG3 or an IgG4. The heavy and light chain variable domain sequences may be selected from those described herein in SEQ ID Nos: 1, 2, 3, and/or 4.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences, including the identification of CDRs, that is applicable to any antibody.

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In certain embodiments, the present invention provides an anti-STAT3 antibody comprising the CDRs of a heavy and a light chain variable domain as described in Table 4 (SEQ ID Nos: 1 to 4). For example, the invention provides an anti-STAT3 antibody, or antigen-binding fragment thereof, comprising a heavy chain variable region having CDRs described in an amino acid sequence as set forth in any one of SEQ ID NO. 1 and SEQ ID NO. 3. In one embodiment, the invention provides an anti-STAT3 antibody, or antigen-binding fragment thereof, comprising a light chain variable region having CDRs described in an amino acid sequence as set forth in any one of SEQ ID NO. 2 and SEQ ID NO. 4. In one embodiment, the invention provides an anti-STAT3 antibody, or antigen-binding fragment thereof, comprising a light chain variable region having CDRs described in an amino acid sequence as set forth in any one of SEQ ID NO. 2 and SEQ ID NO. 4; and a heavy chain variable region having CDRs described in an amino acid sequence as set forth in any one of SEQ ID NO. 1 and SEQ ID NO. 3.

In one embodiment, the present disclosure provides a fully human antibody of an IgG class that binds to a STAT3 epitope with a binding affinity of $10^{-6}$M or less, that has a heavy chain variable domain sequence that is at least 95% identical, at least 96% identical, at least 97% identical, at least 98% identical, at least 99% identical, or 100% identical to an amino acid sequence selected from SEQ ID NO: 1 or SEQ ID NO: 3; and that has a light chain variable domain sequence that is at least 95% identical, at least 96% identical, at least 97% identical, at least 98% identical, at least 99% identical, or 100% identical to an amino acid sequence selected from SEQ ID NO: 2 or SEQ ID NO: 4.

In one embodiment, the invention provides an anti-STAT3 antibody, or an antigen-binding fragment thereof, comprising a heavy chain comprising a CDR3 domain as set forth in any one of SEQ ID NOs. 1 or 3, and comprising a variable domain comprising an amino acid sequence that has at least 95%, at least 96%, at least 97%, at least 98%, or at least 99% identical to a sequence as set forth in any one of SEQ ID NOs. 1 or 3. In one embodiment, the invention provides an anti-STAT3 antibody, or an antigen-binding fragment thereof, comprising a light chain comprising a CDR3 domain as set forth in any one of SEQ ID NOs. 2 or 4, and having a light chain variable domain comprising an amino acid sequence that has at least 95%, at least 96%, at least 97%, at least 98%, or at least 99% identical to a sequence as set forth in any one of SEQ ID NOs. 2 or 4. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to STAT3 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 4. The antibodies of the invention, including those described in Table 4, bind to human STAT3. In one embodiment, the fully human antibody has both a heavy chain and a light chain wherein the antibody has a heavy chain/light chain variable domain sequence selected from SEQ ID NO. 1/SEQ ID NO. 2 (called ST1A5 herein) or SEQ ID NO. 3/SEQ ID NO. 4 (called ST3G12 herein).

In one embodiment, the present invention is directed to an antibody, or an antigen binding fragment thereof, having antigen binding regions of antibody ST1A5. In one embodiment, the invention provides an antibody, or antigen-binding fragment thereof, comprising a heavy chain variable domain sequence as set forth in SEQ ID NO: 1, and a light chain variable domain sequence as set forth in SEQ ID NO: 2. In one embodiment, the invention is directed to an antibody having a heavy chain variable domain comprising the CDRs of SEQ ID NO: 1, and a light chain variable domain comprising the CDRs of SEQ ID NO: 2. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 1, and comprises a light chain variable region having an amino acid sequence that is at least 95% identical, at least 96% identical, at least 97% identical, at least 98% identical, or at least 99% identical to the sequence set forth in SEQ ID NO: 2. In one embodiment, the invention features an anti-STAT3 antibody, or an antigen-binding portion thereof, comprising a heavy chain variable region comprising a CDR3 domain comprising the amino acid as set forth in SEQ ID NO: 9, a CDR2 domain comprising the amino acid sequence as set forth in SEQ ID NO: 8, and a CDR1 domain comprising the amino acid sequence as set forth in SEQ ID NO: 7; and comprising a light chain variable region comprising a CDR3 domain comprising the amino acid as set forth in SEQ ID NO: 12, a CDR2 domain comprising the amino acid sequence as set forth in SEQ ID NO: 11, and a CDR1 domain comprising the amino acid sequence as set forth in SEQ ID NO: 10. The antibody may further be an IgG1 or an IgG4 isotype.

In one embodiment, the present invention is directed to an antibody, or an antigen binding fragment thereof, having antigen binding regions of antibody ST3G12. In one embodiment, the invention provides an antibody, or antigen-binding fragment thereof, comprising a heavy chain variable domain sequence as set forth in SEQ ID NO: 3, and a light chain variable domain sequence as set forth in SEQ ID NO: 4. In one embodiment, the invention is directed to an antibody having a heavy chain variable domain comprising the CDRs of SEQ ID NO: 3, and a light chain variable domain comprising the CDRs of SEQ ID NO:4. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 3, and comprises a light chain variable region having an amino acid sequence that is at least 95% identical, at least 96% identical, at least 97% identical, at least 98% identical, or at least 99% identical to the sequence set forth in SEQ ID NO: 4. In one embodiment, the invention features an anti-STAT3 antibody, or an antigen-binding portion thereof, comprising a heavy chain variable region comprising a CDR3 domain comprising the amino acid as set forth in SEQ ID NO: 15, a CDR2 domain comprising the amino acid sequence as set forth in SEQ ID NO: 14, and a CDR1 domain comprising the amino acid sequence as set forth in SEQ ID NO: 13; and comprising a light chain variable region comprising a CDR3 domain comprising the amino acid as set forth in SEQ ID NO: 18, a CDR2 domain comprising the amino acid sequence as set forth in SEQ ID NO: 17, and a CDR1 domain comprising the amino acid sequence as set forth in SEQ ID NO: 16. The antibody may further be an IgG1, IgG2, IgG2 or IgG4 isotype. In particular embodiments, the antibody is an IgG1 or an IgG4 isotype.

It should be noted that throughout, antibodies (and corresponding sequences) are referred to interchangeably with or without a "ST" preceding the name. For example, the antibody name "ST1A5" is also referred to herein as "1A5".

Antigen-binding fragments of antigen binding proteins of the invention may be produced by conventional techniques. Examples of such fragments include, but are not limited to, Fab and F(ab')2 fragments.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical, to the amino acid sequences selected from the group consisting of SEQ ID NOs. 1 or 3, and that has a light chain variable domain sequence that is at least 95% identical, at least 96% identical, at least 97% identical, at least 98% identical, or at least 99% identical, to the amino acid sequence selected from the group consisting of SEQ ID NOs. 2 or 4.

Preferably, the fully human antibody Fab fragment has both a heavy chain variable domain region and a light chain variable domain region wherein the antibody has a heavy chain/light chain variable domain sequence selected from SEQ ID NO. 1/SEQ ID NO. 2 or SEQ ID NO. 3/SEQ ID NO. 4.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical, to the amino acid sequences selected from SEQ ID NO. 1 or SEQ ID NO. 3, and that has a light chain variable domain sequence that is at least 95% identical, at least 96% identical, at least 97% identical, at least 98% identical, or at least 99% identical, to the amino acid sequence selected from SEQ ID NO:2 or SEQ ID NO:4. In one embodiment, the fully human single chain antibody has both a heavy chain variable domain region and a light chain variable domain region, wherein the single chain fully human antibody has a heavy chain/light chain variable domain sequence selected from SEQ ID NO. 1/SEQ ID NO. 2 or SEQ ID NO. 3/SEQ ID NO. 4.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) (SEQ ID Nos. 5 and 6, respectively) in the hinge region (Bloom et al., 1997, *Protein Science* 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

Thus, the invention also includes, in certain embodiments, variable sequences having at least 95% identity to those sequences disclosed herein.

In certain embodiments, an antibody, or antigen-binding fragment thereof, provided herein has a dissociation constant ($K_D$) of $1\times10^{-6}$ M or less; $5\times10^{-7}$ M or less' $1\times10^{-7}$ M or less; $5\times10^{-8}$ M or less; $1\times10^{-8}$ M or less; $5\times10^{-9}$ M or less; or $1\times10^{-9}$ M or less. In one embodiment, the antibody, or antigen-binding fragment thereof, of the invention as a $K_D$ from $1\times10^{-7}$ M to $1\times10^{-10}$ M. In one embodiment, the antibody, or antigen-binding fragment thereof, of the invention as a $K_D$ from $1\times10^{-8}$ M to $1\times10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)).

According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

In particular embodiments, antigen binding proteins of the present invention have a binding affinity ($K_a$) for STAT3 of at least $10^6$ M$^{-1}$. In other embodiments, the antigen binding proteins exhibit a $K_a$ of at least $10^7$ M$^{-1}$, at least $10^8$ M$^{-1}$, at least $10^9$ M$^{-1}$, or at least $10^{10}$ M$^{-1}$. In particular embodiments, antigen binding proteins of the present invention have a binding affinity ($K_a$) for STAT3 of $10^6$ M$^{-1}$ or less. In other embodiments, the antigen binding proteins exhibit a $K_a$ of $10^7$ M$^{-1}$ or less, $10^8$ M$^{-1}$ or less, $10^9$ M$^{-1}$ or less, $10^{10}$ M$^{-1}$ or less. In another embodiment, the antigen binding protein exhibits a $K_a$ substantially the same as that of an antibody described herein in the Examples.

In another embodiment, the present disclosure provides an antigen binding protein that has a low dissociation rate from STAT3. In one embodiment, the antigen binding protein has a $K_{off}$ of $1\times10^{-4}$ to $^{-1}$ sec$^{-1}$ or lower. In another embodiment, the $K_{off}$ is $5\times10^{-5}$ to $^{-1}$ sec$^{-1}$ or lower. In another embodiment, the $K_{off}$ is substantially the same as an antibody described herein. In another embodiment, the antigen binding protein binds to STAT3 with substantially the same $K_{off}$ as an antibody described herein.

In another aspect, the present disclosure provides an antigen binding protein that inhibits an activity of STAT3. In one embodiment, the antigen binding protein has an IC$_{50}$ of 1000 nM or lower. In another embodiment, the IC$_{50}$ is 100 nM or lower; in another embodiment, the IC$_{50}$ is 10 nM or lower. In another embodiment, the IC$_{50}$ is substantially the same as that of an antibody described herein in the Examples. In another embodiment, the antigen binding protein inhibits an activity of STAT3 with substantially the same IC$_{50}$ as an antibody described herein.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO2000/09560, incorporated by reference herein.

The present disclosure further provides multi-specific antigen binding proteins, for example, bispecific antigen binding protein, e.g., antigen binding protein that bind to two different epitopes of STAT3, or to an epitope of STAT3 and an epitope of another molecule, via two different antigen binding sites or regions. Moreover, bispecific antigen binding protein as disclosed herein can comprise a STAT3 binding site from one of the herein-described antibodies and a second STAT3 binding region from another of the herein-described antibodies, including those described herein by reference to other publications. Alternatively, a bispecific antigen binding protein may comprise an antigen binding site from one of the herein described antibodies and a second antigen binding site from another STAT3 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

Figure 1A:
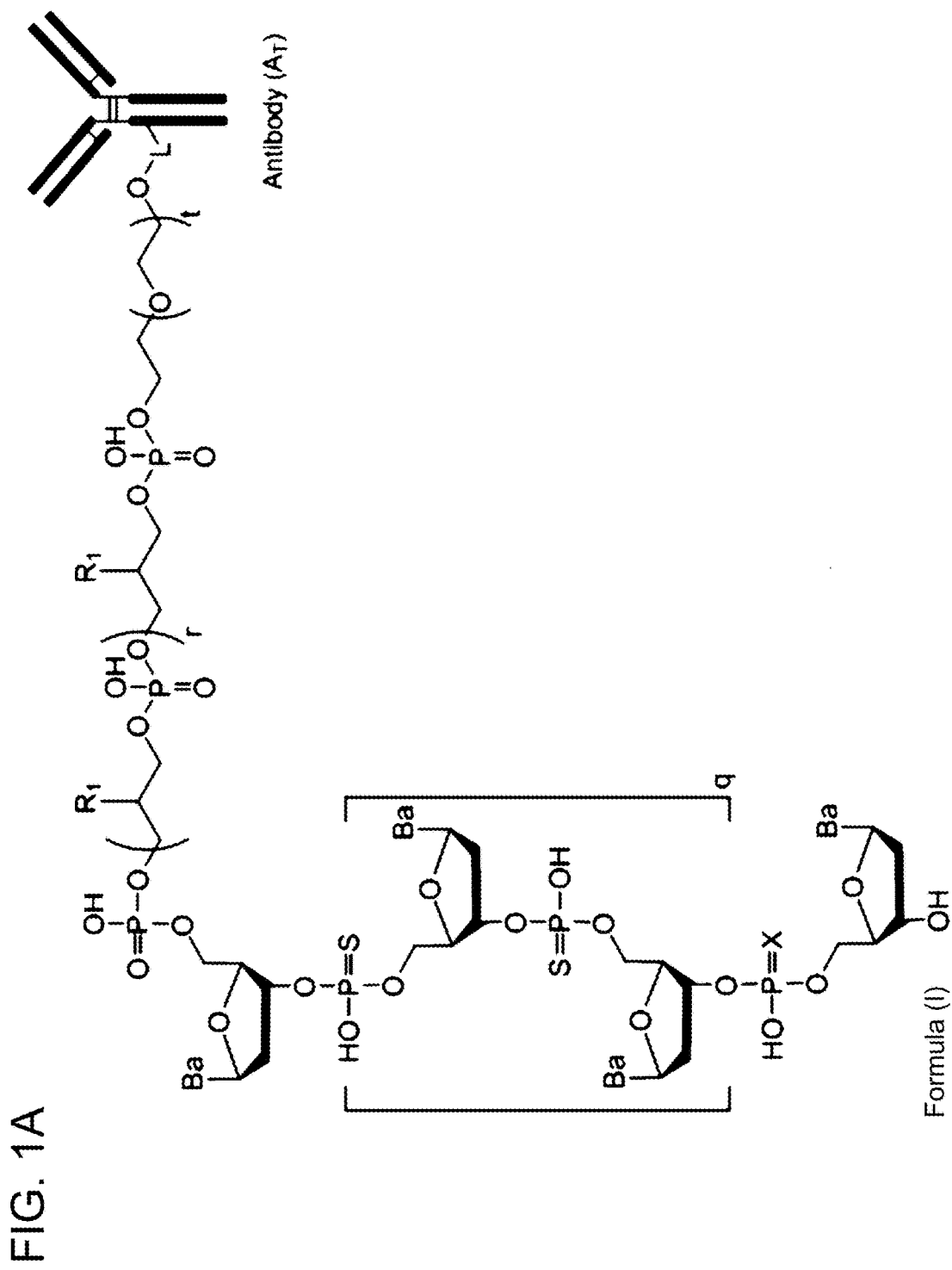
FIG. 1A is a drawing of an exemplary antibody conjugate of the present invention, comprising Formula (I), or a pharmaceutically acceptable salt thereof, wherein each of X, q, Ba, R1, r, t, L, and AT are as defined and described in PCT/US2016/057576, incorporated by reference in its entirety herein.

In certain embodiments, the anti-STAT3 antibody, or an antigen-binding fragment thereof is conjugated to an intracellular delivery compound. In one embodiment, the invention provides the compound of FIG. 1A or FIG. 1B. FIG. 1A is a drawing of an exemplary antibody conjugate of the present invention, comprising Formula (I), or a pharmaceutically acceptable salt thereof, wherein each of X, q, Ba, R1, r, t, L, and $A_T$ are as defined and described in PCT/US2016/057576, incorporated by reference in its entirety herein.

In one embodiment, the invention provides a compound having the Formula I:

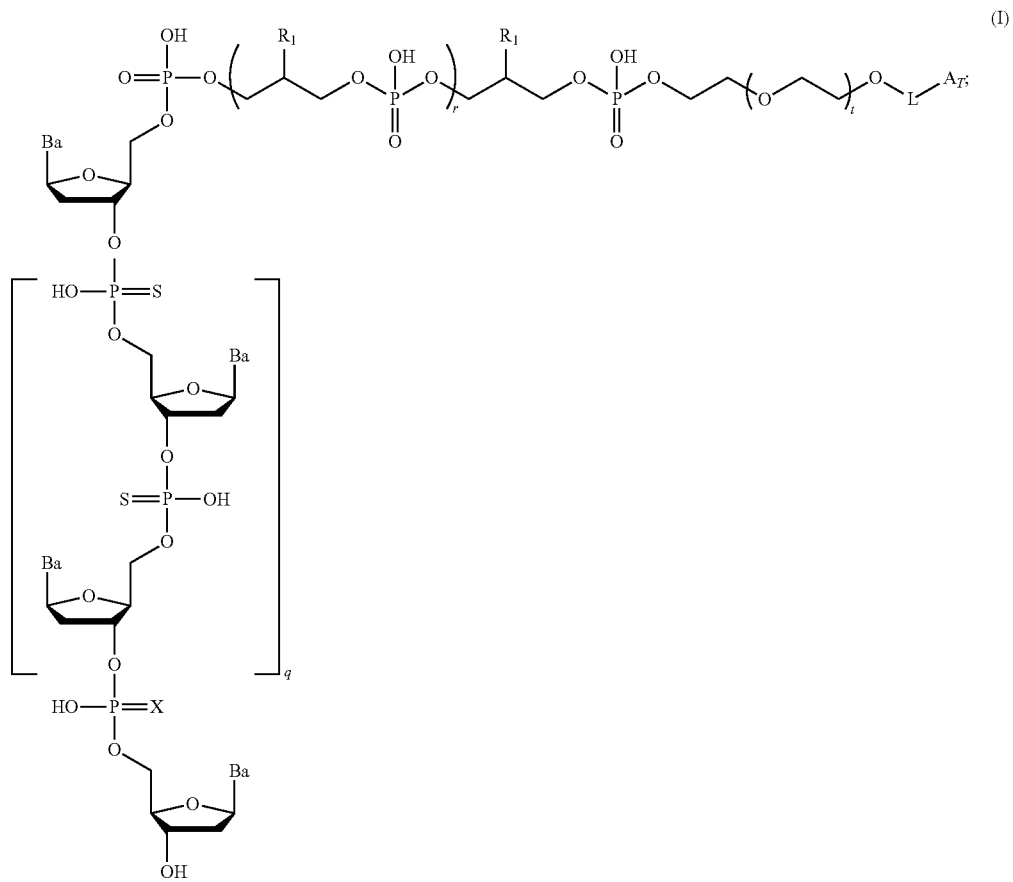

wherein, each Ba is independently selected from adenine (A), guanine (G), cytosine (C), and thymine (T);

X is O or S;

each $R^1$ is independently selected from hydrogen and $(C_1-C_6)$alkyl substituted with a fluorophore;

q is an integer from 12 to 35;

r is an integer from 1 to 10;

t is an integer from 1 to 10;

L is —$CH_2$—$R^2$—*;

$R^2$ is —$(C_1-C_6)$alkyl substituted with 1 or 2 groups selected from —C(=O)$NR^a$, —$NR^aC$(=O)$R^b$, —$NR^aC$(=O)$R^d$, =$NOR_e$, —$NR^a$, —$NR^aR^b$, —$OR^b$, —S(O)$_kR^b$, —$NR^aS(O)_2R^b$, —S(O)$_2NR^aR^b$, —S(O)$_2NR^a$, —C(=O)$OR^b$, —OC(=O)$OR^b$, —OC(=O)$R^b$, —C(=O)$NR^aR^b$, —$NR^aC$(=O)$R^b$, —$NR^aC$(=O)$OR^b$, —OC(=O)$NR^aR^b$, phenyl, —OC(=O)NR$^a$, —NR$^a$C(=O)NR$^a$R$^b$, —NR$^a$C(=O)NR$^a$, —NR$^a$(C=S)NR$^a$R$^b$, —NR$^a$(C=S)NR$^a$, and —C(=O)R$^b$;

k is 0, 1, or 2;

each R$^a$ is independently hydrogen or (C$_1$-C$_6$)alkyl optionally substituted with R$^f$;

each R$^b$ is independently (C$_1$-C$_6$)alkyl optionally substituted with R$^f$ or —C(=O)R$^f$;

R$^d$ is —[(C$_1$-C$_6$)alkyl-O—(C$_1$-C$_6$)alkyl]$_v$C(=O)NH;

R$^e$ is —[(C$_1$-C$_6$)alkyl-O—(C$_1$-C$_6$)alkyl]$_p$C(=O);

each R$^f$ is independently

[chemical structures: triazolyl groups with ring A, substituted with R$^g$]

wherein the wavy bond indicates the point of attachment to the (C$_1$-C$_6$)alkyl defined by R$^a$, or the (C$_1$-C$_6$)alkyl or carbonyl each defined by R$^b$;

R$^g$ is (C$_1$-C$_6$)alkyl or —[(C$_1$-C$_6$)alkyl-O—(C$_1$-C$_6$)alkyl]$_w$C(=O)NH;

ring A is

[chemical structures: dibenzazepine-type structure or bicyclic cyclopropane-fused ring]

wherein the dashed bonds indicate the points of attachment to the triazolyl of R$^f$, and the wavy bond indicates the point of attachment to the (C$_1$-C$_6$)alkyl defined by R$^a$, or the (C$_1$-C$_6$)alkyl or carbonyl each defined by R$^b$;

p is an integer from 1 to 10;

v is an integer from 1 to 10;

w is an integer from 2 to 12;

* indicates the point of attachment to A$_T$; and

A$_T$ is an antibody.

Figure 1B:
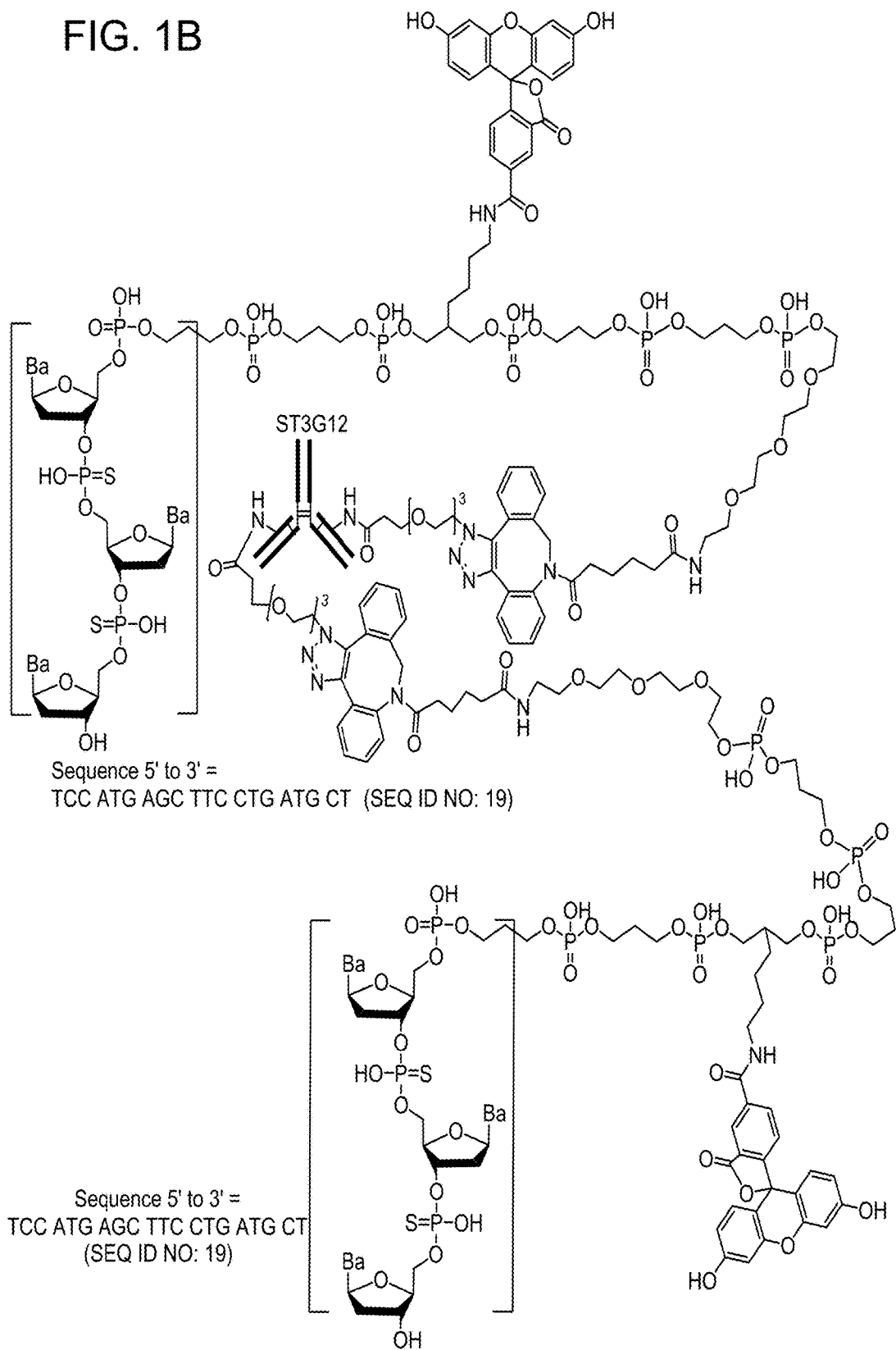
FIG. 1B is a drawing of an exemplary antibody conjugate of the present invention, Compound 901a, where the antibody ($A_T$) is ST3G12 and one $R^1$ in FIG. 1A is an alkylfluorophore moiety, and which is tested in Example 5.

In one embodiment, the antibody conjugate is the structure shown in FIG. 1B. FIG. 1B is a drawing of an exemplary antibody conjugate of the present invention, Compound 901a, where the antibody (AT) is ST3G12 and one R1 in FIG. 1A is an alkylfluorophore moiety. Compound 901a is tested in Example 5.

Figure 1C:
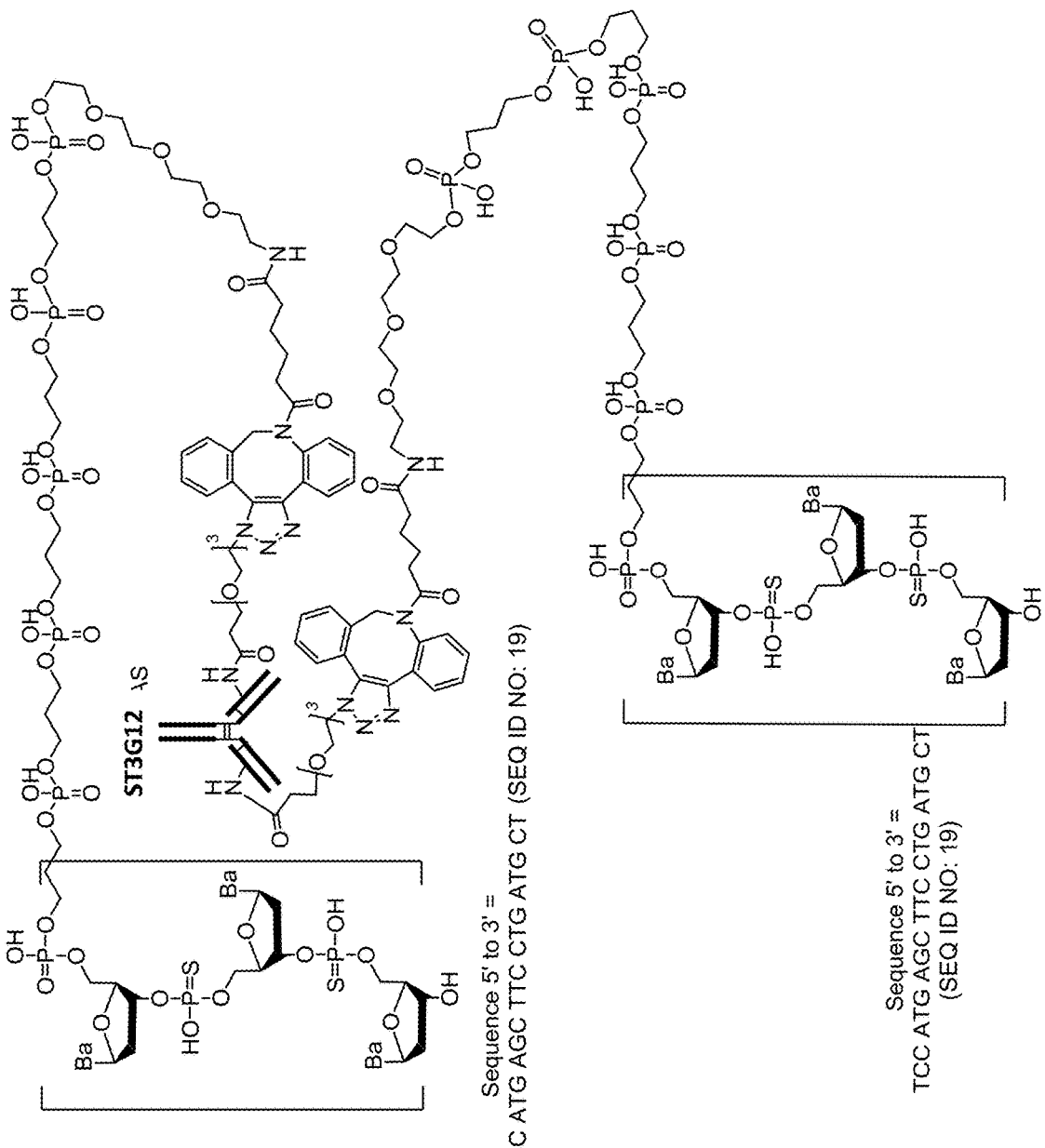
FIG. 1C is a drawing of an exemplary antibody conjugate of the present invention, Compound 901, where the antibody ($A_T$) is ST3G12 and each $R^1$ in FIG. 1A is hydrogen, and which is tested in Examples 2-10.

In one embodiment, the antibody conjugate is the structure shown in FIG. 1C. FIG. 1C is a drawing of an exemplary antibody conjugate of the present invention, Compound 901, where the antibody (AT) is ST3G12 and each R1 in FIG. 1A is hydrogen. Compound 901 is tested in Examples 2-10.

Oligomers that contain one or more antigen binding proteins may be employed as STAT3 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have STAT3 binding activity.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-STAT3 antibody fragment or derivative fused to a leucine zipper peptide are expressed in suitable host cells, and the soluble oligomeric anti-STAT3 antibody fragments or derivatives that form are recovered from the culture supernatant.

Antigen binding proteins directed against STAT3 can be used, for example, in assays to detect the presence of STAT3 polypeptides, either in vitro or in vivo. The antigen binding proteins also may be employed in purifying STAT3 proteins by immunoaffinity chromatography. Blocking antigen binding proteins can be used in the methods disclosed herein. Such antigen binding proteins that function as STAT3 antagonists may be employed in treating any STAT3-induced condition, including but not limited to various cancers.

Antigen binding proteins may be employed in an in vitro procedure, or administered in vivo to inhibit STAT3-induced biological activity. Disorders that would benefit (directly or indirectly) from activation of STAT3, examples of which are provided herein, thus may be treated. In one embodiment, the present invention provides a therapeutic method comprising in vivo administration of a STAT3 blocking antigen binding protein to a mammal in need thereof in an amount effective for reducing a STAT3-induced biological activity.

In certain embodiments of the invention, antigen binding proteins include fully human monoclonal antibodies that inhibit a biological activity of STAT3.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of STAT3 bound thereto. Polypeptides contemplated for use herein include substantially homogeneous recombinant mammalian anti-STAT3 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-STAT3 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

STAT3-binding polypeptides can also be produced by chemical synthesis (such as by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to STAT3. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen-binding fragments of antigen binding proteins of the invention may be produced by conventional techniques known in the art.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_n-CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Methods, Formulations and Modes of Administration

Any of the antibodies or antigen binding fragments disclosed herein may be used in such therapeutic methods.

The present disclosure further provides a method for treating a disease or condition that can be characterized by aberrant cell proliferation, such as cancer, comprising administering an anti-STAT3 antigen binding protein selected from the group consisting of a fully human antibody of an IgG class that binds to a STAT3 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connecting the heavy chain and light chain variable domain regions, including the heavy and light chain variable regions described in SEQ ID Nos. 1-4 or CDR domains as described in SEQ ID NOs 7-18 in Table 4.

Examples of anti-STAT3 antibodies and antigen binding fragments that may be used in the therapeutic methods and compositions of the invention are described above.

In one embodiment, the anti-STAT3 antibodies and antibody fragments of the invention are used to treat cancer. As discussed above, the anti-STAT3 antibodies and antibody fragments of the invention can be used in the treatment or prevention of any disease or condition that can be characterized by aberrant cell proliferation, for example, cancer. Many human solid and hematological tumors harbor constitutive STAT3 activity (Yue et al. Expert Opin Investig Drugs. 2009 January; 18(1): 45-56). Accordingly, any cancer with constitutive STAT3 activity can be treated by the antibodies and antigen binding fragments of the invention.

In certain embodiments, the cancer is a solid tumor. In other embodiments, the cancer is selected from the group consisting of melanoma, glioma, medulloblastoma, renal cell carcinoma, pancreatic adenocarcinoma, ovarian carcinoma, rhabdomyosarcoma, osteosarcoma, glioblastoma, breast, pancreas, ovarian, prostate, lung, liver, colon, colorectal, gastric, head, neck, and kidney. In one embodiment, the cancer is a hematological cancer. In another embodiment, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia, and large granular lymphocyte leukemia.

In one embodiment, the anti-STAT3 antibodies and antibody fragments of the invention can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more anti-STAT3 antibodies and antibody fragments of the invention can be administered, together (simultaneously) or at different times (sequentially). In addition, anti-STAT3 antibodies and antibody fragments of the invention can be administered with another type of compounds for treating cancer or for inhibiting angiogenesis.

In certain embodiments, the anti-STAT3 antibodies and antibody fragments of the invention can be used alone.

In certain embodiments, the anti-STAT3 antibodies and antibody fragments of the invention can be labeled or unlabeled for diagnostic purposes. Typically, diagnostic assays entail detecting the formation of a complex resulting from the binding of a binding polypeptide to STAT3. The anti-STAT3 antibodies and antibody fragments of the invention can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding proteins can be used in assays, such as agglutination assays. Unlabeled binding proteins can also be used in combination with another (one or more) suitable reagent which can be used to detect the binding polypeptide, such as a labeled antibody reactive with the binding protein or other suitable reagent (e.g., labeled protein A).

Techniques and dosages for administration vary depending on the type of specific binding protein and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions comprising the antigen binding proteins of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

Thus, the anti-STAT3 antibody, or antigen binding portion thereof, of the invention can be incorporated into a pharmaceutical composition suitable for parenteral administration. Preferably, the anti-STAT3 antibody, or antigen binding portion thereof, will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, an anti-STAT3 antibody, or antigen binding portion thereof, described herein is administered by intravenous infusion or injection. In another preferred embodiment, an anti-STAT3 antibody, or antigen binding portion thereof, is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The anti-STAT3 antibody, or antigen binding portion thereof, of the present invention can be administered by a variety of methods known in the art, although for many therapeutic applications, the preferred route/mode of administration is subcutaneous injection, intravenous injection, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., (Marcel Dekker, Inc., New York, 1978).

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

Other embodiments are described in the following non-limiting Examples.

EXAMPLES

Example 1. Anti-STAT3 Antibody Sequences

Recombinant human antibodies specific for human STAT3 were identified and selected for therapeutic characteristics, including specificity for human STAT3 and a high affinity for STAT3 (e.g., $K_D$ of $10^{-6}$ M or less).

The amino acid sequences of the heavy and light chain variable domains of the identified anti-STAT3 antibodies (referred to as antibodies ST1A5 and ST3G12), and their complementary determining regions (CDRs), are described in Table 1.

TABLE 1

| Amino acid sequences of heavy and light chain variable domains and CDRs | | |
|---|---|---|
| Antibody | Description | Amino Acid sequence and identifier |
| ST1A5 | Heavy chain variable domain | EVQLVESGAEVKKPGASVKVSCKASGYTFTGYYMHWVRQAPGQGLEWMGWINPNSGGTNYAQKFQGRVTMTRDTSISTAYMELSRLRSDDTAVYYCARDGGLGWGTYFRLGDAFDIWGQGTMVTVSS (SEQ ID NO: 1) |
| ST1A5 | Heavy chain variable domain CDR1 | GYTFTGYY (SEQ ID NO: 7) |
| ST1A5 | Heavy chain variable domain CDR2 | INPNSGGT (SEQ ID NO: 8) |
| ST1A5 | Heavy chain variable domain CDR3 | ARDGGLGWGTYFRLGDAFDI (SEQ ID NO: 9) |
| ST1A5 | Light chain variable domain | QSVLTQPPSVSKGLRQTATLTCTGNSNNVGNEGAAWLQQHQGHPPKLLSYRNFNRPSGISERFSASRSGNTASLTITGLQPEDEADYYCSAWDSSLSAWVFGGGTKLTVL (SEQ ID NO: 2) |
| ST1A5 | Light chain variable domain CDR1 | SNNVGNEG (SEQ ID NO: 10) |
| ST1A5 | Light chain variable domain CDR2 | RNF (SEQ ID NO: 11) |
| ST1A5 | Light chain variable domain CDR3 | SAWDSSLSAWV (SEQ ID NO: 12) |
| ST3G12 | Heavy chain variable domain | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARSDYVHSFDIWGQGTMVTVSS (SEQ ID NO: 3) |
| ST3G12 | Heavy chain variable domain CDR1 | GYTFTSYY (SEQ ID NO: 13) |
| ST3G12 | Heavy chain variable domain CDR2 | INPSGGST (SEQ ID NO: 14) |
| ST3G12 | Heavy chain variable domain CDR3 | ARSDYVHSFDI (SEQ ID NO: 15) |

TABLE 1-continued

Amino acid sequences of heavy and light chain variable domains and CDRs

| Antibody | Description | Amino Acid sequence and identifier |
|---|---|---|
| ST3G12 | Light chain variable domain | QPVLTQPPSASALLGASIKLTCTLSS EHSTYTVEWYQQRPGRSPQYIMNV KSDGSYNKGDGIPDRFMGSSSGAD RYLTFSNLQSDDEAEYHCGESHRID GQVGVVFGGGTKLTVL (SEQ ID NO: 4) |
| ST3G12 | Light chain variable domain CDR1 | SEHSTYT (SEQ ID NO: 16) |
| ST3G12 | Light chain variable domain CDR2 | VKSDGSY (SEQ ID NO: 17) |
| ST3G12 | Light chain variable domain CDR3 | GESHRIDGQVGVV (SEQ ID NO: 18) |

Example 2. STAT3 Antibody Binding

Three anti-STAT3 antibodies, i.e., ST1A5, ST3G12, ST5G12, were expressed and purified. The designations 1A5, 3G12 and 5G12 refer to ST1A5, ST3G12 and ST5G12, respectively, and are used interchangeably throughout.

Figure 2A:
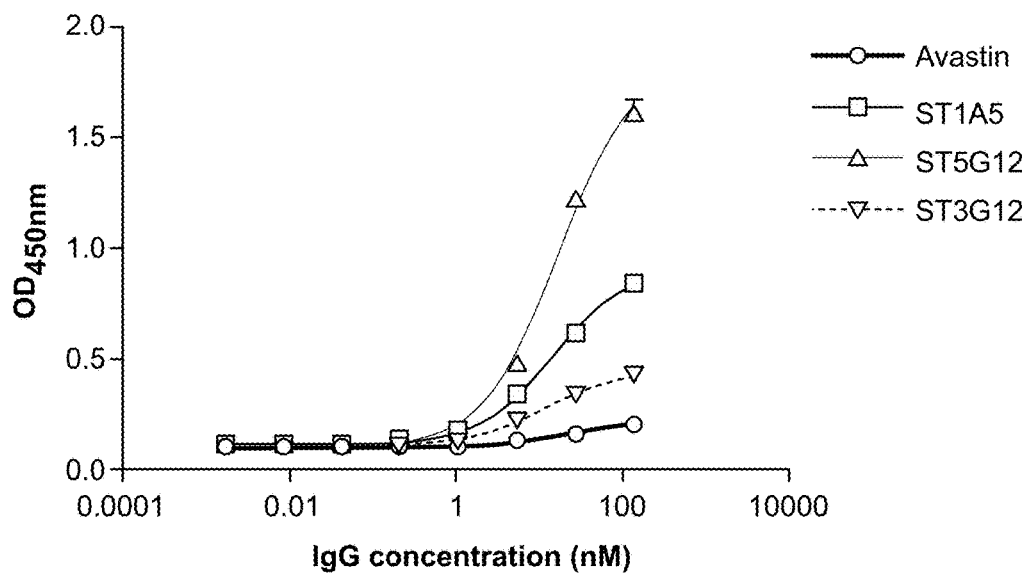
FIG. 2A is a graph that shows the results of an ELISA assay used to assess the binding of the anti-STAT3 antibody clones ST1A5, ST3G12 and ST5G12 to cellular antigens in U251 malignant glioblastoma cells. Bevacizumab (Avastin), a monoclonal antibody that inhibits vascular endothelial growth factor A (VEGF-A) was used as a negative control.
Figure 2B:
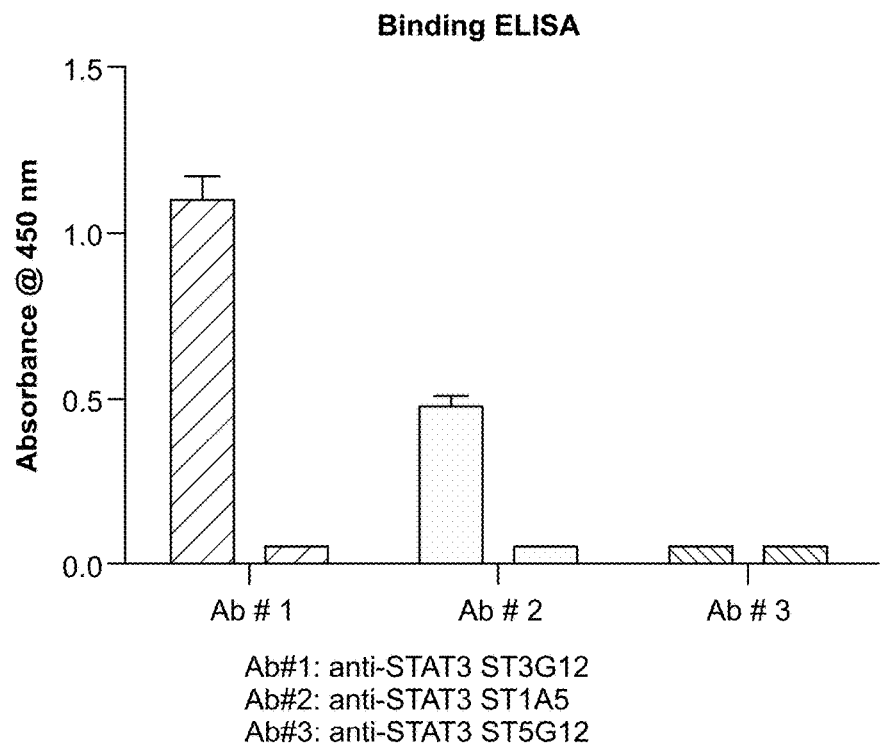
FIG. 2B is a graph that shows the results of an ELISA assay that was used to assess the binding of fully human anti-STAT3 monoclonal antibodies to antigen (recombinant human STAT3 protein). Ab#1 corresponds to anti-STAT3 antibody ST3G12, Ab#2 corresponds to anti-STAT3 antibody ST1A5 and Ab#3 corresponds to anti-STAT3 antibody ST5G12.

Binding of antibody clones ST1A5, ST3G12, ST5G12 was tested in an enzyme-linked immunosorbant assay (ELISA) assay to assess the binding of the candidate anti-STAT3 antibodies to recombinant human STAT3 proteins. U251 malignant glioblastoma cells were seeded overnight in a 96 well plate. Cells were fixed with paraformaldehyde (PFA) and permeabilized with Triton reagent, and then incubated with serial dilutions of the antibody candidates for one hour. Following incubations, cells were washed and incubated for 30 minutes with horseradish peroxidase (HRP) conjugated anti-human IgG. Chemiluminescence was measured on a plate reader. Bevacizumab (Avastin), a monoclonal antibody that inhibits vascular endothelial growth factor A (VEGF-A) was used as a negative control. The results are shown in FIG. 2A. FIG. 2B shows the results of an ELISA assay that was performed to assess the binding of fully human anti-STAT3 monoclonal antibodies to antigen (recombinant human STAT3 protein). Ab#1, #2 and #3 indicates the STAT3 clone ST3G12, ST1A5 and ST5G12, respectively. FIG. 2B demonstrates the sensitivity and the specificity for STAT3 of the anti-STAT3 antibodies ST1A5, ST3G12 and ST5G12.

Figure 3A:
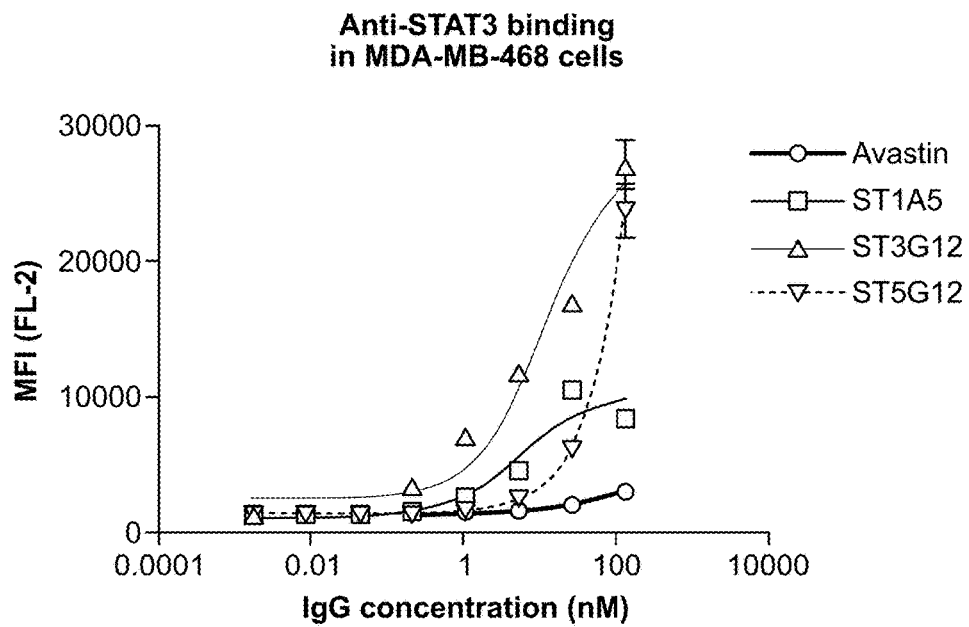
FIG. 3A is a graph that shows the results of a cell binding assay to assess binding of anti-STAT3 antibodies ST1A5, ST3G12 and ST5G12 to cellular antigens in MDA-MB-468 cells at increasing antibody concentrations (nM). MFI refers to the mean fluorescent intensity that was detected. Bevacizumab (Avastin), a monoclonal antibody that inhibits vascular endothelial growth factor A (VEGF-A) was used as a negative control.
Figure 3B:
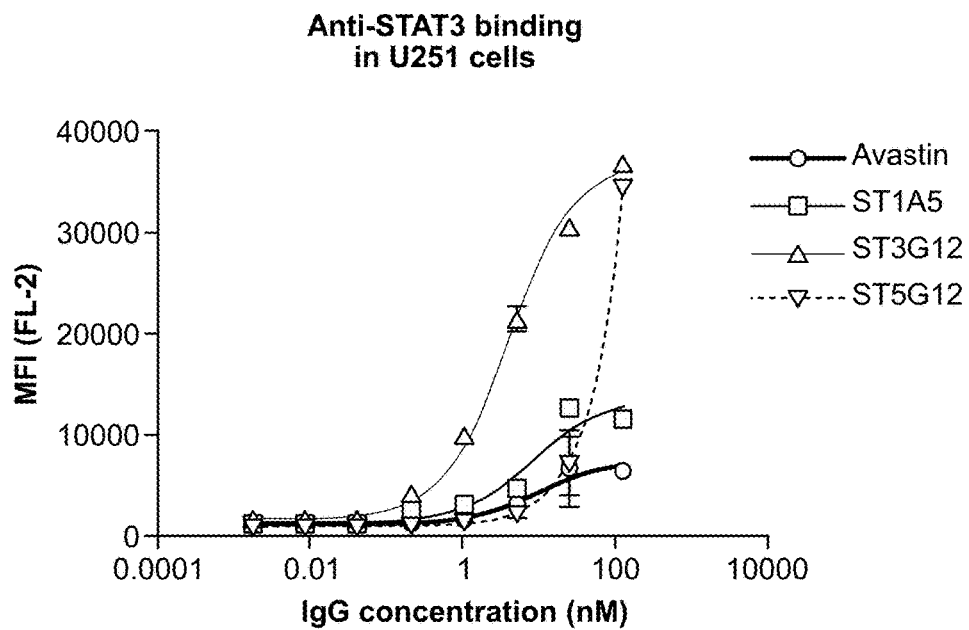
FIG. 3B is a graph that shows the results of a cell binding assay to assess binding of anti-STAT3 antibodies ST1A5, ST3G12 and ST5G12 to antigens in U251 cells at increasing antibody concentrations (nM). Bevacizumab (Avastin), a monoclonal antibody that inhibits vascular endothelial growth factor A (VEGF-A) was used as a negative control.

Next, the binding of the candidate anti-STAT3 antibodies to cellular targets was tested in cell binding assays using MDA-MB-435 breast cancer cells and U251 cells. The cells were seeded overnight in a 96 well plate, then fixed with PFA and permeabilized with methanol. Cells were incubated with serial dilutions of the anti-STAT3 antibody candidates ST1A5, ST3G12 and ST5G12 for one hour and 30 minutes. Following incubation, the cells were washed and incubated for 30 minutes with phycoerythrin (PE) conjugated anti-human IgG. Fluorescence was measured on an Intellicyte high-throughput flow cytometry analyzer. The results, shown in FIG. 3A and, FIG. 3B demonstrate that this assay was specific and sensitive for STAT3. FIG. 3A shows binding of the anti-STAT3 antibodies ST1A5, ST3G12 and ST5G12 in MDA-MB-468 cells (breast cancer cell line) and FIG. 3B shows binding of the anti-STAT3 antibodies ST1A5, ST3G12 and ST5G12 in U251 cells (glioblastoma). Bevacizumab (Avastin), a monoclonal antibody that inhibits vascular endothelial growth factor A (VEGF-A) was used as a negative control. As shown in FIGS. 3A and 3B, the anti-STAT3 antibodies ST5G12 and ST3G12 both bound STAT3, with ST5G12 being an especially strong binder. The ST1A5 antibody did not show strong STAT3 binding to MDA-MB-468 and U251 cells in comparison to antibodies ST5G12 and ST3G12.

Figure 3C:
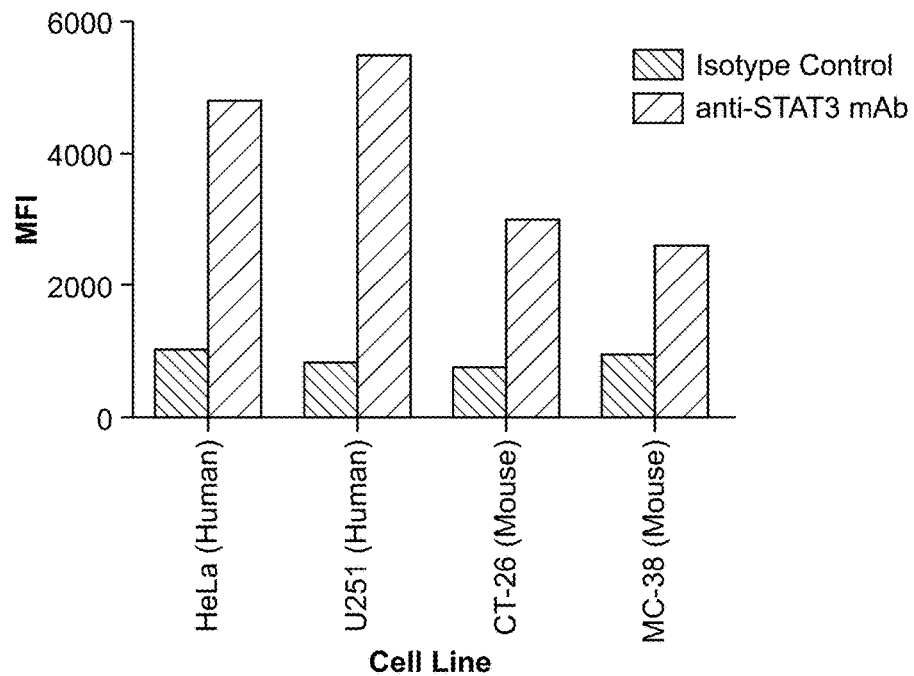
FIG. 3C is a graph that shows binding of anti-STAT3 monoclonal antibody to human cell lines HeLa and U251, and to mouse cell lines CT-26 and MC-38. An isotype control was used as a negative control.

FIG. 3C shows binding of the anti-STAT3 monoclonal antibodies ST3G12 to human cell lines HeLa and U251, and to mouse cell lines CT-26 and MC-38. An isotype control was used as a negative control. The experimental procedure was the same as described above for FIGS. 3A and 3B. As shown in FIG. 3C, the anti-STAT3 monoclonal antibody showed strong binding to the human HeLa and U251 cell lines, and also was able to recognize mouse STAT3 in the CT-26 and MC-38 mouse cell lines.

Figure 4:
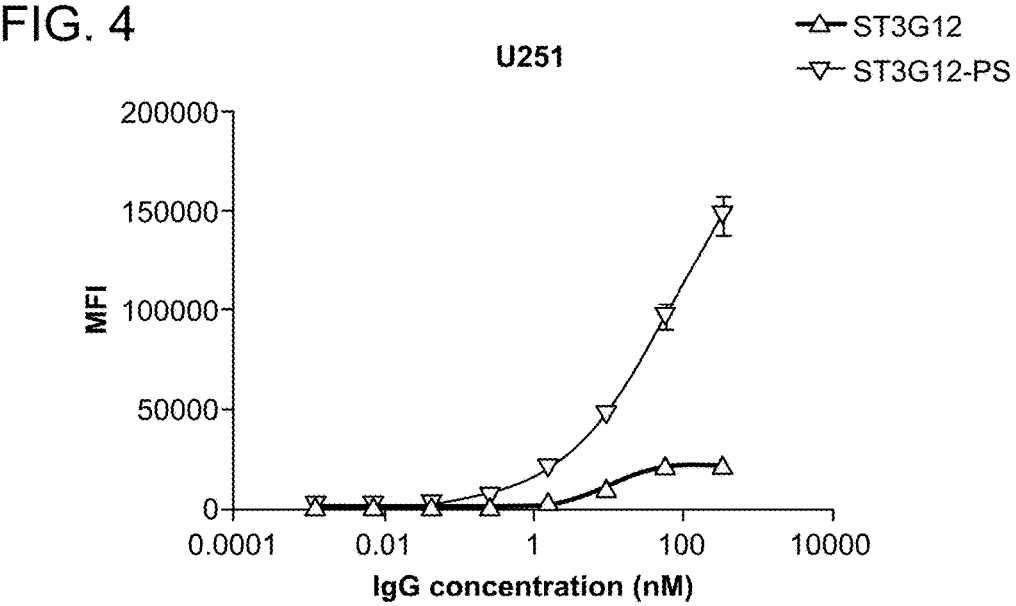
FIG. 4 is a graph that shows the results of a cell binding assay to assess binding of naked anti-STAT3 ST3G12 antibodies (ST3G12) and oligosaccharide (PS) conjugated anti-STAT3 ST3G12 antibodies (designated as "PS-STAT3") to cellular antigens in U251 cells at increasing antibody concentrations (nM).

Cell binding of naked anti-STAT3 ST3G12 antibodies (ST3G12) versus compound 901 (ST3G12-PS) was assessed in U251 cells. Cells were lifted, permeabilized and incubated with increasing amounts of naked anti-STAT antibodies and PS anti-STAT antibody (compound 901) in PBS+/− 2% fetal bovine serum (FBS). After 45 minutes at room temperature, cells were washed twice and incubated with phycoerythrin (PE) conjugated-anti-human IgG for 20 minutes at room temperature in the dark. Cells were then washed and analyzed by high throughput flow cytometry (HTFC). The results are shown in FIG. 4 for assessment of antibody binding to U251 cells. As described in FIG. 4, binding of the naked anti-STAT3 antibody, ST3G12, was considerably lower than that of the conjugated anti-STAT3 antibody, ST3G12-PS (compound 901). For the ST3G12-PS antibody conjugate (compound 901), higher binding was detected in each cell line relative to the naked antibody, independent of the level of STAT3 expression.

Next, binding affinity of the anti-STAT3 antibodies (naked and PS conjugated compound 901 labeled below as anti-STAT3-PS) was determined. Biacore T200 was used to measure the affinity of anti-STAT and anti-STAT-phosphorothioate (PS) antibody (compound 901) to human STAT3. Anti-human Fc antibody (GE, BR-1008-39) was immobilized on a CM5 sensor chip to approximately 1000 RU using standard NHS/EDC coupling methodology. Antibodies (approximately 10 ug/ml) were captured for 60 seconds at a flow rate of 10 ul/min Recombinant human STAT3-GST was serially diluted 2-fold into running buffer (HBS-EP+, starting from 100 nm). All measurements were conducted at a flow rate of 30 ul/min Surfaces were regenerated with 3M MgCl$_2$ (from human antibody kit) for 60 seconds. A 1:1 (Langmuir) binding model was used to fit the data. The results are shown in Table 2, below for anti-STAT3 antibody, ST3G12, and the conjugated anti-STAT3 antibody, ST3G12-PS (compound 901).

TABLE 2

| Name | Ka (1/Ms) | Kd (1/s) | Rmax | KD (M) | Chi2 |
|---|---|---|---|---|---|
| Anti-STAT3 | 5.97E4 | 3.22E-4 | 174 | 5.39E-9 | 3.06 |
| Anti-STAT3-PS | 4.94E5 | 1.1E-4 | 73.1 | 2.22E-10 | 3.6 |

As described in Table 2, conjugation of the naked anti-STAT3 antibodies (compound 901) improved the affinity of the antibodies to STAT3. The data in Table 2 indicates that the conjugated antibody compound 901 ("Anti-STAT3-PS") bound the antigen with greater affinity when compared to unmodified anti-STAT3 antibody (the smaller the $K_D$, the greater the affinity of the antibody for its antigen). No binding of either the unmodified anti-STAT3 antibodies or the PS modified antibodies to GST protein was observed in the assay, suggesting that the difference in interaction rate of antigen-antibody contributes to the differential binding affinity.

Figure 5:
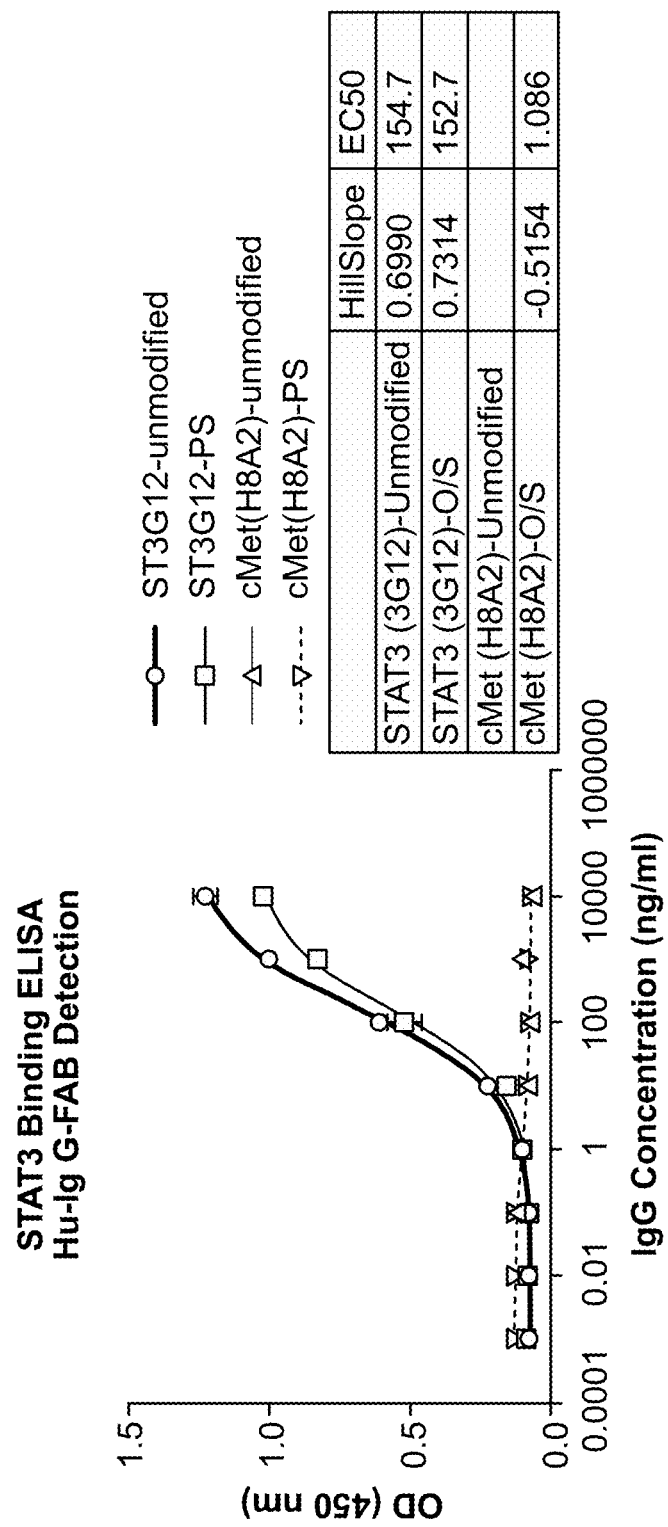
FIG. 5 is a graph that shows the results of an ELISA assay used to assess the binding of the anti-STAT3 ST3G12 antibodies that were unmodified (ST3G12-unmodified) and modified antibody conjugates (ST3G12-PS) to human IgG. Anti-cMet unmodified antibodies ((H8A2)-unmodified) and modified antibody conjugates ((H8A2)-PS) were used as controls.

The binding of the unmodified and modified antibodies (compound 901) was also tested in the STAT3 ELISA binding assay described above. The results are shown in FIG. 5 and FIG. 6. The PS modified compound 901 version of the ST3G12 antibody (ST3G12-PS) showed a slightly lower binding than the unmodified ST3G12 antibody. However, the $EC_{50}$ was the same. Given these results, it is possible that the PS modification interfered with the detection. Unmodified c-met antibody (cMet (H8A2)) and PS-modified c-met antibody (cMet(H8A2)-PS), which is compound 901 with anti-c-Met antibody, were used as a control. Anti-cMet clone H8A2 is described in WO2013192594, incorporated by reference in its entirety herein. FIG. 30 also shows results from experiments comparing the binding of the PS-modified anti-STAT3 antibody conjugate (compound 901) and anti-STAT3 monoclonal antibodies, tested in the STAT3 ELISA binding assay, described above As shown in FIG. 30, modification does not substantially affect the binding affinity between the antibody and its antigen.

Example 3. Anti-STAT3 Antibody Accumulation and Internalization

The relative STAT3 level in various test cell lines is shown in FIG. 7A and FIG. 7B. The total level of STAT3 and the level of phosphorylated STAT3 (phospho-STAT3) in human foreskin fibroblast (HFF), normal human astrocytes (NHA), normal colon fibroblasts (CCD-18CO), normal breast epithelial cells (MCF-10A), gliosblastoma (U251), triple negative breast cancer (MDA-MB-468), triple negative breast cancer (HCC1954) and ER+ breast cancer (MCF-7) is shown in FIG. 7A. Levels of phosphorylated STAT3 were determined by flow cytometry using an antibody to phospo-STAT3. Controls used were primary antibody alone, secondary antibody alone and an isotype matched control IgG. FIG. 7B shows the ratio of phosphorylated STAT3 to total STAT3 (ratio P/T STAT3) in these cells.

Normal breast epithelial cells (MCF-10A) and ER+ breast cancer cells (MCF-7) were treated with naked ST3G12 antibody and conjugated ST3G12-PS antibody (compound 901) (shown as "OS-STAT3" in FIGS. 8A and 8B) to determine the effect on STAT3 phosphorylation. Cells were pre-treated overnight with antibody, and then stimulated with various concentrations of IL-6 for 20 minutes (10 ng/ml or 40 ng/ml). IL-6 is a STAT3 activator. Cells were then lysed and the protein lysates were subjected to ELISA to determine the phosphorylation status. The results shown in FIG. 8A for MCF-10 cells, and in FIG. 8B for MCF-7 cells, demonstrate little to no effect of the naked ST3G12 antibody or the ST3G12-PS antibody conjugate compound 901 on STAT3 phosphorylation. These results suggest that the ST3G12 antibody epitope is not interfering with the STAT3 phosphorylation site. "OS-AIP" refers to an oligosaccharide conjugated bacterial AIP protein, used as a control.

MDA-MB-468 triple negative breast cancer cells, which have a high level of STAT3 activity (STAT3 high) (see FIG. 7A) were treated with 10 ug/ml of ST3G12-PS (compound 901) in increasing proportions of human serum (1%, 5%, 10% and 20%), for 90 minutes at 37° C., to induce STAT3 activation. Cells were then fixed, permeabilized and stained with anti-human IgG Alexa 546. It was found that ST3G12-PS (compound 901) accumulated in the MDA-MB-468 cells, and increasing accumulation was seen with increasing concentrations of serum.

The same experiments were repeated in the U251 glioblastoma cell line, which also has high levels of STAT3 activity, as described in FIG. 7A. U251 cells were treated with 10 ug/ml of ST3G12-PS antibody conjugate compound 901 in increasing proportions of human serum (1%, 5%, 10% and 20%), for 90 minutes at 37° C. Cells were then fixed, permeabilized and stained with anti-human IgG Alexa546. It was found that ST3G12-PS (compound 901) accumulated in the U251 cells, and increasing accumulation was seen with increasing concentrations of serum (data not shown). MCF-10A, a normal human mammary epithelial cell line with low levels of STAT3 activity (STAT3 low), was described in FIGS. 7A and 7B. This cell line was also tested according to the above protocol. It was found that ST3G12-PS (compound 901) accumulated in the MCF-10A cells with increasing serum concentrations (1%, 5%, 10% and 20% serum) (data not shown). The results of another experiment that was performed to determine accumulation of anti-STAT3 antibody conjugate (e.g. compound 901) are shown in FIG. 7C. FIG. 7C shows quantification of internalized antibodies by the number of antibody punctates in HeLa cells.

A time course experiment was carried out showing anti-ST3G12-PS (compound 901) accumulation in MDA-MB-468 cells (STAT3 high). Cells were seeded in 96 well plates overnight. 20 ug/ml of ST3G12-PS-Alexa488 antibody (compound 901-Alexa488) was added for the indicated duration of 0.5, 2, 4, 6, 8 and 24 hours. Following incubation with the antibody for the indicated time, cells were fixed and imaged using Incucyte. FIG. 9A(i) and (ii) shows that accumulation of the antibody increased as time increased. Panel (ii) shows the data from panel (i) normalized to cell count. FIG. 9B(i) and (ii) shows the same experiments, performed in MCF-10A cells (STAT3 low). The results from the experiments done with the STAT3 low MCF-10A cells were similar to those from the STAT3 high MDA-MB-468 cells, showing that accumulation of PS-ST3G12 (compound 901) increased as time increased.

FIGS. 9C and 9D show the results of ELISA experiments carried out to show that modification of the ST3G12 antibody with the PS oligomer did not affect its binding affinity. ST3G12-unmodified refers to the unmodified ST3G12 antibody and ST3G12-PS refers to the PS modified ST3G12 antibody (FIG. 9C). FIG. 9D shows the results of an ELISA experiment carried out to show that modification of the antibody did not affect its binding affinity. ST3G12-unmodified refers to the unmodified anti-STAT3 antibody and ST3G12-PS refers to the PS modified anti-STAT3 antibody (compound 901).

MDA-MB-468 triple negative breast cancer cells, which have a high level of STAT3 activity (STAT3 high) were treated with 10 ug/ml of ST3G12-PS in increasing proportions of human serum (1%, 5%, 10% and 20%), for 90 minutes at 37° C., to induce STAT3 activation. Cells were then fixed, permeabilized and stained with anti-human IgG Alexa 546. The results in 10A show that the ST3G12 conjugate accumulated in the MDA-MB-468 cells, and increased accumulation is seen with increased concentrations of serum.

Example 5. Cellular Uptake of Anti-STAT3-PS

Experiments were carried out to confirm that the ST3G12-PS antibody conjugate (compound 901) was penetrating the cells. Briefly, previously cleaned glass coverslips were coated with collagen for 2 hours at 37° C. 100,000 U251 cells were seeded on the coverslips. Media was removed, and cells were rinsed once with fluorobrite. Next, 20 ug/mL of the specified antibody was added for 2 hours at 37° C. Cells were fixed in 4% PFA for 15 minutes and then permeabilized with 0.1% TritonX for 15 minutes. Cells were blocked with 3% BSA for 30 minutes and 1:250 GAH-Alexa fluor 488 was added for 1 hour. Next, 200× wheat germ agglutinin Alexa fluor 555 (WGA 555) and 1:1000 DAPI was added for 30 minutes. Cells were washed 3× with PBS and mounted with prolong gold anti-fade. Using microscopy, it was found that cell penetration was observed from all the compound 901a and compound 901 treated samples. The negative control, the unmodified ST3G12 antibody, showed no internalization. The results are shown in FIG. 10A, FIG. 10B and FIG. 10E (for compound 901a), which use immunofluorescent detection to show that compound 901 (shown in FIGS. 10A and 10B) and compound 901a (shown in FIG. 10E) penetrated the cells. In FIG. 10B, U251 cells were treated with 10 ug/ml of ST3G12-PS antibody (compound 901) in increasing proportions of human serum (1%, 5%, 10% and 20%) for 90 minutes at 37° C. As shown in FIG. 10B, compound 901 penetrated the cells. FIG. 10E is a confocal microscopic image of ST3G12 and ST3G12-PS antibody conjugate internalization in U251 cells. In FIG. 10E, red fluorescence indicates the plasma membrane, blue fluorescence indicates the nuclei and green florescence represents the intracellular accumulated ST3G12-PS antibody conjugate compound 901a. FIG. 10C shows the results of the same experiments described in FIG. 10A, but in MCF-10A human normal breast epithelial cells with additional increasing serum concentrations. As shown in FIG. 10C, compound 901 penetrated the cells. FIG. 10D shows the microscopic images of MDA-MB-468 human breast cancer cells treated with ST3G12-PS (compound 901a) at 5 ug/mL and 10 ug/mL.

In a separate experiment (not shown), it was shown that anti-STAT3-PS antibody (compound 901) was internalized into cells and redistributed around the nucleus upon STAT3 activation. MCF-10A cells (5,000 cells/well) were incubated with no serum or 20% human serum, overnight, to induce STAT3 activation. 10 ug/ml of modified anti-STAT3 antibodies (ST3G12-PS) was added to the cells for 2 hours. Intracellular antibodies were visualized by an EVOS microscope of cells stained with anti-human IgG conjugated to Alexa546.

FIGS. 11A and 11B show the effect of temperature of internalization of ST3G12-PS antibody conjugate. FIG. 11A shows the effect of temperature on internalization of ST3G12-PS antibody conjugate in U251 cells. U251 cells were incubated with ST3G12-PS anti-STAT3 antibody compound 901 with an Alexa flour NHS 488 label at a concentration of 10 ug/ml. The results are shown as the number of green objects/mm$^2$, corresponding to the number of cells that internalized the antibody conjugate, over time, at 4° C. and 37° C. In FIG. 11A, internalization of ST3G12-PS in U251 cells appeared to peak at about 45-60 minutes for 37° C. and about 300 minutes for 4° C. FIG. 11B is a graph that shows the effect of temperature on internalization of the ST3G12-PS antibody conjugate compound 901 in MDA-MB-468 cells. MDA-MB-468 cells were incubated with ST3G12-PS antibody conjugate with an Alexa flour NHS 488 label (compound 901-Alexa488) at a concentration of 10 ug/ml. The results are shown as the number of green objects, corresponding to the number of cells that internalized the antibody conjugate, over time, at 4° C. and 37° C. In FIG. 11B, internalization of ST3G12-PS in MDA-MB-468 cells appeared to peak at about 240 minutes for 37° C. and about 120 minutes for 4° C.

A time course analysis was also carried out to determine the cellular uptake of ST3G12-PS antibody conjugate compound 901. MDA-MB-468 (STAT3 high) and MCF-10A (STAT3 low) cells were seeded in 96 well plates at a concentration of 5000 cells/well. Twenty four hours later, 20 ug/ml of modified anti-STAT3 antibody compound 901 labeled with Alexa 488 were added to the cells for the following durations: 0.5 hours, 2 hours, 4 hours, 6 hours, 8 hours and 24 hours. Cells were then fixed and imaged using Incucyte. FIG. 12A shows ST3G12-PS (compound 901) accumulated in MDA-MB-436 cells. FIG. 12B shows ST3G12-PS (compound 901) accumulated in MCF-10A cells. In both cell lines, accumulation appeared to peak at 6 hours. Next, the mechanism of how ST3G12-PS antibody conjugate compound 901 enters the cell was examined. MDA-MB-468 (STAT3 high) and MCF-10A (STAT3 low) cells were seeded at 5,000 cells per well in a 96 well plate overnight. Cells were treated with the clathrin inhibitor Pitstop2 (60 uM) or the caveolin inhibitor filipin (1 ug/ml) for 30 minutes. 20 ug/ml of OS-STAT3-Alexa488 (compound 901-Alexa488) antibody was added for another 30 minutes. Vehicle alone was used as a control. Cells were then fixed and imaged with Incucyte. FIG. 13 shows that ST3G12-PS antibody compound 901 entered MDA-MB-438 (STAT3 high) tumor cells using endocytosis independent mechanisms.

Caveolin and clathrin-dependent ST3G12-PS antibody conjugate (compound 901)-mediated uptake was examined in MCF-10A cells. Clathrin-mediated endocytosis is mediated by small vesicles that have a morphologically characteristic coat made up of a complex of proteins that are mainly associated with the cytosolic protein clathrin. Caveolae are the most common reported non-clathrin-coated plasma membrane buds, which exist on the surface of many, but not all cell types. They consist of the cholesterol-binding protein caveolin (Vip21) with a bilayer enriched in cholesterol and glycolipids. Both clathrin mediated endocytosis and caveolae transport extracellular molecules into the cell. 5,000 cells were seeded per well in a 96 well plate, overnight. Cells were pretreated with the clathrin inhibitor Pitstop2 (30 uM or 60 uM) or the caveolin inhibitor filipin (0.5 ug/ml or 1.0 ug/ml) for 30 minutes. 20 ug/ml of ST3G12-PS-Alexa488 (compound 901-Alexa488) antibody was added for another 30 minutes. Cells were fixed and imaged with IncuCyte. DMSO and antibody only were used as controls. As shown in FIG. 14 panel (i), treatment with the clathrin inhibitor PS2 at concentrations of 30 uM and 60 uM inhibited ST3G12-PS (compound 901) uptake, while treatment with the caveolin inhibitor, filipin, had little effect at a concentration of 0.5 ug/ml, and a greater effect at 1.0 ug/ml. FIG. 14 panel (ii) shows the data normalized to cell count.

FIG. 15 shows the results of the same experiments performed in MDA-MB-468 (STAT3 high) cells.

Example 6. Temperature Dependence of Anti-STAT3 Antibody Entry into Cells

Experiments were carried out to determine if the entrance of anti-STAT3 antibodies modified with PS was dependent on temperature. 10,000 U251 cells were seeded. ST3G12-PS conjugate (compound 901) was incubated at 37° C. or 4° C., at a concentration of 20 ug/mL for selected time, then fixed in 4% PFA. Cells were permeabilized with 0.1% tritonX, and then locked with 3% BSA, and treated with 1:250 Alexa 488 GAH IgG. Cells were then washed and imaged. The results are shown in FIG. 16A and FIG. 16B. FIG. 16A shows an inhibition of ST3G12-PS (compound 901) at 4° C., where, as time increased, the green object count did not increase. For ST3G12-PS (compound 901) at 37° C., the green object count increased until 240 min After 240 min there was either a taper or a plateau. FIG. 16B compares the 240 minute time point from the experiment described in FIG. 16A ("37° C. 1" and "4° C. 1") with a second experiment at the 240 minute time point ("37° C. 2" and 4° C. 2")). The signal at 4 C remained about the same, but a large boost in 37° C. signal was observed.

Example 7. Blocking IL-26-STAT3 Pathway in COLO205

The effect of the anti-STAT3 antibody conjugate (compound 901) on expression of STAT3 downstream genes was examined. STAT3 interacts with SIE (sis-inducible element), thereby inducing transcription of genes. Two constructs were used—one with tandem repeats of SIE upstream of the TATA box, and the other without the SIE tandem repeats to serve as a control. A schematic of these constructs is shown in FIG. 17C. First, the effect of the anti-STAT3 antibody conjugate (compound 901) on reporter activity in HeLa or U251 cells was tested. FIG. 17D shows the results of the STAT3 reporter assay in HeLa cells. FIG. 17E shows the results of the STAT3 reporter assay in U251 cells. Percent induction of reporter activity compared to vehicle was reported. Oncostatin M (OSM), a JAK activator, was used to activate JAK. Activated JAKs phosphorylate additional targets, including both the receptors and the major substrates, STATs. The STAT3 SH2 domain inhibitor 5, 15-DPP was also used. Cells were transfected with the constructs shown in FIG. 17C, then treated with the indicated antibodies in the presence of activator or inhibitor. STAT3-downstream transcriptional activity was measured by Luciferase reporter assay. As shown in FIG. 17D and FIG. 17E, the anti-STAT3 antibody conjugate decreased STAT3 reporter activity, compared to control antibody conjugate, no antibody and anti-STAT3 monoclonal antibody.

Next, experiments were carried out to test whether anti-STAT3-PS antibodies (e.g., compound 901) can block expression of IL-26 induced IL-10 cytokine and anti-apoptotic genes BCL2L1 and BIRC5. Briefly, COLO205 cells were seeded at 100 k/well in 12 well plate. Cells were pre-incubated with 50 ug/mL PS-OPRF (an antibody to the OPRF bacterial protein, conjugated to PS, used as a control), unmodified ST3G12, ST3G12-PS (compound 901), or 1 uM JAK inhibitor Tofacitinib for 90 minutes at 37° C. Cells were stimulated overnight with 2.5 ug/mL IL-26 (0.1% Human serum carrier protein). After overnight stimulation, RNA was extracted from cells and reverse transcribed to cDNA followed by rtPCR. The results are shown in FIG. 17A. As shown in FIG. 17A, IL-26 stimulated expression of IL-10, BCL2L1 (BCL-XL, a STAT3-downstream proliferation/survival gene), and BIRC5 (Survivin), which was significantly reversed by ST3G12-PS antibody conjugate compound 901. FIG. 17B shows another set of experiments performed to assess the expression of STAT3-downstream genes in Colo 205 cells treated with a compound 901 using the same method as described above. As shown in FIG. 17B, IL-26 stimulated expression of IL-10 and BCL2L1 was significantly reversed by ST3G12-PS antibody conjugate compound 901.

Example 8. Anti-STAT3 Antibody Conjugate Effect on 2-Dimensional and 3-Dimensional Tumor Cell Growth Experiments were carried out to determine the drug sensitivity of tumor cells to the anti-STAT3 conjugate (compound 901) in a 2-dimensional (2D) tumor growth assay. FIG. 18A shows the percent killing of DU145 human prostate cancer cells that occurred with increasing antibody concentration (μg/ml) in the 2D assay. Growth was monitored by MTS assay in triplicate wells. Error bars show one standard deviation. Cells were plated at a density of $4 \times 10^3$/well in a 96-well plate. Cells were treated with Anti-STAT3 conjugate (compound 901) or control antibody conjugate (Control) for 72 hours. FIG. 18B shows the percent killing of MDA-MB-231 human triple negative breast cancer (TNBC) cells that occurred with increasing antibody concentration (μg/ml) in the 2D assay. Cell viability assay measured by CTG after treatment of cells with the indicated Abs for 3 days.

Cell viability was measured by CTG after treatment of cells with the indicated antibodies for 72 hours. Error bars show one standard deviation. As shown in FIGS. 18A and 18B, STAT3 antibody conjugate (compound 901) reduced the cell viability of human cancer cells.

Next, experiments were carried out to determine the effect of the STAT3 antibody conjugate on penetration of tumor cells and on tumor cell growth in a three-dimensional (3D) model. 3D in vitro models, such as a tumor spheroid model, have been used in cancer research as an intermediate model between in vitro cancer cell line cultures and in vivo tumor. Human colon cancer HCT116 cells were grown in a 3D tumor spheroid model in a ULA (ultra low attachment) plate, and treated with alexa fluor 488 dye labeled anti-STAT3 monoclonal antibody or alexa fluor labeled anti-STAT3 antibody conjugate (compound 901) for one hour to initiate the uptake. Thereafter, spheres were imaged every 10 min for the next 80 hours with ImageExpress. FIG. 18C are images that show detection of the alexa fluor. As shown in FIG. 18C, the anti-STAT3 antibody conjugate (compound 901) was able to penetrate the tumor spheroids (ii) while the anti-STAT3 monoclonal antibodies did not (i). Next, the effect of the anti-STAT3 antibody conjugate (compound 901) on the growth of 3D tumor spheroids was examined DU145 human prostate cancer cells were seeded in ULA plate. Spheres were allowed to form for 72 hours then treated with the indicated antibodies for additional 5 days. Growth was monitored by ImageXpress HCS confocal microscopy (FIG. 19A). CTG assay was used to determine percent viability in FIG. 19B and percent killing in FIG. 19C. Experiments were done in triplicate wells. Error bars represent one standard deviation. As shown in FIG. 19A, the anti-STAT3 antibody conjugate (compound 901) reduced the growth of 3D tumor spheroids. FIG. 19B shows that the antibody conjugate (compound 901) decreased the percent viability of the cells. FIG. 19C shows that the antibody conjugate (compound 901) increased the percent killing of the cells.

The effect of anti-STAT3 antibody conjugates (compound 901) on the growth of glioblastoma cells in a 3D tumor spheroid model was tested. Glioblastoma cells were grown in 3D culture as described above. Cells were treated with anti-STAT3 monoclonal antibodies, control antibody conjugate (anti-OprI-PS) or anti-STAT3 antibody conjugate (e.g. compound 901). Live cells were stained with calcein AM live cell dye, a cell-permeant dye that can be used to determine cell viability. In live cells the nonfluorescent calcein AM is converted to a green-fluorescent calcein. As shown in FIG. 20A, anti-STAT3 antibody conjugate (compound 901) can reduce the size of spheroids. The results shown in FIG. 20A also indicate that the anti-STAT3 antibody conjugate (compound 901) may also induce a differentiated phenotype as shown by morphological characteristics. In glioblastoma and neuroblastoma, a tight link has been recognized between clinical behavior and the stage of tumor cell differentiation, where a higher degree of differentiation indicates a better prognosis than a low degree. Thus, the results shown in FIG. 20A also demonstrate that the anti-STAT3 antibody conjugate (compound 901) may induce differentiation, thereby leading to a better prognosis.

The drug sensitivity to STAT3 antibody conjugate (compound 901) in the 3D-tumor growth assay was tested in patient derived classic glioblastoma (GBM) mesenchymal cells. FIG. 20B shows HCS confocal image of spheroids stained with fluorescent markers against Calcein AM for live cells (green), Ethidium homodimer-1 for dead cells (red) and Hoechst for nuclei (blue). Average total area was calculated by ImageExpress software based on the 2D diameter of spheroids. FIG. 20C shows the average total area of the tumor spheroids after treatment with modified control IgGs (anti-OprI-PS), and modified STAT3 mAbs (compound 901), respectively. AZD1480 is a JAK inhibitor. The drug sensitivity to STAT3 antibody conjugate (compound 901) in the 3D-tumor growth assay was tested in patient derived classic glioblastoma (GBM). FIG. 20D shows ATP levels in cells as an indicator of viable cells in 3D spheroid culture. For this, cells were seeded in a 96-well plate, and the spheroids were allowed to form for 4 days. GBM spheroids were treated with the increased amount of indicated antibodies for additional 7 days, and cell viability was analyzed using CTG 3D assay. FIG. 20D and FIG. 20E show that the anti-STAT3 antibody conjugate (e.g. compound 901) can reduce the size of tumor spheroids.

A functional evaluation of the effect of the anti-STAT3 antibody conjugate (compound 901) on cancer stem cell genes in classic GBM was performed. The results are shown in FIG. 20F and FIG. 20G. FIG. 20F is shows the scatter plots of signal intensity from each sample pair (STAT3 antibody conjugate (compound 901)-treated vs control antibody conjugate (e.g. anti-OprI-PS-treated) at the level of gene expression FIG. 20G shows cancer stem cell genes that were downregulated by anti-STAT3 antibody conjugate (compound 901). As shown in FIG. 20G, RNA was extracted from the spheroid treated with STAT3 antibody conjugate (compound 901) or control antibody conjugate (anti-OprI-PS). Total RNA was then converted into cDNA to measure the transcript levels of STAT3-downstream stemness genes by realtime-quantitative PCR. The results shown in FIG. 20F and FIG. 20G show that anti-STAT3 antibody conjugate (compound 901) can downregulate stemness gene expression in GBM spheroids.

Example 9. Pharmacokinetics of Anti-STAT3 Antibody Conjugates in Mice

The pharmacokinetic properties of the anti-STAT3 antibody conjugates were examined in athymic nude mice. The results are shown in FIG. 21A and in Table 3 below. As shown in FIG. 21A, anti-STAT3 antibody conjugate (compound 901) administered intravenously in mice exhibited acceptable pharmacokinetics.

TABLE 3

|  | Naked anti-STAT3 | Modified anti-STAT3 |
| --- | --- | --- |
| Cmax (ug/ml) | 79.7 | 107.7 |
| CI (ml/day/kg) | 18.7 | 23.7 |
| Vs s (ml/kg) | 83.3 | 138.2 |
| T ½ (hr) | 76.5 | 56.8 |
| AUC (0-336 hr) (day*ug/ml) | 254.6 | 201.8 |

Anti-STAT3 antibody conjugate (compound 901) stability in human serum was tested. The results are shown in FIG. 21B. As shown in FIG. 21B, anti-STAT3 antibody conjugate (compound 901) had high serum stability during the 7-day incubation period. Approximately 60% of the PS oligos remain bound to the antibody.

Example 10. Effect of Anti-STAT3 Antibody Conjugates on Inflammatory Cytokine or Chemokine Response The effect of anti-STAT3 antibody conjugate (compound 901) on the release of proinflammatory cytokines and TLR downstream cytokines/chemokines from human peripheral blood mononuclear cells (PBMCs) in a cohort of 6 donors was examined. The following compounds were tested: ANC 28.1 (anti-CD28) and OKT3 (anti-CD3) as positive control for cytokine activator, Control IgG, anti-STAT3 antibody conjugate (compound 901), PS oligo and anti-STAT3 ST3G12 monoclonal antibodies. PMBCs were incubated with the indicated antibody or olio for 24 hours. After 24 hours, conditioned media was collected for cytokine detection. Compounds were tested at 0.1, 1, 10 and 100 µg/ml. For the monoclonal antibodies, 625 nM equals 100 µg/mL; 62.5 nM equals 10 µg/mL; 6.25 nM equals 1 µg/mL and 0.625 nM equals 0.1 µg/mL. As shown in FIG. 22A, anti-STAT3 antibody conjugate (compound 901) did not stimulate the release of IL-2 from human PMBCs. As shown in FIG. 22B, anti-STAT3 antibody conjugate (compound 901) did not stimulate the release of IL-6 from human PMBCs. As shown in FIG. 22C, anti-STAT3 antibody conjugate (compound 901) did not stimulate the release of IL-8 from human PMBCs. As shown in FIG. 22D, anti-STAT3 antibody conjugate (compound 901) did not stimulate the release of IFN-γ from human PMBCs. Other cytokines tested but not shown include IL-4, IL-10 and TNFα. Together these results show that anti-STAT3 antibody conjugate (compound 901) do not stimulate the release of proinflammatory cytokines and TLR downstream cytokines/chemokines from human peripheral blood mononuclear cells (PBMCs).

The effect of toll-like receptor downstream cytokine and chemokine responses from a cohort of 2 donors was tested. To determine the limits of quantification, cytokine standards were diluted to produce 12-standard concentrations. Each cytokine standard was used to produce a 12-point standard curve. A known concentration of the standard was measured in quadruplicate using the MultiCyt Qbeads PlexScreen platform. The raw data was measured as mean fluorescence intensity (MFI). The concentrations of the samples were interpolated using 4-PLL curve generated from 12 standards. Accuracy was determined as the concentration recovered expressed as a percentage of the actual spiked concentration. The acceptance criterion for accuracy was set at ±30% recovery of actual spiked concentration. The lower limit of quantification (LLOQ) was determined using the lowest standard that was at least above the lowest concentration within acceptance criterion for accuracy. Statistical analyses were done by ANOVA (Dunnett's multiple comparisons test, with a single pooled variance) using GraphPad Prism ($p \leq 0.05$; , $p \leq 0.01$; *, $p \leq 0.001$; ****, $p \leq 0.0001$). FIGS. 23 (i)-(vi) show standard curves showing the range of detection in the MultiCyt Qbeads plexscreen platform for (i) TNFα, (ii) IL-6, (iii) IL-8, (iv) CCL5, (v) CCL4 and (vi) IFNα.

The effect of toll-like receptor downstream cytokine and chemokine responses from a cohort of 2 donors was tested. PMBCs were incubated with the indicated antibody or oligo for 24 hours. After 24 hours, conditioned media was collected for cytokine detection. The MultiCyt Qbeads assay as described above was used for the detection of the TLR-downstream cytokines and chemokines: TNFα, IL-1β, IL-6, IL-8, CCL5 (RANTES), CCL4 (MIP-1β) and IFNα. The following compounds were tested: ODN 2395, ODN 5328, PS oligos and anti-STAT3 antibody conjugates (compound 901). ODN 2395 is a CpG oligodeoxynucleotide toll-like receptor (TLR) agonist, and serves as a positive control. ODN 5328 is a GpC control. Both have a phosphorothioate backbone. Compounds were tested at 1000, 500, 250, 125, 62.5 and 31.25 nM. Compound concentration (nM) is shown on the x-axis, and cytokine/chemokine detected in the conditioned media (pg/mL) is shown on the y-axis.

As shown in FIG. 24A and FIG. 24B, anti-STAT3 antibody conjugate (compound 901) did not stimulate the release of TNFα from human PMBCs. As shown in FIG. 25A and FIG. 25B, anti-STAT3 antibody conjugates did not stimulate the release of IL-6 from human PMBCs. As shown in FIG. 26A and FIG. 26B, anti-STAT3 antibody conjugates did not stimulate the release of IL-8 from human PMBCs. As shown in FIG. 27A and FIG. 27B, anti-STAT3 antibody conjugates did not stimulate the release of CCL5 from human PMBCs. As shown in FIG. 28A and FIG. 28B, anti-STAT3 antibody conjugates did not stimulate the release of CCL7 from human PMBCs. As shown in FIG. 29A and FIG. 29B, anti-STAT3 antibody conjugates did not stimulate the release of IFNα from human PMBCs.

INCORPORATION BY REFERENCE

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

TABLE 4

Sequence Listing

| Antibody | Description | Amino Acid sequence and identifier |
|---|---|---|
| ST1A5 | Heavy chain variable domain | EVQLVESGAEVKKPGASVKVSCKA SGYTFTGYYMHWVRQAPGQGLEW MGWINPNSGGTNYAQKFQGRVTM TRDTSISTAYMELSRLRSDDTAVYY CARDGGLGWGTYFRLGDAFDIWG QGTMVTVSS (SEQ ID NO: 1) |
| ST1A5 | Heavy chain variable domain CDR1 | GYTFTGYY (SEQ ID NO: 7) |
| ST1A5 | Heavy chain variable domain CDR2 | INPNSGGT (SEQ ID NO: 8) |
| ST1A5 | Heavy chain variable domain CDR3 | ARDGGLGWGTYFRLGDAFDI (SEQ ID NO: 9) |
| ST1A5 | Light chain variable domain | QSVLTQPPSVSKGLRQTATLTCTGN SNNVGNEGAAWLQQHQGHPPKLL SYRNFNRPSGISERFSASRSGNTASL TITGLQPEDEADYYCSAWDSSLSA WVFGGGTKLTVL (SEQ ID NO: 2) |
| ST1A5 | Light chain variable domain CDR1 | SNNVGNEG (SEQ ID NO: 10) |
| ST1A5 | Light chain variable domain CDR2 | RNF (SEQ ID NO: 11) |
| ST1A5 | Light chain variable domain CDR3 | SAWDSSLSAWV (SEQ ID NO: 12) |
| ST3G12 | Heavy chain variable domain | QVQLVQSGAEVKKPGASVKVSCKA SGYTFTSYYMHWVRQAPGQGLEW MGIINPSGGSTSYAQKFQGRVTMTR DTSTSTVYMELSSLRSEDTAVYYCA RSDYVHSFDIWGQGTMVTVSS (SEQ ID NO: 3) |
| ST3G12 | Heavy chain variable domain CDR1 | GYTFTSYY (SEQ ID NO: 13) |
| ST3G12 | Heavy chain variable domain CDR2 | INPSGGST (SEQ ID NO: 14) |
| ST3G12 | Heavy chain variable domain CDR3 | ARSDYVHSFDI (SEQ ID NO: 15) |

TABLE 4-continued

Sequence Listing

| Antibody | Description | Amino Acid sequence and identifier |
|---|---|---|
| ST3G12 | Light chain variable domain | QPVLTQPPSASALLGASIKLTCTLSS EHSTYTVEWYQQRPGRSPQYIMNV KSDGSYNKGDGIPDRFMGSSSGAD RYLTFSNLQSDDEAEYHCGESHRID GQVGVVFGGGTKLTVL (SEQ ID NO: 4) |
| ST3G12 | Light chain variable domain CDR1 | SEHSTYT (SEQ ID NO: 16) |
| ST3G12 | Light chain variable domain CDR2 | VKSDGSY (SEQ ID NO: 17) |
| ST3G12 | Light chain variable domain CDR3 | GESHRIDGQVGVV (SEQ ID NO: 18) |

We claim:

1. An isolated anti-Signal Transducer and Activator of Transcription 3 (STAT3) antibody, or an antigen-binding fragment thereof, comprising a heavy chain variable domain comprising a CDR3 domain comprising an amino acid sequence as set forth in SEQ ID NO: 9, a CDR2 domain comprising an amino acid sequence as set forth in SEQ ID NO: 8, and a CDR1 domain comprising an amino acid sequence as set forth in SEQ ID NO: 7; and a light chain variable domain comprising a CDR3 domain comprising an amino acid sequence as set forth in SEQ ID NO: 12, a CDR2 domain comprising an amino acid sequence as set forth in SEQ ID NO: 11, and a CDR1 domain comprising an amino acid sequence as set forth in SEQ ID NO: 10.

2. The antibody, or antigen-binding fragment thereof of claim 1, wherein the heavy chain variable domain comprises an amino acid sequence as set forth in SEQ ID NO: 1, and the light chain variable domain comprises an amino acid sequence as set forth in SEQ ID NO: 2.

3. An isolated anti-STAT3 antibody, or an antigen-binding fragment thereof, comprising a heavy chain variable domain comprising a CDR3 domain comprising an amino acid sequence as set forth in SEQ ID NO: 15, a CDR2 domain comprising an amino acid sequence as set forth in SEQ ID NO: 14, and a CDR1 domain comprising an amino acid sequence as set forth in SEQ ID NO: 13; and a light chain variable domain comprising a CDR3 domain comprising an amino acid sequence as set forth in SEQ ID NO: 18, a CDR2 domain comprising an amino acid sequence as set forth in SEQ ID NO: 17, and a CDR1 domain comprising an amino acid sequence as set forth in SEQ ID NO: 16.

4. The antibody, or antigen-binding fragment thereof of claim 3, wherein the heavy chain variable domain comprises an amino acid sequence as set forth in SEQ ID NO: 3, and the light chain variable domain comprises an amino acid sequence as set forth in SEQ ID NO: 4.

5. The anti-STAT3 antibody, or antigen-binding fragment thereof, of claim 1, wherein the antibody has a $K_D$ of $1 \times 10^{-6}$ M or less.

6. The anti-STAT3 antibody, or antigen-binding fragment thereof, of claim 3, wherein the antibody has a $K_D$ of $1 \times 10^{-6}$ M or less.

7. The anti-STAT3 antibody, or antigen-binding fragment thereof, of claim 1, wherein the antigen-binding fragment is a Fab fragment or an scFv.

8. The anti-STAT3 antibody, or antigen-binding fragment thereof, of claim 3, wherein the antigen-binding fragment is a Fab fragment or an scFv.

9. The anti-STAT3 antibody, or an antigen-binding fragment thereof, of claim 1, which is conjugated to an intracellular delivery compound.

10. The anti-STAT3 antibody, or an antigen-binding fragment thereof, of claim 3, which is conjugated to an intracellular delivery compound.

11. A method for treating a subject having a STAT3 expressing cancer, the method comprising administering an effective amount of the anti-STAT3 antibody, or antigen-binding fragment thereof, of claim 1 to the subject.

12. The method of claim 11, wherein the cancer is a solid tumor.

13. The method of claim 11, wherein the cancer is selected from the group consisting of melanoma, glioma, medulloblastoma, renal cell carcinoma, pancreatic adenocarcinoma, ovarian carcinoma, rhabdomyosarcoma, osteosarcoma, glioblastoma, breast, pancreas, ovarian, prostate, lung, liver, colon, colorectal, gastric, head, neck, and kidney.

14. The method of claim 11, wherein the cancer is a hematological cancer.

15. The method of claim 14, wherein the hematological cancer is selected from the group consisting of acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), megakaryocytic leukemia and large granular lymphocyte leukemia.

16. A method for treating a subject having a STAT3 expressing cancer, the method comprising administering an effective amount of the anti-STAT3 antibody, or antigen-binding fragment thereof, of claim 3 to the subject.

17. A method for treating a subject having an autoimmune disease, the method comprising administering an effective amount of the anti-STAT3 antibody, or antigen-binding fragment thereof, of claim 1 to the subject.

18. The method of claim 17, wherein the autoimmune disease is selected from the group consisting of multiple sclerosis, Crohn's disease, certain bacterially induced colitis, arthritis, lupus, diabetes, asthma, inflammatory bowel disease, scleroderma, and vasculitis.

19. A method for treating a subject having an autoimmune disease, the method comprising administering an effective amount of the anti-STAT3 antibody, or antigen-binding fragment thereof, of claim 3 to the subject.

20. A pharmaceutical composition comprising the anti-STAT3 antibody, or antibody fragment of claim 1, and a pharmaceutically acceptable carrier.

21. A pharmaceutical composition comprising the anti-STAT3 antibody, or antibody fragment of claim 3, and a pharmaceutically acceptable carrier.

* * * * *